United States Patent
Tiller et al.

(10) Patent No.: US 11,702,463 B2
(45) Date of Patent: *Jul. 18, 2023

(54) CANINE ANTIBODY LIBRARIES

(71) Applicant: MORPHOSYS AG, Planegg (DE)

(72) Inventors: Thomas Tiller, Munich (DE); Markus Waldhuber, Munich (DE); Ralf Strohner, Eichenau (DE); Kathrin Ladetzki-Baehs, Planegg (DE); Josef Prassler, Germering (DE)

(73) Assignee: MORPHOSYS AG, Planegg (DE)

( * ) Notice: Subject to any disclaimer, the term of this patent is extended or adjusted under 35 U.S.C. 154(b) by 105 days.

This patent is subject to a terminal disclaimer.

(21) Appl. No.: 17/237,527

(22) Filed: Apr. 22, 2021

(65) Prior Publication Data

US 2021/0317190 A1 Oct. 14, 2021

Related U.S. Application Data

(63) Continuation of application No. 16/624,514, filed as application No. PCT/EP2018/066563 on Jun. 21, 2018, now Pat. No. 11,014,978.

(30) Foreign Application Priority Data

Jun. 22, 2017 (EP) ..................................... 17177322

(51) Int. Cl.
*C07K 16/00* (2006.01)
*C07K 16/18* (2006.01)

(52) U.S. Cl.
CPC ............ *C07K 16/005* (2013.01); *C07K 16/18* (2013.01); *C07K 2317/20* (2013.01); *C07K 2317/40* (2013.01); *C07K 2317/55* (2013.01); *C07K 2317/565* (2013.01); *C07K 2317/92* (2013.01); *C07K 2317/94* (2013.01)

(58) Field of Classification Search
CPC ................ C07K 16/18; C07K 2317/20; C07K 2317/55; C07K 2317/05; C07K 2317/56
See application file for complete search history.

(56) References Cited

U.S. PATENT DOCUMENTS 11,014,978 B2  5/2021  Tiller et al. .......... C07K 16/005

FOREIGN PATENT DOCUMENTS

| CN | 104017080 | 9/1916 | |
|---|---|---|---|
| WO | 2009/126730 | 10/2009 | |
| WO | WO-2009126730 A2 * | 10/2009 | .......... C07K 16/005 |
| WO | 2011092313 | 8/2011 | |

OTHER PUBLICATIONS

Akhova et al. "New Canine Synthetic Antibody Library" 2015 p. 1.
Bao et al. "Molecular characterization of the VH repertoire in Canis familiaris" Veterinary Immunology and Immunopathology 2010 137:64-75.
Biolabs Creative "What You Need to Know About Monoclonal Canine (Dog) Antibody" 2016 pp. 1-2.
Braganza et al. "Generation and validation of canine single chain variable fragment phage display libraries" Veterinary Immunology and Immunopathology 2011 139:27-40.
Gearing et al. "A fully caninised anti-NGF monoclonal antibody for pain relief in dogs" BMC Veterinary Research 2013 9:226 pp. 1-11.
Knappik et al. "Fully Synthetic Human Combinatorial Antibody Libraries (HuCAL) Based on Modular Consensus Frameworks and CDRs Randomized with Trinucleotides" J. Mol. Biol. 2000 296:57-86.
Ray, O. "Unique Monoclonal Canine (Dog) Antibody Production in Creative Biolabs" https://articles.abilogic.com/134652/unique-monoclonal-canine-dog-antibody.html posted Feb. 2, 2016.
Sidhu, S.S. & Fellouse, F.A. "Synthetic therapeutic antibodies" Nature Chemical Biology 2006 2(12) :682-688.
Tiller et al. "A fully synthetic human Fab antibody library based on fixed VH/VL framework pairings with favorable biophysical properties" mAbs 2013 5(3) :445-470.
International Search Report and Written Opinion in PCT/EP2018/066563 dated Jul. 19, 2018.
International Preliminary Report on Patentability in PCT/EP2018/066563 dated Dec. 24, 2019.
Office Communication dated Sep. 22, 2020 in U.S. Appl. No. 16/624,514, filed Dec. 19, 2019.
Office Communication dated Feb. 28, 2021 in U.S. Appl. No. 16/624,514, filed Dec. 19, 2019.

* cited by examiner

Primary Examiner — Sahana S Kaup
(74) Attorney, Agent, or Firm — Licata & Tyrrell P.C.

(57) ABSTRACT

The present invention provides synthetic canine antibody libraries, as well as polypeptides, nucleic acids, vectors, host cells and methods used in conjunction with these libraries. The present invention also provides antibodies isolated from such libraries.

20 Claims, 23 Drawing Sheets

Specification includes a Sequence Listing.

× selected

FIG. 1a

| VH | Vs467 | Vs614 | Vs613 | Vs646 | Vs637 | Vs635 x | Vs620 | Vs638 | Vs616 | Vs648 | Vs615 | Vs634 | Vs644 | Vs632 | Vs625 | Vs633 | Vs642 | Vs647 | Vs640 | Vs624 x | Vs629 | Vs651 |
|---|---|---|---|---|---|---|---|---|---|---|---|---|---|---|---|---|---|---|---|---|---|---|
| Vs467 | 0 | 7 | 8 | 11 | 10 | 10 | 8 | 9 | 10 | 11 | 10 | 10 | 12 | 12 | 12 | 12 | 12 | 12 | 12 | 14 | 14 | 13 |
| Vs614 | 7 | 0 | 6 | 6 | 7 | 9 | 9 | 8 | 9 | 10 | 9 | 11 | 12 | 8 | 9 | 11 | 10 | 11 | 11 | 10 | 13 | 12 |
| Vs613 | 8 | 6 | 0 | 10 | 8 | 7 | 9 | 8 | 6 | 10 | 9 | 9 | 8 | 12 | 8 | 9 | 9 | 13 | 11 | 14 | 13 | 12 |
| Vs646 | 11 | 6 | 10 | 0 | 9 | 10 | 11 | 9 | 12 | 11 | 12 | 13 | 14 | 11 | 11 | 10 | 12 | 12 | 12 | 11 | 12 | 14 |
| Vs637 | 10 | 7 | 8 | 9 | 0 | 10 | 8 | 6 | 12 | 10 | 13 | 13 | 12 | 12 | 10 | 11 | 11 | 12 | 13 | 10 | 14 | 12 |
| Vs635 x | 10 | 9 | 7 | 10 | 10 | 0 | 10 | 8 | 12 | 10 | 11 | 12 | 10 | 14 | 11 | 9 | 13 | 13 | 12 | 13 | 13 | 13 |
| Vs620 | 8 | 9 | 9 | 11 | 8 | 10 | 0 | 8 | 9 | 10 | 11 | 12 | 8 | 13 | 12 | 11 | 12 | 11 | 12 | 14 | 13 | 11 |
| Vs638 | 9 | 8 | 8 | 9 | 6 | 8 | 8 | 0 | 9 | 6 | 8 | 10 | 9 | 13 | 10 | 9 | 9 | 11 | 11 | 10 | 12 | 9 |
| Vs616 | 10 | 9 | 6 | 12 | 12 | 12 | 9 | 9 | 0 | 10 | 9 | 11 | 11 | 14 | 11 | 13 | 9 | 14 | 13 | 16 | 14 | 13 |
| Vs648 | 11 | 10 | 10 | 11 | 10 | 10 | 10 | 6 | 10 | 0 | 11 | 12 | 12 | 14 | 11 | 10 | 11 | 12 | 13 | 13 | 13 | 9 |
| Vs615 | 10 | 9 | 9 | 12 | 13 | 11 | 11 | 8 | 9 | 11 | 0 | 12 | 12 | 15 | 13 | 13 | 11 | 16 | 15 | 15 | 15 | 14 |
| Vs634 | 10 | 11 | 9 | 13 | 13 | 12 | 12 | 10 | 11 | 12 | 12 | 0 | 12 | 16 | 13 | 13 | 14 | 14 | 12 | 16 | 16 | 15 |
| Vs644 | 12 | 12 | 8 | 14 | 12 | 10 | 8 | 9 | 11 | 12 | 12 | 12 | 0 | 17 | 11 | 12 | 11 | 16 | 13 | 17 | 14 | 14 |
| Vs632 | 12 | 8 | 12 | 11 | 12 | 14 | 13 | 13 | 14 | 14 | 15 | 16 | 17 | 0 | 12 | 14 | 16 | 15 | 16 | 13 | 16 | 15 |
| Vs625 | 12 | 9 | 8 | 11 | 10 | 11 | 12 | 10 | 11 | 11 | 13 | 13 | 11 | 12 | 0 | 10 | 12 | 14 | 14 | 13 | 14 | 14 |
| Vs633 | 12 | 11 | 9 | 10 | 11 | 9 | 11 | 9 | 13 | 10 | 13 | 13 | 12 | 14 | 10 | 0 | 14 | 10 | 14 | 11 | 6 | 13 |
| Vs642 | 12 | 10 | 9 | 12 | 11 | 13 | 12 | 9 | 9 | 11 | 11 | 14 | 11 | 16 | 12 | 14 | 0 | 16 | 14 | 17 | 13 | 14 |
| Vs647 | 12 | 11 | 13 | 12 | 12 | 13 | 11 | 11 | 14 | 12 | 16 | 14 | 16 | 15 | 14 | 10 | 16 | 0 | 12 | 13 | 13 | 14 |
| Vs640 | 12 | 11 | 11 | 12 | 13 | 12 | 12 | 11 | 13 | 13 | 15 | 12 | 13 | 16 | 14 | 14 | 14 | 12 | 0 | 16 | 18 | 16 |
| Vs624 x | 14 | 10 | 14 | 11 | 10 | 13 | 14 | 10 | 16 | 13 | 15 | 16 | 17 | 13 | 13 | 11 | 17 | 13 | 16 | 0 | 13 | 15 |
| Vs629 | 14 | 13 | 13 | 12 | 14 | 13 | 13 | 12 | 14 | 13 | 15 | 16 | 14 | 16 | 14 | 6 | 13 | 13 | 18 | 13 | 0 | 15 |

FIG. 1b

| VH | Vs627 | Vs623 | Vs618 | Vs622 | Vs626 | Vs645 | Vs630 | Vs619 | Vs650 | Vs636 | Vs639 | Vs649 | Vs631 | Vs612 | Vs621 | Vs643 | Vs641 | Vs617 | Vs628 |
|---|---|---|---|---|---|---|---|---|---|---|---|---|---|---|---|---|---|---|---|
| Vs467 | 12 | 14 | 12 | 17 | 13 | 14 | 14 | 18 | 16 | 16 | 16 | 18 | 23 | 24 | 24 | 24 | 29 | 47 | 47 |
| Vs614 | 13 | 13 | 13 | 11 | 13 | 14 | 14 | 15 | 17 | 16 | 17 | 16 | 21 | 24 | 24 | 24 | 25 | 47 | 47 |
| Vs613 | 11 | 12 | 15 | 16 | 12 | 13 | 13 | 15 | 15 | 15 | 18 | 18 | 21 | 24 | 24 | 23 | 30 | 47 | 49 |
| Vs646 | 14 | 14 | 16 | 11 | 17 | 18 | 18 | 15 | 20 | 20 | 18 | 18 | 23 | 26 | 26 | 25 | 27 | 49 | 50 |
| Vs637 | 14 | 14 | 15 | 14 | 15 | 16 | 16 | 16 | 17 | 18 | 18 | 18 | 20 | 26 | 26 | 22 | 27 | 47 | 50 |
| Vs635 | 13 | 15 | 15 | 16 | 17 | 18 | 15 | 18 | 17 | 18 | 17 | 16 | 22 | 24 | 24 | 23 | 30 | 47 | 50 |
| Vs620 | 13 | 14 | 14 | 16 | 13 | 14 | 15 | 16 | 16 | 18 | 17 | 18 | 21 | 23 | 23 | 25 | 29 | 47 | 48 |
| Vs638 | 11 | 12 | 12 | 14 | 14 | 15 | 14 | 18 | 13 | 16 | 15 | 18 | 20 | 23 | 23 | 20 | 27 | 48 | 48 |
| Vs616 | 13 | 12 | 18 | 17 | 12 | 13 | 14 | 18 | 16 | 16 | 19 | 18 | 23 | 24 | 24 | 26 | 32 | 46 | 48 |
| Vs648 | 12 | 12 | 16 | 16 | 16 | 17 | 18 | 18 | 15 | 20 | 17 | 20 | 23 | 26 | 24 | 24 | 28 | 48 | 49 |
| Vs615 | 14 | 12 | 16 | 16 | 16 | 17 | 15 | 20 | 17 | 18 | 18 | 16 | 23 | 23 | 23 | 24 | 31 | 48 | 47 |
| Vs634 | 6 | 16 | 16 | 18 | 14 | 15 | 18 | 21 | 19 | 21 | 21 | 22 | 24 | 26 | 26 | 25 | 30 | 47 | 49 |
| Vs644 | 15 | 17 | 17 | 19 | 18 | 18 | 16 | 16 | 15 | 18 | 20 | 21 | 24 | 26 | 26 | 25 | 32 | 49 | 49 |
| Vs632 | 16 | 16 | 19 | 17 | 18 | 19 | 20 | 21 | 21 | 22 | 19 | 21 | 24 | 28 | 26 | 27 | 30 | 49 | 52 |
| Vs625 | 13 | 16 | 19 | 18 | 15 | 15 | 18 | 19 | 20 | 21 | 19 | 20 | 25 | 28 | 26 | 24 | 32 | 45 | 50 |
| Vs633 | 12 | 16 | 14 | 18 | 18 | 19 | 16 | 18 | 19 | 18 | 16 | 20 | 25 | 24 | 22 | 25 | 32 | 50 | 48 |
| Vs642 | 16 | 15 | 19 | 14 | 16 | 17 | 18 | 18 | 18 | 20 | 21 | 22 | 24 | 26 | 26 | 25 | 31 | 47 | 48 |
| Vs647 | 14 | 18 | 16 | 17 | 15 | 16 | 20 | 21 | 22 | 22 | 18 | 21 | 24 | 26 | 25 | 25 | 28 | 50 | 54 |
| Vs640 | 15 | 20 | 17 | 19 | 15 | 17 | 16 | 22 | 21 | 18 | 20 | 18 | 26 | 26 | 26 | 25 | 30 | 52 | 52 |
| Vs624 | 15 | 17 | 18 | 17 | 18 | 19 | 20 | 23 | 22 | 22 | 20 | 21 | 25 | 28 | 26 | 26 | 30 | 52 | 54 |
| Vs629 | 15 | 18 | 18 | 19 | 21 | 22 | 18 | 18 | 20 | 21 | 16 | 22 | 24 | 25 | 23 | 27 | 33 | 51 | 50 |

FIG. 1c

| VH | Vs467 | Vs614 | Vs613 | Vs646 | Vs637 | Vs635 x | Vs620 | Vs638 | Vs616 | Vs648 | Vs615 | Vs634 | Vs644 | Vs632 | Vs625 | Vs633 | Vs642 | Vs647 | Vs640 | Vs624 x | Vs629 | Vs651 |
|---|---|---|---|---|---|---|---|---|---|---|---|---|---|---|---|---|---|---|---|---|---|---|
| Vs651 | 13 | 12 | 12 | 14 | 12 | 13 | 11 | 9 | 13 | 9 | 14 | 15 | 14 | 15 | 14 | 13 | 14 | 14 | 16 | 15 | 15 | 0 |
| Vs627 | 12 | 13 | 11 | 14 | 14 | 13 | 13 | 11 | 13 | 12 | 14 | 6 | 15 | 16 | 13 | 12 | 16 | 14 | 15 | 15 | 15 | 14 |
| Vs623 | 14 | 13 | 12 | 14 | 14 | 15 | 14 | 12 | 12 | 12 | 12 | 16 | 17 | 16 | 16 | 16 | 15 | 18 | 20 | 17 | 18 | 15 |
| x Vs618 | 12 | 13 | 15 | 16 | 15 | 15 | 14 | 12 | 18 | 16 | 16 | 16 | 17 | 19 | 19 | 14 | 19 | 16 | 17 | 18 | 18 | 17 |
| Vs622 | 17 | 11 | 16 | 11 | 14 | 16 | 16 | 14 | 17 | 16 | 16 | 18 | 19 | 17 | 18 | 18 | 14 | 17 | 19 | 17 | 19 | 19 |
| Vs626 | 13 | 13 | 12 | 17 | 15 | 17 | 13 | 14 | 12 | 16 | 16 | 14 | 18 | 18 | 15 | 18 | 16 | 15 | 15 | 18 | 21 | 17 |
| Vs645 | 14 | 14 | 13 | 18 | 16 | 18 | 14 | 15 | 13 | 17 | 17 | 15 | 18 | 19 | 15 | 19 | 17 | 16 | 17 | 19 | 22 | 19 |
| Vs630 | 14 | 14 | 13 | 18 | 16 | 15 | 15 | 14 | 14 | 18 | 15 | 18 | 16 | 20 | 18 | 16 | 18 | 20 | 16 | 20 | 18 | 20 |
| Vs619 | 18 | 15 | 15 | 15 | 16 | 18 | 16 | 18 | 18 | 18 | 20 | 21 | 16 | 21 | 19 | 18 | 18 | 21 | 22 | 23 | 18 | 20 |
| Vs650 | 16 | 17 | 15 | 20 | 17 | 17 | 16 | 13 | 16 | 15 | 17 | 19 | 15 | 21 | 20 | 19 | 18 | 22 | 21 | 22 | 20 | 18 |
| Vs636 | 16 | 16 | 15 | 20 | 18 | 18 | 18 | 16 | 16 | 20 | 18 | 21 | 18 | 22 | 21 | 18 | 20 | 22 | 18 | 22 | 21 | 22 |
| x Vs639 | 16 | 17 | 18 | 18 | 18 | 17 | 17 | 15 | 19 | 17 | 18 | 21 | 20 | 19 | 19 | 16 | 21 | 18 | 20 | 20 | 16 | 16 |
| Vs649 | 18 | 16 | 18 | 18 | 18 | 16 | 18 | 18 | 18 | 20 | 16 | 22 | 21 | 21 | 20 | 20 | 22 | 21 | 18 | 21 | 22 | 21 |
| Vs631 | 23 | 21 | 21 | 23 | 20 | 22 | 21 | 20 | 23 | 23 | 23 | 24 | 24 | 24 | 25 | 25 | 24 | 24 | 26 | 25 | 24 | 24 |
| Vs612 | 24 | 24 | 24 | 26 | 26 | 24 | 23 | 23 | 24 | 26 | 23 | 26 | 26 | 28 | 28 | 24 | 26 | 26 | 26 | 28 | 25 | 26 |
| Vs621 | 24 | 24 | 24 | 26 | 26 | 24 | 23 | 23 | 24 | 24 | 23 | 26 | 26 | 26 | 26 | 22 | 26 | 25 | 26 | 26 | 23 | 26 |
| Vs643 | 24 | 24 | 23 | 25 | 22 | 23 | 25 | 20 | 26 | 24 | 24 | 25 | 25 | 27 | 24 | 25 | 25 | 25 | 25 | 26 | 27 | 26 |
| Vs641 | 29 | 25 | 30 | 27 | 27 | 30 | 29 | 27 | 32 | 28 | 31 | 30 | 32 | 30 | 32 | 32 | 31 | 28 | 30 | 30 | 33 | 29 |
| Vs617 | 47 | 47 | 47 | 49 | 47 | 47 | 47 | 48 | 46 | 48 | 48 | 47 | 49 | 49 | 45 | 50 | 47 | 50 | 52 | 52 | 51 | 49 |
| x Vs628 | 47 | 47 | 49 | 50 | 50 | 50 | 48 | 48 | 48 | 49 | 47 | 49 | 49 | 52 | 50 | 48 | 48 | 54 | 52 | 54 | 50 | 48 |

FIG. 1d

| VH | Vs627 | Vs623 | Vs618 x | Vs622 | Vs626 | Vs645 | Vs630 | Vs619 | Vs650 | Vs636 | Vs639 x | Vs649 | Vs631 | Vs612 | Vs621 | Vs643 | Vs641 | Vs617 | Vs628 x |
|---|---|---|---|---|---|---|---|---|---|---|---|---|---|---|---|---|---|---|---|
| Vs651 | 14 | 15 | 17 | 19 | 17 | 19 | 20 | 20 | 18 | 22 | 16 | 21 | 24 | 26 | 26 | 26 | 29 | 49 | 48 |
| Vs627 | 0 | 16 | 17 | 19 | 16 | 17 | 21 | 23 | 20 | 21 | 19 | 21 | 25 | 26 | 23 | 26 | 30 | 47 | 48 |
| Vs623 | 16 | 0 | 20 | 18 | 20 | 21 | 20 | 22 | 18 | 22 | 20 | 21 | 24 | 28 | 26 | 29 | 33 | 44 | 52 |
| x Vs618 | 17 | 20 | 0 | 22 | 19 | 22 | 21 | 23 | 22 | 22 | 21 | 21 | 26 | 28 | 28 | 28 | 30 | 49 | 47 |
| Vs622 | 19 | 18 | 22 | 0 | 22 | 23 | 22 | 21 | 24 | 24 | 25 | 22 | 26 | 27 | 27 | 19 | 20 | 50 | 54 |
| Vs626 | 16 | 20 | 19 | 22 | 0 | 9 | 20 | 22 | 20 | 22 | 21 | 24 | 25 | 26 | 26 | 28 | 29 | 52 | 52 |
| Vs645 | 17 | 21 | 22 | 23 | 9 | 0 | 22 | 26 | 23 | 24 | 24 | 25 | 29 | 32 | 32 | 31 | 33 | 50 | 52 |
| Vs630 | 21 | 20 | 21 | 22 | 20 | 22 | 0 | 23 | 21 | 2 | 22 | 23 | 27 | 27 | 27 | 29 | 33 | 53 | 52 |
| Vs619 | 23 | 22 | 23 | 21 | 22 | 26 | 23 | 0 | 18 | 25 | 24 | 28 | 27 | 32 | 32 | 31 | 27 | 56 | 55 |
| Vs650 | 20 | 18 | 22 | 24 | 20 | 23 | 21 | 18 | 0 | 22 | 22 | 26 | 25 | 28 | 28 | 28 | 32 | 53 | 52 |
| Vs636 | 21 | 22 | 22 | 24 | 22 | 24 | 2 | 25 | 22 | 0 | 24 | 24 | 29 | 28 | 28 | 32 | 35 | 55 | 52 |
| x Vs639 | 19 | 20 | 21 | 25 | 21 | 24 | 22 | 24 | 22 | 24 | 0 | 22 | 30 | 31 | 28 | 30 | 31 | 52 | 54 |
| Vs649 | 21 | 21 | 21 | 22 | 24 | 25 | 23 | 28 | 26 | 24 | 22 | 0 | 32 | 31 | 31 | 29 | 32 | 53 | 54 |
| Vs631 | 25 | 24 | 26 | 26 | 25 | 29 | 27 | 27 | 25 | 29 | 30 | 32 | 0 | 33 | 33 | 31 | 33 | 55 | 56 |
| Vs612 | 26 | 28 | 28 | 27 | 26 | 32 | 27 | 32 | 28 | 28 | 31 | 31 | 33 | 0 | 2 | 32 | 38 | 57 | 56 |
| Vs621 | 23 | 26 | 28 | 27 | 26 | 32 | 27 | 32 | 28 | 28 | 28 | 31 | 33 | 2 | 0 | 32 | 38 | 57 | 57 |
| Vs643 | 26 | 29 | 28 | 19 | 28 | 31 | 29 | 31 | 28 | 32 | 30 | 29 | 31 | 32 | 32 | 0 | 27 | 57 | 59 |
| Vs641 | 30 | 33 | 30 | 20 | 29 | 33 | 33 | 27 | 32 | 35 | 31 | 32 | 33 | 38 | 38 | 27 | 0 | 61 | 60 |
| Vs617 | 47 | 44 | 49 | 50 | 52 | 50 | 53 | 56 | 53 | 55 | 52 | 53 | 55 | 57 | 57 | 57 | 61 | 0 | 56 |
| x Vs628 | 48 | 52 | 47 | 54 | 52 | 52 | 52 | 55 | 52 | 52 | 54 | 54 | 56 | 56 | 57 | 59 | 60 | 56 | 0 |

| Vlambda | Vs316 | Vs840 | Vs332 | Vs849 | Vs340 | Vs355 | Vs318 | Vs465 | Vs835 | Vs927 | Vs343 | Vs346 | Vs357 | Vs850 | Vs338 | Vs317 | Vs924 | Vs922 | Vs333 | Vs921 | Vs841 | Vs321 |
|---|---|---|---|---|---|---|---|---|---|---|---|---|---|---|---|---|---|---|---|---|---|---|
| Vs316 | 0 | 2 | 3 | 10 | 9 | 13 | 19 | 19 | 19 | 19 | 18 | 18 | 16 | 24 | 19 | 48 | 48 | 48 | 47 | 47 | 47 | 46 |
| Vs840 | 2 | 0 | 3 | 10 | 9 | 15 | 19 | 19 | 19 | 19 | 18 | 18 | 16 | 24 | 19 | 47 | 47 | 46 | 46 | 46 | 46 | 45 |
| Vs332 | 3 | 3 | 0 | 7 | 6 | 12 | 17 | 17 | 17 | 17 | 16 | 16 | 16 | 24 | 18 | 48 | 48 | 48 | 47 | 47 | 47 | 46 |
| Vs849 | 10 | 10 | 7 | 0 | 12 | 19 | 24 | 24 | 24 | 24 | 22 | 22 | 22 | 29 | 24 | 52 | 52 | 51 | 50 | 50 | 50 | 49 |
| Vs340 | 9 | 9 | 6 | 12 | 0 | 12 | 18 | 18 | 18 | 18 | 17 | 18 | 17 | 26 | 19 | 50 | 50 | 49 | 49 | 49 | 49 | 48 |
| Vs355 | 13 | 15 | 12 | 19 | 12 | 0 | 18 | 18 | 18 | 18 | 17 | 20 | 18 | 29 | 25 | 52 | 52 | 50 | 50 | 50 | 50 | 49 |
| Vs318 | 19 | 19 | 17 | 24 | 18 | 18 | 0 | 0 | 0 | 0 | 6 | 10 | 16 | 30 | 24 | 53 | 53 | 51 | 52 | 52 | 52 | 49 |
| Vs465 | 19 | 19 | 17 | 24 | 18 | 18 | 0 | 0 | 0 | 0 | 6 | 10 | 16 | 30 | 24 | 53 | 53 | 51 | 52 | 52 | 52 | 49 |
| Vs835 | 19 | 19 | 17 | 24 | 18 | 18 | 0 | 0 | 0 | 0 | 6 | 10 | 16 | 30 | 24 | 53 | 53 | 51 | 52 | 52 | 52 | 49 |
| Vs927 | 19 | 19 | 17 | 24 | 18 | 18 | 0 | 0 | 0 | 0 | 6 | 10 | 16 | 30 | 24 | 53 | 53 | 51 | 52 | 52 | 52 | 49 |
| Vs343 | 18 | 18 | 16 | 22 | 17 | 17 | 6 | 6 | 6 | 6 | 0 | 10 | 17 | 29 | 22 | 52 | 52 | 50 | 50 | 50 | 50 | 48 |
| Vs346 | 18 | 18 | 16 | 22 | 18 | 20 | 10 | 10 | 10 | 10 | 10 | 0 | 18 | 28 | 24 | 48 | 48 | 48 | 47 | 47 | 47 | 45 |
| Vs357 | 16 | 16 | 16 | 22 | 17 | 18 | 16 | 16 | 16 | 16 | 17 | 18 | 0 | 17 | 19 | 49 | 49 | 49 | 48 | 48 | 48 | 46 |
| Vs850 | 24 | 24 | 24 | 29 | 26 | 29 | 30 | 30 | 30 | 30 | 29 | 28 | 17 | 0 | 25 | 49 | 49 | 49 | 48 | 48 | 48 | 47 |
| Vs338 | 19 | 19 | 18 | 24 | 19 | 25 | 24 | 24 | 24 | 24 | 22 | 24 | 19 | 25 | 0 | 48 | 48 | 47 | 47 | 47 | 47 | 44 |
| Vs317 | 48 | 47 | 48 | 52 | 50 | 52 | 53 | 53 | 53 | 53 | 52 | 48 | 49 | 49 | 48 | 0 | 0 | 1 | 2 | 2 | 2 | 8 |
| Vs924 | 48 | 47 | 48 | 52 | 50 | 52 | 53 | 53 | 53 | 53 | 52 | 48 | 49 | 49 | 48 | 0 | 0 | 1 | 2 | 2 | 2 | 8 |
| Vs922 | 48 | 46 | 48 | 51 | 49 | 50 | 51 | 51 | 51 | 51 | 50 | 48 | 49 | 49 | 47 | 1 | 1 | 0 | 1 | 1 | 1 | 7 |
| Vs333 | 47 | 46 | 47 | 50 | 49 | 50 | 52 | 52 | 52 | 52 | 50 | 47 | 48 | 48 | 47 | 2 | 2 | 1 | 0 | 0 | 2 | 8 |
| Vs921 | 47 | 46 | 47 | 50 | 49 | 50 | 52 | 52 | 52 | 52 | 50 | 47 | 48 | 48 | 47 | 2 | 2 | 1 | 0 | 0 | 2 | 8 |
| Vs841 | 47 | 46 | 47 | 50 | 49 | 50 | 52 | 52 | 52 | 52 | 50 | 47 | 48 | 48 | 47 | 2 | 2 | 1 | 2 | 2 | 0 | 7 |
| Vs321 | 46 | 45 | 46 | 49 | 48 | 49 | 49 | 49 | 49 | 49 | 48 | 45 | 46 | 47 | 44 | 8 | 8 | 7 | 8 | 8 | 7 | 0 |

FIG. 3b

| Vlambda | Vs336 | Vs846 | Vs358 | Vs325 | Vs331 | Vs342 | Vs851 | Vs324 | Vs328 | Vs366 | Vs371 | Vs360 | Vs362 | Vs364 | Vs373 | Vs365 (x) | Vs368 | Vs370 | Vs369 | Vs367 | Vs374 |
|---|---|---|---|---|---|---|---|---|---|---|---|---|---|---|---|---|---|---|---|---|---|
| Vs316 | 46 | 46 | 46 | 50 | 45 | 46 | 46 | 46 | 53 | 49 | 49 | 41 | 37 | 43 | 44 | 41 | 43 | 42 | 44 | 45 | 43 |
| Vs840 | 45 | 45 | 45 | 49 | 44 | 45 | 45 | 45 | 53 | 49 | 49 | 41 | 37 | 43 | 44 | 41 | 43 | 42 | 44 | 45 | 43 |
| Vs332 | 46 | 46 | 46 | 50 | 45 | 46 | 46 | 46 | 54 | 49 | 49 | 42 | 38 | 44 | 45 | 42 | 44 | 43 | 45 | 46 | 44 |
| Vs849 | 49 | 49 | 49 | 53 | 47 | 49 | 49 | 48 | 55 | 52 | 51 | 48 | 44 | 50 | 51 | 48 | 50 | 49 | 51 | 52 | 48 |
| Vs340 | 48 | 48 | 48 | 52 | 46 | 49 | 48 | 48 | 56 | 51 | 51 | 43 | 38 | 44 | 45 | 42 | 44 | 43 | 45 | 46 | 44 |
| Vs355 | 49 | 49 | 49 | 53 | 48 | 49 | 49 | 49 | 55 | 49 | 50 | 43 | 43 | 46 | 48 | 44 | 46 | 45 | 46 | 49 | 46 |
| Vs318 | 49 | 49 | 48 | 52 | 49 | 49 | 49 | 52 | 56 | 55 | 55 | 46 | 43 | 43 | 46 | 44 | 46 | 44 | 46 | 49 | 48 |
| Vs465 | 49 | 49 | 48 | 52 | 49 | 49 | 49 | 52 | 56 | 55 | 55 | 46 | 43 | 43 | 46 | 44 | 46 | 44 | 46 | 49 | 48 |
| Vs835 | 49 | 49 | 48 | 52 | 49 | 49 | 49 | 52 | 56 | 55 | 55 | 46 | 43 | 43 | 46 | 44 | 46 | 44 | 46 | 49 | 48 |
| Vs927 | 49 | 49 | 48 | 52 | 49 | 49 | 49 | 52 | 56 | 55 | 55 | 46 | 43 | 43 | 46 | 44 | 46 | 44 | 46 | 49 | 48 |
| Vs343 | 48 | 48 | 47 | 52 | 48 | 47 | 48 | 49 | 53 | 54 | 54 | 44 | 43 | 44 | 48 | 44 | 46 | 44 | 45 | 48 | 46 |
| Vs346 | 45 | 45 | 46 | 49 | 46 | 45 | 45 | 47 | 54 | 54 | 54 | 44 | 45 | 45 | 49 | 45 | 48 | 45 | 49 | 50 | 48 |
| Vs357 | 46 | 46 | 45 | 49 | 46 | 46 | 45 | 48 | 54 | 49 | 49 | 42 | 36 | 41 | 42 | 37 | 40 | 40 | 44 | 45 | 42 |
| Vs850 | 47 | 47 | 47 | 52 | 49 | 47 | 48 | 53 | 55 | 49 | 49 | 49 | 45 | 50 | 50 | 46 | 48 | 49 | 48 | 52 | 48 |
| Vs338 | 44 | 44 | 44 | 50 | 45 | 44 | 46 | 49 | 52 | 49 | 48 | 39 | 38 | 39 | 42 | 40 | 42 | 40 | 42 | 42 | 39 |
| Vs317 | 7 | 7 | 13 | 19 | 18 | 20 | 19 | 24 | 51 | 52 | 52 | 45 | 47 | 52 | 52 | 47 | 49 | 49 | 49 | 52 | 52 |
| Vs924 | 7 | 7 | 13 | 19 | 18 | 20 | 19 | 24 | 51 | 52 | 52 | 45 | 47 | 52 | 52 | 47 | 49 | 49 | 49 | 52 | 52 |
| Vs922 | 6 | 6 | 13 | 19 | 17 | 19 | 19 | 25 | 52 | 51 | 51 | 44 | 45 | 50 | 50 | 45 | 48 | 48 | 46 | 49 | 50 |
| Vs333 | 7 | 7 | 13 | 19 | 18 | 20 | 19 | 24 | 52 | 52 | 52 | 44 | 46 | 50 | 50 | 46 | 48 | 48 | 48 | 50 | 50 |
| Vs921 | 7 | 7 | 13 | 19 | 18 | 20 | 19 | 24 | 52 | 52 | 52 | 44 | 46 | 50 | 50 | 46 | 48 | 48 | 48 | 50 | 50 |
| Vs841 | 6 | 6 | 11 | 18 | 17 | 19 | 18 | 23 | 51 | 51 | 50 | 44 | 46 | 50 | 50 | 46 | 48 | 48 | 48 | 50 | 50 |
| x Vs321 | 2 | 2 | 9 | 13 | 12 | 14 | 14 | 20 | 48 | 48 | 47 | 39 | 42 | 46 | 46 | 41 | 44 | 42 | 45 | 47 | 47 |

FIG. 3c

| Vlambda | Vs361 | Vs363 | Vs372 | Vs359 | Vs330 | Vs352 | Vs349 | Vs838 | Vs468 | Vs844 | Vs456 | Vs457 | Vs326 | Vs350 | Vs353 | Vs322 | Vs345 | Vs356 | Vs327 | Vs334 | Vs845 |
|---|---|---|---|---|---|---|---|---|---|---|---|---|---|---|---|---|---|---|---|---|---|
| Vs316 | 36 | 35 | 45 | 30 | 29 | 28 | 35 | 35 | 36 | 34 | 34 | 34 | 30 | 26 | 28 | 40 | 31 | 28 | 27 | 32 | 32 |
| Vs840 | 37 | 36 | 44 | 29 | 28 | 27 | 35 | 35 | 36 | 34 | 34 | 34 | 30 | 25 | 27 | 40 | 31 | 28 | 26 | 31 | 31 |
| Vs332 | 37 | 36 | 45 | 29 | 28 | 27 | 35 | 35 | 36 | 34 | 34 | 34 | 28 | 25 | 27 | 38 | 30 | 27 | 26 | 32 | 32 |
| Vs849 | 43 | 42 | 50 | 35 | 34 | 31 | 40 | 40 | 42 | 39 | 39 | 39 | 35 | 32 | 34 | 43 | 35 | 34 | 31 | 39 | 39 |
| Vs340 | 37 | 36 | 45 | 32 | 31 | 30 | 35 | 35 | 36 | 34 | 34 | 34 | 31 | 26 | 29 | 40 | 31 | 28 | 27 | 34 | 34 |
| Vs355 | 41 | 40 | 46 | 36 | 31 | 31 | 32 | 32 | 35 | 32 | 32 | 32 | 33 | 32 | 32 | 42 | 35 | 34 | 32 | 38 | 38 |
| Vs318 | 42 | 42 | 44 | 35 | 31 | 30 | 36 | 36 | 37 | 35 | 36 | 35 | 33 | 30 | 33 | 44 | 39 | 35 | 32 | 37 | 37 |
| Vs465 | 42 | 42 | 44 | 35 | 31 | 30 | 36 | 36 | 37 | 35 | 36 | 35 | 33 | 30 | 33 | 44 | 39 | 35 | 32 | 37 | 37 |
| Vs835 | 42 | 42 | 44 | 35 | 31 | 30 | 36 | 36 | 37 | 35 | 36 | 35 | 33 | 30 | 33 | 44 | 39 | 35 | 32 | 37 | 37 |
| Vs927 | 42 | 42 | 44 | 35 | 31 | 30 | 36 | 36 | 37 | 35 | 36 | 35 | 33 | 30 | 33 | 44 | 39 | 35 | 32 | 37 | 37 |
| Vs343 | 40 | 40 | 45 | 32 | 30 | 29 | 37 | 37 | 38 | 36 | 37 | 36 | 28 | 27 | 31 | 44 | 36 | 32 | 30 | 36 | 36 |
| Vs346 | 42 | 41 | 50 | 35 | 31 | 30 | 37 | 37 | 38 | 36 | 37 | 36 | 32 | 30 | 33 | 47 | 39 | 35 | 32 | 38 | 38 |
| Vs357 | 37 | 36 | 44 | 29 | 28 | 27 | 34 | 34 | 35 | 32 | 32 | 32 | 30 | 26 | 26 | 41 | 32 | 28 | 27 | 31 | 31 |
| Vs850 | 45 | 44 | 51 | 35 | 32 | 32 | 44 | 44 | 45 | 43 | 43 | 43 | 38 | 31 | 32 | 43 | 35 | 31 | 34 | 34 | 34 |
| Vs338 | 39 | 39 | 47 | 28 | 23 | 23 | 32 | 32 | 33 | 31 | 31 | 31 | 26 | 21 | 20 | 37 | 24 | 23 | 24 | 28 | 28 |
| Vs317 | 47 | 48 | 57 | 47 | 47 | 46 | 46 | 46 | 49 | 47 | 48 | 47 | 47 | 43 | 47 | 51 | 52 | 41 | 43 | 42 | 42 |
| Vs924 | 47 | 48 | 57 | 47 | 47 | 46 | 46 | 46 | 49 | 47 | 48 | 47 | 47 | 43 | 47 | 51 | 52 | 41 | 43 | 42 | 42 |
| Vs922 | 45 | 46 | 55 | 45 | 46 | 45 | 46 | 46 | 48 | 47 | 48 | 47 | 46 | 42 | 45 | 50 | 51 | 40 | 42 | 40 | 40 |
| Vs333 | 46 | 47 | 56 | 46 | 46 | 44 | 46 | 46 | 49 | 47 | 48 | 47 | 46 | 42 | 46 | 50 | 50 | 40 | 42 | 41 | 41 |
| Vs921 | 46 | 47 | 56 | 46 | 46 | 44 | 46 | 46 | 49 | 47 | 48 | 47 | 46 | 42 | 46 | 50 | 50 | 40 | 42 | 41 | 41 |
| Vs841 | 46 | 47 | 56 | 46 | 46 | 44 | 46 | 46 | 49 | 47 | 48 | 47 | 46 | 42 | 46 | 50 | 50 | 40 | 42 | 41 | 41 |
| x Vs321 | 42 | 45 | 53 | 43 | 43 | 42 | 43 | 43 | 47 | 44 | 46 | 44 | 44 | 40 | 44 | 48 | 48 | 38 | 40 | 39 | 39 |

FIG. 3d

| Vlambda | Vs337 | Vs344 | Vs341 | Vs348 | Vs319 | Vs842 | Vs351 | Vs354 | Vs320 | Vs834 | Vs925 | Vs848 | Vs329 | Vs335 | Vs847 | Vs323 [x] | Vs339 | Vs837 | Vs923 | Vs843 [x] | Vs466 | Vs836 |
|---|---|---|---|---|---|---|---|---|---|---|---|---|---|---|---|---|---|---|---|---|---|---|
| Vs316 | 31 | 29 | 28 | 25 | 25 | 25 | 27 | 25 | 33 | 33 | 33 | 33 | 32 | 26 | 26 | 25 | 27 | 27 | 27 | 27 | 25 | 25 |
| Vs840 | 30 | 28 | 27 | 24 | 24 | 24 | 26 | 24 | 32 | 32 | 32 | 34 | 31 | 25 | 25 | 24 | 26 | 26 | 26 | 26 | 24 | 24 |
| Vs332 | 29 | 28 | 28 | 24 | 24 | 24 | 26 | 24 | 33 | 33 | 33 | 35 | 32 | 26 | 26 | 25 | 27 | 27 | 27 | 27 | 25 | 25 |
| Vs849 | 36 | 32 | 35 | 31 | 31 | 31 | 33 | 31 | 36 | 36 | 36 | 39 | 38 | 33 | 33 | 32 | 34 | 34 | 34 | 34 | 32 | 32 |
| Vs340 | 31 | 30 | 30 | 24 | 24 | 24 | 26 | 24 | 34 | 34 | 34 | 37 | 31 | 28 | 28 | 25 | 28 | 28 | 28 | 28 | 25 | 25 |
| Vs355 | 36 | 35 | 34 | 31 | 31 | 31 | 31 | 31 | 40 | 40 | 40 | 41 | 36 | 32 | 32 | 31 | 29 | 32 | 32 | 32 | 31 | 31 |
| Vs318 | 35 | 34 | 34 | 31 | 30 | 30 | 32 | 28 | 35 | 35 | 35 | 36 | 35 | 30 | 30 | 30 | 32 | 34 | 34 | 34 | 32 | 32 |
| Vs465 | 35 | 34 | 34 | 31 | 30 | 30 | 32 | 28 | 35 | 35 | 35 | 36 | 35 | 30 | 30 | 30 | 32 | 34 | 34 | 34 | 32 | 32 |
| Vs835 | 35 | 34 | 34 | 31 | 30 | 30 | 32 | 28 | 35 | 35 | 35 | 36 | 35 | 30 | 30 | 30 | 32 | 34 | 34 | 34 | 32 | 32 |
| Vs927 | 35 | 34 | 34 | 31 | 30 | 30 | 32 | 28 | 35 | 35 | 35 | 36 | 35 | 30 | 30 | 30 | 32 | 34 | 34 | 34 | 32 | 32 |
| Vs343 | 32 | 31 | 33 | 30 | 27 | 27 | 30 | 26 | 34 | 34 | 34 | 33 | 33 | 27 | 27 | 27 | 30 | 31 | 31 | 31 | 30 | 30 |
| Vs346 | 35 | 34 | 35 | 31 | 30 | 30 | 32 | 28 | 35 | 35 | 35 | 36 | 34 | 30 | 30 | 30 | 32 | 34 | 34 | 34 | 32 | 32 |
| Vs357 | 30 | 28 | 30 | 25 | 22 | 22 | 24 | 23 | 34 | 34 | 34 | 35 | 31 | 27 | 27 | 24 | 27 | 26 | 26 | 27 | 24 | 24 |
| Vs850 | 35 | 31 | 34 | 30 | 26 | 26 | 28 | 27 | 36 | 36 | 36 | 38 | 34 | 32 | 32 | 28 | 32 | 30 | 30 | 31 | 28 | 28 |
| Vs338 | 24 | 23 | 24 | 20 | 18 | 18 | 20 | 16 | 26 | 26 | 26 | 28 | 24 | 19 | 19 | 18 | 20 | 21 | 21 | 21 | 20 | 20 |
| Vs317 | 44 | 42 | 47 | 45 | 44 | 44 | 44 | 44 | 44 | 44 | 44 | 46 | 46 | 45 | 45 | 44 | 42 | 41 | 41 | 41 | 43 | 43 |
| Vs924 | 44 | 42 | 47 | 45 | 44 | 44 | 44 | 44 | 44 | 44 | 44 | 46 | 46 | 45 | 45 | 44 | 42 | 41 | 41 | 41 | 43 | 43 |
| Vs922 | 44 | 41 | 46 | 44 | 43 | 43 | 43 | 43 | 43 | 43 | 43 | 45 | 45 | 44 | 44 | 43 | 41 | 40 | 40 | 40 | 42 | 42 |
| Vs333 | 43 | 41 | 46 | 44 | 43 | 43 | 43 | 43 | 43 | 43 | 43 | 45 | 45 | 44 | 44 | 43 | 41 | 40 | 40 | 40 | 42 | 42 |
| Vs921 | 43 | 41 | 46 | 44 | 43 | 43 | 43 | 43 | 43 | 43 | 43 | 45 | 45 | 44 | 44 | 43 | 41 | 40 | 40 | 40 | 42 | 42 |
| Vs841 | 43 | 41 | 46 | 44 | 43 | 43 | 43 | 43 | 43 | 43 | 43 | 45 | 45 | 44 | 44 | 43 | 41 | 40 | 40 | 40 | 42 | 42 |
| [x] Vs321 | 41 | 39 | 45 | 43 | 40 | 40 | 40 | 40 | 39 | 39 | 39 | 42 | 43 | 42 | 42 | 40 | 39 | 38 | 38 | 37 | 39 | 39 |

FIG. 3e

| Vlambda | Vs316 | Vs840 | Vs332 | Vs849 | Vs340 | Vs355 | Vs318 | Vs465 | Vs835 | Vs927 | Vs343 | Vs346 | Vs357 | Vs850 | Vs338 | Vs317 | Vs924 | Vs922 | Vs333 | Vs921 | Vs841 | x Vs321 |
|---|---|---|---|---|---|---|---|---|---|---|---|---|---|---|---|---|---|---|---|---|---|---|
| Vs336 | 46 | 45 | 46 | 49 | 48 | 49 | 49 | 49 | 49 | 49 | 48 | 45 | 46 | 47 | 44 | 7 | 7 | 6 | 7 | 7 | 6 | 2 |
| Vs846 | 46 | 45 | 46 | 49 | 48 | 49 | 49 | 49 | 49 | 49 | 48 | 45 | 46 | 47 | 44 | 7 | 7 | 6 | 7 | 7 | 6 | 2 |
| Vs358 | 46 | 45 | 46 | 49 | 48 | 49 | 48 | 48 | 48 | 48 | 47 | 46 | 45 | 47 | 44 | 13 | 13 | 13 | 13 | 13 | 11 | 9 |
| Vs325 | 50 | 49 | 50 | 53 | 52 | 53 | 52 | 52 | 52 | 52 | 52 | 49 | 49 | 52 | 50 | 19 | 19 | 19 | 19 | 19 | 18 | 13 |
| Vs331 | 45 | 44 | 45 | 47 | 46 | 48 | 49 | 49 | 49 | 49 | 48 | 46 | 46 | 49 | 45 | 18 | 18 | 17 | 18 | 18 | 17 | 12 |
| Vs342 | 46 | 45 | 46 | 49 | 49 | 49 | 49 | 49 | 49 | 49 | 47 | 45 | 46 | 47 | 44 | 20 | 20 | 19 | 20 | 20 | 19 | 14 |
| Vs851 | 46 | 45 | 46 | 49 | 48 | 49 | 49 | 49 | 49 | 49 | 48 | 45 | 45 | 48 | 46 | 19 | 19 | 19 | 19 | 19 | 18 | 14 |
| Vs324 | 46 | 45 | 46 | 48 | 48 | 49 | 52 | 52 | 52 | 52 | 49 | 47 | 48 | 53 | 49 | 24 | 24 | 25 | 24 | 24 | 23 | 20 |
| Vs328 | 53 | 53 | 54 | 55 | 56 | 55 | 56 | 56 | 56 | 56 | 53 | 54 | 54 | 55 | 52 | 51 | 51 | 52 | 52 | 52 | 51 | 48 |
| Vs366 | 49 | 49 | 49 | 52 | 51 | 49 | 55 | 55 | 55 | 55 | 54 | 54 | 49 | 49 | 49 | 52 | 52 | 51 | 52 | 52 | 51 | 48 |
| Vs371 | 49 | 49 | 49 | 51 | 51 | 50 | 55 | 55 | 55 | 55 | 54 | 54 | 49 | 49 | 48 | 52 | 52 | 51 | 52 | 52 | 50 | 47 |
| Vs360 | 41 | 41 | 42 | 48 | 43 | 43 | 46 | 46 | 46 | 46 | 44 | 44 | 42 | 49 | 39 | 45 | 45 | 44 | 44 | 44 | 44 | 39 |
| Vs362 | 37 | 37 | 38 | 44 | 38 | 43 | 43 | 43 | 43 | 43 | 43 | 45 | 36 | 45 | 38 | 47 | 47 | 45 | 46 | 46 | 46 | 42 |
| Vs364 | 43 | 43 | 44 | 50 | 44 | 46 | 43 | 43 | 43 | 43 | 44 | 45 | 41 | 50 | 39 | 52 | 52 | 50 | 50 | 50 | 50 | 46 |
| Vs373 | 44 | 44 | 45 | 51 | 45 | 48 | 46 | 46 | 46 | 46 | 48 | 49 | 42 | 50 | 42 | 52 | 52 | 50 | 50 | 50 | 50 | 46 |
| x Vs365 | 41 | 41 | 42 | 48 | 42 | 44 | 44 | 44 | 44 | 44 | 44 | 45 | 37 | 46 | 40 | 47 | 47 | 45 | 46 | 46 | 46 | 41 |
| Vs368 | 43 | 43 | 44 | 50 | 44 | 46 | 46 | 46 | 46 | 46 | 48 | 40 | 48 | 42 | 42 | 49 | 49 | 48 | 48 | 48 | 48 | 44 |
| Vs370 | 42 | 42 | 43 | 49 | 43 | 45 | 44 | 44 | 44 | 44 | 44 | 45 | 40 | 49 | 40 | 49 | 49 | 48 | 48 | 48 | 48 | 42 |
| Vs369 | 44 | 44 | 45 | 51 | 45 | 46 | 46 | 46 | 46 | 46 | 45 | 49 | 44 | 48 | 42 | 49 | 49 | 46 | 48 | 48 | 48 | 45 |
| Vs367 | 45 | 45 | 46 | 52 | 46 | 49 | 49 | 49 | 49 | 49 | 48 | 50 | 45 | 52 | 42 | 52 | 52 | 49 | 50 | 50 | 50 | 47 |
| Vs374 | 43 | 43 | 44 | 48 | 44 | 46 | 48 | 48 | 48 | 48 | 46 | 48 | 42 | 48 | 39 | 52 | 52 | 50 | 50 | 50 | 50 | 47 |

FIG. 3f

| Vlambda | Vs336 | Vs846 | Vs358 | Vs325 | Vs331 | Vs342 | Vs851 | Vs324 | Vs328 | Vs366 | Vs371 | Vs360 | Vs362 | Vs364 | Vs373 | Vs365 x | Vs368 | Vs370 | Vs369 | Vs367 | Vs374 |
|---|---|---|---|---|---|---|---|---|---|---|---|---|---|---|---|---|---|---|---|---|---|
| Vs336 | 0 | 0 | 8 | 13 | 11 | 13 | 12 | 19 | 48 | 48 | 47 | 40 | 42 | 47 | 47 | 42 | 45 | 45 | 45 | 47 | 46 |
| Vs846 | 0 | 0 | 8 | 13 | 11 | 13 | 12 | 19 | 48 | 48 | 47 | 40 | 42 | 47 | 47 | 42 | 45 | 45 | 45 | 47 | 46 |
| Vs358 | 8 | 8 | 0 | 17 | 14 | 16 | 16 | 23 | 48 | 49 | 48 | 40 | 42 | 48 | 48 | 44 | 46 | 46 | 45 | 46 | 44 |
| Vs325 | 13 | 13 | 17 | 0 | 21 | 22 | 22 | 25 | 50 | 52 | 52 | 45 | 46 | 50 | 51 | 45 | 48 | 49 | 48 | 51 | 48 |
| Vs331 | 11 | 11 | 14 | 21 | 0 | 15 | 19 | 20 | 49 | 50 | 49 | 42 | 45 | 50 | 50 | 46 | 48 | 48 | 47 | 49 | 45 |
| Vs342 | 13 | 13 | 16 | 22 | 15 | 0 | 14 | 20 | 49 | 51 | 50 | 46 | 47 | 49 | 54 | 49 | 50 | 49 | 49 | 50 | 49 |
| Vs851 | 12 | 12 | 16 | 22 | 19 | 14 | 0 | 22 | 48 | 49 | 48 | 44 | 47 | 49 | 52 | 47 | 49 | 47 | 49 | 50 | 48 |
| Vs324 | 19 | 19 | 23 | 25 | 20 | 20 | 22 | 0 | 51 | 53 | 53 | 47 | 49 | 53 | 54 | 47 | 49 | 50 | 50 | 53 | 53 |
| Vs328 | 48 | 48 | 48 | 50 | 49 | 49 | 48 | 51 | 0 | 44 | 44 | 55 | 53 | 59 | 56 | 53 | 53 | 53 | 52 | 57 | 56 |
| Vs366 | 48 | 48 | 49 | 52 | 50 | 51 | 49 | 53 | 44 | 0 | 4 | 50 | 48 | 54 | 54 | 50 | 52 | 50 | 50 | 52 | 53 |
| Vs371 | 47 | 47 | 48 | 52 | 49 | 50 | 48 | 53 | 44 | 4 | 0 | 51 | 49 | 55 | 55 | 51 | 52 | 51 | 51 | 51 | 54 |
| Vs360 | 40 | 40 | 40 | 45 | 42 | 46 | 44 | 47 | 55 | 50 | 51 | 0 | 20 | 23 | 24 | 21 | 24 | 20 | 25 | 23 | 28 |
| Vs362 | 42 | 42 | 42 | 46 | 45 | 47 | 47 | 49 | 53 | 48 | 49 | 20 | 0 | 22 | 22 | 17 | 18 | 18 | 24 | 24 | 23 |
| Vs364 | 47 | 47 | 48 | 50 | 50 | 49 | 49 | 53 | 59 | 54 | 55 | 23 | 22 | 0 | 9 | 10 | 14 | 9 | 15 | 16 | 25 |
| Vs373 | 47 | 47 | 48 | 51 | 50 | 54 | 52 | 54 | 56 | 54 | 55 | 24 | 22 | 9 | 0 | 11 | 14 | 10 | 16 | 17 | 26 |
| x Vs365 | 42 | 42 | 44 | 45 | 46 | 49 | 47 | 47 | 53 | 50 | 51 | 21 | 17 | 10 | 11 | 0 | 4 | 4 | 11 | 16 | 22 |
| Vs368 | 45 | 45 | 46 | 48 | 48 | 50 | 49 | 49 | 53 | 52 | 52 | 24 | 18 | 14 | 14 | 4 | 0 | 8 | 13 | 20 | 24 |
| Vs370 | 45 | 45 | 46 | 49 | 48 | 49 | 47 | 50 | 53 | 50 | 51 | 20 | 18 | 9 | 10 | 4 | 8 | 0 | 13 | 14 | 24 |
| Vs369 | 45 | 45 | 45 | 48 | 47 | 49 | 49 | 50 | 52 | 50 | 51 | 25 | 24 | 15 | 16 | 11 | 13 | 13 | 0 | 18 | 26 |
| Vs367 | 47 | 47 | 46 | 51 | 49 | 50 | 50 | 53 | 57 | 52 | 51 | 23 | 24 | 16 | 17 | 16 | 20 | 14 | 18 | 0 | 30 |
| Vs374 | 46 | 46 | 44 | 48 | 45 | 49 | 48 | 53 | 56 | 53 | 54 | 28 | 23 | 25 | 26 | 22 | 24 | 24 | 26 | 30 | 0 |

FIG. 3g

| Vlambda | Vs361 | Vs363 | Vs372 | Vs359 | Vs330 | Vs352 | Vs349 | Vs838 | Vs468 | Vs844 | Vs456 | Vs457 | Vs326 | Vs350 | Vs353 | Vs322 | Vs345 | Vs356 | Vs327 | Vs334 | Vs845 |
|---|---|---|---|---|---|---|---|---|---|---|---|---|---|---|---|---|---|---|---|---|---|
| Vs336 | 42 | 45 | 53 | 43 | 43 | 42 | 43 | 43 | 47 | 44 | 46 | 44 | 44 | 40 | 44 | 48 | 48 | 38 | 40 | 38 | 38 |
| Vs846 | 42 | 45 | 53 | 43 | 43 | 42 | 43 | 43 | 47 | 44 | 46 | 44 | 44 | 40 | 44 | 48 | 48 | 38 | 40 | 38 | 38 |
| Vs358 | 41 | 44 | 50 | 42 | 44 | 43 | 44 | 44 | 48 | 46 | 47 | 46 | 44 | 42 | 44 | 49 | 46 | 40 | 39 | 38 | 38 |
| Vs325 | 43 | 49 | 55 | 50 | 48 | 46 | 47 | 47 | 49 | 48 | 49 | 48 | 51 | 46 | 49 | 52 | 52 | 44 | 46 | 45 | 45 |
| Vs331 | 45 | 48 | 55 | 43 | 45 | 43 | 45 | 45 | 48 | 45 | 46 | 45 | 44 | 40 | 44 | 45 | 46 | 40 | 38 | 38 | 38 |
| Vs342 | 46 | 48 | 53 | 40 | 46 | 44 | 47 | 47 | 49 | 47 | 48 | 47 | 44 | 44 | 45 | 52 | 49 | 44 | 42 | 41 | 41 |
| Vs851 | 46 | 47 | 52 | 41 | 48 | 46 | 48 | 48 | 51 | 49 | 50 | 49 | 44 | 47 | 49 | 54 | 52 | 47 | 44 | 44 | 44 |
| Vs324 | 48 | 48 | 56 | 44 | 50 | 48 | 50 | 50 | 52 | 50 | 50 | 50 | 49 | 47 | 49 | 52 | 52 | 46 | 46 | 48 | 48 |
| Vs328 | 53 | 54 | 61 | 51 | 51 | 49 | 51 | 51 | 53 | 51 | 52 | 51 | 47 | 49 | 53 | 58 | 53 | 48 | 51 | 56 | 56 |
| Vs366 | 48 | 50 | 54 | 49 | 45 | 45 | 50 | 50 | 52 | 51 | 52 | 51 | 50 | 50 | 49 | 58 | 50 | 49 | 50 | 52 | 52 |
| Vs371 | 48 | 50 | 54 | 48 | 46 | 46 | 50 | 50 | 53 | 52 | 53 | 52 | 52 | 50 | 48 | 60 | 51 | 48 | 49 | 50 | 50 |
| Vs360 | 31 | 31 | 41 | 38 | 34 | 37 | 39 | 39 | 40 | 39 | 40 | 39 | 39 | 40 | 42 | 45 | 39 | 38 | 40 | 45 | 45 |
| Vs362 | 30 | 28 | 33 | 37 | 37 | 39 | 39 | 39 | 39 | 38 | 39 | 38 | 42 | 40 | 42 | 46 | 41 | 38 | 41 | 44 | 44 |
| Vs364 | 34 | 34 | 40 | 39 | 38 | 38 | 39 | 39 | 39 | 38 | 39 | 38 | 41 | 42 | 44 | 49 | 45 | 39 | 45 | 47 | 47 |
| Vs373 | 39 | 37 | 40 | 41 | 40 | 42 | 44 | 44 | 44 | 42 | 44 | 42 | 44 | 44 | 48 | 46 | 47 | 39 | 45 | 48 | 48 |
| x Vs365 | 33 | 31 | 38 | 37 | 38 | 38 | 38 | 38 | 38 | 37 | 38 | 37 | 41 | 38 | 44 | 48 | 42 | 37 | 42 | 45 | 45 |
| Vs368 | 36 | 31 | 38 | 38 | 39 | 39 | 39 | 39 | 39 | 38 | 39 | 38 | 42 | 40 | 45 | 48 | 44 | 38 | 42 | 44 | 44 |
| Vs370 | 34 | 32 | 39 | 37 | 38 | 38 | 38 | 38 | 38 | 37 | 38 | 37 | 40 | 41 | 45 | 49 | 44 | 38 | 42 | 46 | 46 |
| Vs369 | 36 | 34 | 40 | 38 | 39 | 39 | 41 | 41 | 41 | 40 | 41 | 40 | 44 | 41 | 45 | 45 | 45 | 38 | 45 | 46 | 46 |
| Vs367 | 36 | 33 | 41 | 38 | 39 | 39 | 41 | 41 | 41 | 40 | 41 | 40 | 45 | 44 | 45 | 49 | 44 | 41 | 44 | 47 | 47 |
| Vs374 | 34 | 37 | 44 | 39 | 39 | 39 | 41 | 41 | 41 | 40 | 41 | 40 | 44 | 38 | 42 | 46 | 40 | 38 | 44 | 42 | 42 |

FIG. 3h

| Vlambda | Vs337 | Vs344 | Vs341 | Vs348 | Vs319 | Vs842 | Vs351 | Vs354 | Vs320 | Vs834 | Vs925 | Vs848 | Vs329 | Vs335 | Vs847 | Vs323 x | Vs339 | Vs837 | Vs923 | Vs843 x | Vs466 | Vs836 |
|---|---|---|---|---|---|---|---|---|---|---|---|---|---|---|---|---|---|---|---|---|---|---|
| Vs336 | 41 | 38 | 45 | 43 | 40 | 40 | 40 | 40 | 40 | 40 | 40 | 43 | 43 | 42 | 42 | 40 | 39 | 38 | 38 | 38 | 39 | 39 |
| Vs846 | 41 | 38 | 45 | 43 | 40 | 40 | 40 | 40 | 40 | 40 | 40 | 43 | 43 | 42 | 42 | 40 | 39 | 38 | 38 | 38 | 39 | 39 |
| Vs358 | 41 | 38 | 46 | 44 | 43 | 43 | 43 | 43 | 43 | 43 | 43 | 45 | 45 | 43 | 43 | 43 | 41 | 40 | 40 | 40 | 42 | 42 |
| Vs325 | 46 | 43 | 49 | 48 | 44 | 44 | 45 | 46 | 49 | 49 | 49 | 51 | 48 | 46 | 46 | 45 | 44 | 42 | 42 | 43 | 43 | 43 |
| Vs331 | 41 | 38 | 47 | 45 | 42 | 42 | 42 | 42 | 44 | 44 | 44 | 46 | 45 | 42 | 42 | 42 | 41 | 40 | 40 | 40 | 41 | 41 |
| Vs342 | 44 | 41 | 47 | 46 | 43 | 43 | 44 | 43 | 43 | 43 | 43 | 44 | 45 | 43 | 43 | 43 | 42 | 41 | 41 | 42 | 44 | 44 |
| Vs851 | 46 | 43 | 50 | 47 | 46 | 46 | 47 | 46 | 45 | 45 | 45 | 46 | 48 | 46 | 46 | 46 | 46 | 46 | 46 | 46 | 47 | 47 |
| Vs324 | 49 | 47 | 50 | 48 | 44 | 44 | 45 | 45 | 47 | 47 | 47 | 48 | 48 | 46 | 46 | 45 | 44 | 41 | 41 | 43 | 43 | 43 |
| Vs328 | 51 | 51 | 52 | 49 | 48 | 48 | 50 | 49 | 50 | 50 | 50 | 50 | 48 | 48 | 48 | 48 | 49 | 48 | 48 | 48 | 47 | 47 |
| Vs366 | 51 | 50 | 52 | 48 | 45 | 45 | 46 | 45 | 48 | 48 | 48 | 49 | 48 | 45 | 45 | 45 | 45 | 46 | 46 | 46 | 46 | 46 |
| Vs371 | 50 | 49 | 51 | 48 | 44 | 44 | 45 | 44 | 48 | 48 | 48 | 49 | 48 | 45 | 45 | 44 | 45 | 46 | 46 | 46 | 45 | 45 |
| Vs360 | 42 | 41 | 40 | 38 | 37 | 37 | 37 | 37 | 39 | 39 | 39 | 41 | 40 | 36 | 36 | 37 | 40 | 39 | 39 | 38 | 38 | 38 |
| Vs362 | 42 | 41 | 42 | 40 | 38 | 38 | 38 | 38 | 41 | 41 | 41 | 44 | 42 | 37 | 37 | 38 | 40 | 39 | 39 | 39 | 38 | 38 |
| Vs364 | 46 | 44 | 41 | 40 | 40 | 40 | 40 | 39 | 39 | 39 | 39 | 41 | 44 | 37 | 37 | 39 | 42 | 42 | 42 | 42 | 41 | 41 |
| Vs373 | 47 | 46 | 46 | 44 | 44 | 44 | 44 | 44 | 44 | 44 | 44 | 46 | 47 | 41 | 41 | 44 | 46 | 44 | 44 | 44 | 42 | 42 |
| x Vs365 | 44 | 41 | 41 | 40 | 38 | 38 | 38 | 39 | 40 | 40 | 40 | 42 | 44 | 38 | 38 | 39 | 41 | 38 | 38 | 39 | 37 | 37 |
| Vs368 | 45 | 42 | 44 | 41 | 39 | 39 | 39 | 40 | 41 | 41 | 41 | 44 | 45 | 39 | 39 | 40 | 42 | 39 | 39 | 40 | 38 | 38 |
| Vs370 | 45 | 42 | 42 | 39 | 39 | 39 | 39 | 39 | 40 | 40 | 40 | 42 | 42 | 38 | 38 | 39 | 42 | 41 | 41 | 40 | 40 | 40 |
| Vs369 | 46 | 44 | 42 | 41 | 41 | 41 | 41 | 40 | 42 | 42 | 42 | 45 | 45 | 39 | 39 | 40 | 42 | 41 | 41 | 41 | 40 | 40 |
| Vs367 | 46 | 45 | 42 | 41 | 40 | 40 | 40 | 40 | 42 | 42 | 42 | 45 | 44 | 39 | 39 | 40 | 44 | 42 | 42 | 42 | 41 | 41 |
| Vs374 | 42 | 38 | 44 | 40 | 39 | 39 | 39 | 39 | 40 | 40 | 40 | 42 | 40 | 37 | 37 | 39 | 42 | 40 | 40 | 40 | 38 | 38 |

FIG. 3i

| Vlambda | Vs316 | Vs840 | Vs332 | Vs849 | Vs340 | Vs355 | Vs318 | Vs465 | Vs835 | Vs927 | Vs343 | Vs346 | Vs357 | Vs850 | Vs338 | Vs317 | Vs924 | Vs922 | Vs333 | Vs921 | Vs841 | Vs321 x |
|---|---|---|---|---|---|---|---|---|---|---|---|---|---|---|---|---|---|---|---|---|---|---|
| Vs361 | 36 | 37 | 37 | 43 | 37 | 41 | 42 | 42 | 42 | 42 | 40 | 42 | 37 | 45 | 39 | 47 | 47 | 45 | 46 | 46 | 46 | 42 |
| Vs363 | 35 | 36 | 36 | 42 | 36 | 40 | 42 | 42 | 42 | 42 | 40 | 41 | 36 | 44 | 39 | 48 | 48 | 46 | 47 | 47 | 47 | 45 |
| Vs372 | 45 | 44 | 45 | 50 | 45 | 46 | 44 | 44 | 44 | 44 | 45 | 50 | 44 | 51 | 47 | 57 | 57 | 55 | 56 | 56 | 56 | 53 |
| Vs359 | 30 | 29 | 29 | 35 | 32 | 36 | 35 | 35 | 35 | 35 | 32 | 35 | 29 | 35 | 28 | 47 | 47 | 45 | 46 | 46 | 46 | 43 |
| Vs330 | 29 | 28 | 28 | 34 | 31 | 31 | 31 | 31 | 31 | 31 | 30 | 31 | 28 | 32 | 23 | 47 | 47 | 46 | 46 | 46 | 46 | 43 |
| Vs352 | 28 | 27 | 27 | 31 | 30 | 31 | 30 | 30 | 30 | 30 | 29 | 30 | 27 | 32 | 23 | 46 | 46 | 45 | 44 | 44 | 44 | 42 |
| Vs349 | 35 | 35 | 35 | 40 | 35 | 32 | 36 | 36 | 36 | 36 | 37 | 37 | 34 | 44 | 32 | 46 | 46 | 46 | 46 | 46 | 46 | 43 |
| Vs838 | 35 | 35 | 35 | 40 | 35 | 32 | 36 | 36 | 36 | 36 | 37 | 37 | 34 | 44 | 32 | 46 | 46 | 46 | 46 | 46 | 46 | 43 |
| Vs468 | 36 | 36 | 36 | 42 | 36 | 35 | 37 | 37 | 37 | 37 | 38 | 38 | 35 | 45 | 33 | 49 | 49 | 48 | 49 | 49 | 49 | 47 |
| Vs844 | 34 | 34 | 34 | 39 | 34 | 32 | 35 | 35 | 35 | 35 | 36 | 36 | 32 | 43 | 31 | 47 | 47 | 47 | 47 | 47 | 47 | 44 |
| Vs456 | 34 | 34 | 34 | 39 | 34 | 32 | 36 | 36 | 36 | 36 | 37 | 37 | 32 | 43 | 31 | 48 | 48 | 48 | 48 | 48 | 48 | 46 |
| Vs457 | 34 | 34 | 34 | 39 | 34 | 32 | 35 | 35 | 35 | 35 | 36 | 36 | 32 | 43 | 31 | 47 | 47 | 47 | 47 | 47 | 47 | 44 |
| Vs326 | 30 | 30 | 28 | 35 | 31 | 33 | 33 | 33 | 33 | 33 | 28 | 32 | 30 | 38 | 26 | 47 | 47 | 46 | 46 | 46 | 46 | 44 |
| Vs350 | 26 | 25 | 25 | 32 | 26 | 32 | 30 | 30 | 30 | 30 | 27 | 30 | 26 | 31 | 21 | 43 | 43 | 42 | 42 | 42 | 42 | 40 |
| Vs353 | 28 | 27 | 27 | 34 | 29 | 32 | 33 | 33 | 33 | 33 | 31 | 33 | 26 | 32 | 20 | 47 | 47 | 45 | 46 | 46 | 46 | 44 |
| Vs322 | 40 | 40 | 38 | 43 | 40 | 42 | 44 | 44 | 44 | 44 | 44 | 47 | 41 | 43 | 37 | 51 | 51 | 50 | 50 | 50 | 50 | 48 |
| Vs345 | 31 | 31 | 30 | 35 | 31 | 35 | 39 | 39 | 39 | 39 | 36 | 39 | 32 | 35 | 24 | 52 | 52 | 51 | 50 | 50 | 50 | 48 |
| Vs356 | 28 | 28 | 27 | 34 | 28 | 34 | 35 | 35 | 35 | 35 | 32 | 35 | 28 | 31 | 23 | 41 | 41 | 40 | 40 | 40 | 40 | 38 |
| Vs327 | 27 | 26 | 26 | 31 | 27 | 32 | 32 | 32 | 32 | 32 | 30 | 32 | 27 | 34 | 24 | 43 | 43 | 42 | 42 | 42 | 42 | 40 |
| Vs334 | 32 | 31 | 32 | 39 | 34 | 38 | 37 | 37 | 37 | 37 | 36 | 38 | 31 | 34 | 28 | 42 | 42 | 40 | 41 | 41 | 41 | 39 |
| Vs845 | 32 | 31 | 32 | 39 | 34 | 38 | 37 | 37 | 37 | 37 | 36 | 38 | 31 | 34 | 28 | 42 | 42 | 40 | 41 | 41 | 41 | 39 |
| Vs337 | 31 | 30 | 29 | 36 | 31 | 36 | 35 | 35 | 35 | 35 | 32 | 35 | 30 | 35 | 24 | 44 | 44 | 44 | 43 | 43 | 43 | 41 |

FIG. 3j

| Vlambda | Vs336 | Vs846 | Vs358 | Vs325 | Vs331 | Vs342 | Vs851 | Vs324 | Vs328 | Vs366 | Vs371 | Vs360 | Vs362 | Vs364 | Vs373 | Vs365 (x) | Vs368 | Vs370 | Vs369 | Vs367 | Vs374 |
|---|---|---|---|---|---|---|---|---|---|---|---|---|---|---|---|---|---|---|---|---|---|
| Vs361 | 42 | 42 | 41 | 43 | 45 | 46 | 46 | 48 | 53 | 48 | 48 | 31 | 30 | 34 | 39 | 33 | 36 | 34 | 36 | 36 | 34 |
| Vs363 | 45 | 45 | 44 | 49 | 48 | 48 | 47 | 48 | 54 | 50 | 50 | 31 | 28 | 34 | 37 | 31 | 31 | 32 | 34 | 33 | 37 |
| Vs372 | 53 | 53 | 50 | 55 | 55 | 53 | 52 | 56 | 61 | 54 | 54 | 41 | 33 | 40 | 40 | 38 | 38 | 39 | 40 | 41 | 44 |
| Vs359 | 43 | 43 | 42 | 50 | 43 | 40 | 41 | 44 | 51 | 49 | 48 | 38 | 37 | 39 | 41 | 37 | 38 | 37 | 38 | 38 | 39 |
| Vs330 | 43 | 43 | 44 | 48 | 45 | 46 | 48 | 50 | 51 | 45 | 46 | 34 | 37 | 38 | 40 | 38 | 39 | 38 | 39 | 39 | 39 |
| Vs352 | 42 | 42 | 43 | 46 | 43 | 44 | 46 | 48 | 49 | 45 | 46 | 37 | 39 | 38 | 42 | 38 | 39 | 38 | 39 | 39 | 39 |
| Vs349 | 43 | 43 | 44 | 47 | 45 | 47 | 48 | 50 | 51 | 50 | 50 | 39 | 39 | 39 | 44 | 38 | 39 | 38 | 41 | 41 | 41 |
| Vs838 | 43 | 43 | 44 | 47 | 45 | 47 | 48 | 50 | 51 | 50 | 50 | 39 | 39 | 39 | 44 | 38 | 39 | 38 | 41 | 41 | 41 |
| Vs468 | 47 | 47 | 48 | 49 | 48 | 49 | 51 | 52 | 53 | 52 | 53 | 40 | 39 | 39 | 44 | 38 | 39 | 38 | 41 | 41 | 41 |
| Vs844 | 44 | 44 | 46 | 48 | 45 | 47 | 49 | 50 | 51 | 51 | 52 | 39 | 38 | 38 | 42 | 37 | 38 | 37 | 40 | 40 | 40 |
| Vs456 | 46 | 46 | 47 | 49 | 46 | 48 | 50 | 50 | 52 | 52 | 53 | 40 | 39 | 39 | 44 | 38 | 39 | 38 | 41 | 41 | 41 |
| Vs457 | 44 | 44 | 46 | 48 | 45 | 47 | 49 | 50 | 51 | 51 | 52 | 39 | 38 | 38 | 42 | 37 | 38 | 37 | 40 | 40 | 40 |
| Vs326 | 44 | 44 | 44 | 51 | 44 | 44 | 44 | 49 | 47 | 50 | 52 | 39 | 42 | 41 | 44 | 41 | 42 | 40 | 44 | 45 | 44 |
| Vs350 | 40 | 40 | 42 | 46 | 40 | 44 | 47 | 47 | 49 | 50 | 50 | 40 | 40 | 42 | 44 | 38 | 40 | 41 | 41 | 44 | 38 |
| Vs353 | 44 | 44 | 44 | 49 | 44 | 45 | 49 | 49 | 53 | 49 | 48 | 42 | 42 | 44 | 48 | 44 | 45 | 45 | 45 | 45 | 42 |
| Vs322 | 48 | 48 | 49 | 52 | 45 | 52 | 54 | 52 | 58 | 58 | 60 | 45 | 46 | 49 | 46 | 48 | 48 | 49 | 45 | 49 | 46 |
| Vs345 | 48 | 48 | 46 | 52 | 46 | 49 | 52 | 52 | 53 | 50 | 51 | 39 | 41 | 45 | 47 | 42 | 44 | 44 | 45 | 44 | 40 |
| Vs356 | 38 | 38 | 40 | 44 | 40 | 44 | 47 | 46 | 48 | 49 | 48 | 38 | 38 | 39 | 39 | 37 | 38 | 38 | 38 | 41 | 38 |
| Vs327 | 40 | 40 | 39 | 46 | 38 | 42 | 44 | 46 | 51 | 50 | 49 | 40 | 41 | 45 | 45 | 42 | 42 | 42 | 45 | 44 | 44 |
| Vs334 | 38 | 38 | 38 | 45 | 38 | 41 | 44 | 48 | 56 | 52 | 50 | 45 | 44 | 47 | 48 | 45 | 44 | 46 | 46 | 47 | 42 |
| Vs845 | 38 | 38 | 38 | 45 | 38 | 41 | 44 | 48 | 56 | 52 | 50 | 45 | 44 | 47 | 48 | 45 | 44 | 46 | 46 | 47 | 42 |
| Vs337 | 41 | 41 | 41 | 46 | 41 | 44 | 46 | 49 | 51 | 51 | 50 | 42 | 42 | 46 | 47 | 44 | 45 | 45 | 46 | 46 | 42 |

FIG. 3k

| Vlambda | Vs361 | Vs363 | Vs372 | Vs359 | Vs330 | Vs352 | Vs349 | Vs838 | Vs468 | Vs844 | Vs456 | Vs457 | Vs326 | Vs350 | Vs353 | Vs322 | Vs345 | Vs356 | Vs327 | Vs334 | Vs845 |
|---|---|---|---|---|---|---|---|---|---|---|---|---|---|---|---|---|---|---|---|---|---|
| Vs361 | 0 | 15 | 39 | 38 | 39 | 38 | 38 | 38 | 40 | 39 | 40 | 39 | 39 | 36 | 34 | 46 | 41 | 36 | 38 | 41 | 41 |
| Vs363 | 15 | 0 | 34 | 36 | 40 | 39 | 39 | 39 | 41 | 40 | 41 | 40 | 38 | 36 | 38 | 48 | 39 | 36 | 37 | 41 | 41 |
| Vs372 | 39 | 34 | 0 | 45 | 48 | 50 | 54 | 54 | 54 | 53 | 54 | 53 | 50 | 49 | 48 | 55 | 49 | 50 | 49 | 48 | 48 |
| Vs359 | 38 | 36 | 45 | 0 | 30 | 27 | 38 | 38 | 39 | 37 | 37 | 37 | 29 | 26 | 27 | 38 | 28 | 24 | 27 | 29 | 29 |
| Vs330 | 39 | 40 | 48 | 30 | 0 | 6 | 20 | 20 | 21 | 19 | 21 | 20 | 28 | 25 | 26 | 34 | 29 | 24 | 28 | 30 | 30 |
| Vs352 | 38 | 39 | 50 | 27 | 6 | 0 | 19 | 19 | 20 | 18 | 20 | 19 | 26 | 22 | 24 | 32 | 26 | 22 | 26 | 28 | 28 |
| Vs349 | 38 | 39 | 54 | 38 | 20 | 19 | 0 | 0 | 3 | 1 | 3 | 2 | 31 | 35 | 34 | 42 | 38 | 33 | 33 | 38 | 38 |
| Vs838 | 38 | 39 | 54 | 38 | 20 | 19 | 0 | 0 | 3 | 1 | 3 | 2 | 31 | 35 | 34 | 42 | 38 | 33 | 33 | 38 | 38 |
| Vs468 | 40 | 41 | 54 | 39 | 21 | 20 | 3 | 3 | 0 | 2 | 4 | 3 | 34 | 36 | 35 | 42 | 39 | 34 | 34 | 39 | 39 |
| Vs844 | 39 | 40 | 53 | 37 | 19 | 18 | 1 | 1 | 2 | 0 | 2 | 1 | 31 | 34 | 32 | 40 | 37 | 32 | 32 | 37 | 37 |
| Vs456 | 40 | 41 | 54 | 37 | 21 | 20 | 3 | 3 | 4 | 2 | 0 | 1 | 32 | 34 | 32 | 40 | 37 | 32 | 32 | 37 | 37 |
| Vs457 | 39 | 40 | 53 | 37 | 20 | 19 | 2 | 2 | 3 | 1 | 1 | 0 | 31 | 34 | 32 | 40 | 37 | 32 | 32 | 37 | 37 |
| Vs326 | 39 | 38 | 50 | 29 | 28 | 26 | 31 | 31 | 34 | 31 | 32 | 31 | 0 | 17 | 19 | 33 | 24 | 20 | 21 | 28 | 28 |
| Vs350 | 36 | 36 | 49 | 26 | 25 | 22 | 35 | 35 | 36 | 34 | 34 | 34 | 17 | 0 | 11 | 30 | 17 | 12 | 17 | 17 | 17 |
| Vs353 | 34 | 38 | 48 | 27 | 26 | 24 | 34 | 34 | 35 | 32 | 32 | 32 | 19 | 11 | 0 | 32 | 18 | 17 | 18 | 19 | 19 |
| Vs322 | 46 | 48 | 55 | 38 | 34 | 32 | 42 | 42 | 42 | 40 | 40 | 40 | 33 | 30 | 32 | 0 | 30 | 25 | 32 | 30 | 30 |
| Vs345 | 41 | 39 | 49 | 28 | 29 | 26 | 38 | 38 | 39 | 37 | 37 | 37 | 24 | 17 | 18 | 30 | 0 | 17 | 20 | 22 | 22 |
| Vs356 | 36 | 36 | 50 | 24 | 24 | 22 | 33 | 33 | 34 | 32 | 32 | 32 | 20 | 12 | 17 | 25 | 17 | 0 | 14 | 14 | 14 |
| Vs327 | 38 | 37 | 49 | 27 | 28 | 26 | 33 | 33 | 34 | 32 | 32 | 32 | 21 | 17 | 18 | 32 | 20 | 14 | 0 | 14 | 14 |
| Vs334 | 41 | 41 | 48 | 29 | 30 | 28 | 38 | 38 | 39 | 37 | 37 | 37 | 28 | 17 | 19 | 30 | 22 | 14 | 14 | 0 | 0 |
| Vs845 | 41 | 41 | 48 | 29 | 30 | 28 | 38 | 38 | 39 | 37 | 37 | 37 | 28 | 17 | 19 | 30 | 22 | 14 | 14 | 0 | 0 |
| Vs337 | 39 | 39 | 50 | 26 | 27 | 24 | 37 | 37 | 38 | 36 | 36 | 36 | 21 | 13 | 17 | 31 | 19 | 11 | 13 | 13 | 13 |

FIG. 3L

| Vlambda | Vs337 | Vs344 | Vs341 | Vs348 | Vs319 | Vs842 | Vs351 | Vs354 | Vs320 | Vs834 | Vs925 | Vs848 | Vs329 | Vs335 | Vs847 | Vs323 (x) | Vs339 | Vs837 | Vs923 | Vs843 (x) | Vs466 | Vs836 |
|---|---|---|---|---|---|---|---|---|---|---|---|---|---|---|---|---|---|---|---|---|---|---|
| Vs361 | 39 | 38 | 36 | 34 | 34 | 34 | 33 | 33 | 37 | 37 | 37 | 38 | 40 | 33 | 33 | 33 | 36 | 36 | 36 | 36 | 34 | 34 |
| Vs363 | 39 | 38 | 36 | 33 | 36 | 36 | 34 | 36 | 38 | 38 | 38 | 39 | 42 | 36 | 36 | 36 | 37 | 36 | 36 | 36 | 36 | 36 |
| Vs372 | 50 | 50 | 53 | 52 | 47 | 47 | 49 | 47 | 49 | 49 | 49 | 50 | 54 | 47 | 47 | 47 | 48 | 48 | 48 | 48 | 48 | 48 |
| Vs359 | 26 | 26 | 29 | 27 | 22 | 22 | 25 | 22 | 31 | 31 | 31 | 32 | 30 | 24 | 24 | 24 | 28 | 24 | 24 | 26 | 25 | 25 |
| Vs330 | 27 | 23 | 26 | 21 | 19 | 19 | 21 | 19 | 24 | 24 | 24 | 26 | 26 | 19 | 19 | 19 | 23 | 23 | 23 | 24 | 22 | 22 |
| Vs352 | 24 | 21 | 24 | 19 | 17 | 17 | 19 | 17 | 24 | 24 | 24 | 26 | 25 | 17 | 17 | 17 | 21 | 21 | 21 | 22 | 20 | 20 |
| Vs349 | 37 | 34 | 35 | 31 | 30 | 30 | 31 | 30 | 35 | 35 | 35 | 37 | 35 | 28 | 28 | 29 | 29 | 32 | 32 | 33 | 31 | 31 |
| Vs838 | 37 | 34 | 35 | 31 | 30 | 30 | 31 | 30 | 35 | 35 | 35 | 37 | 35 | 28 | 28 | 29 | 29 | 32 | 32 | 33 | 31 | 31 |
| Vs468 | 38 | 36 | 36 | 32 | 31 | 31 | 34 | 31 | 36 | 36 | 36 | 38 | 36 | 29 | 29 | 30 | 30 | 33 | 33 | 34 | 32 | 32 |
| Vs844 | 36 | 33 | 34 | 30 | 29 | 29 | 31 | 29 | 34 | 34 | 34 | 36 | 34 | 27 | 27 | 28 | 28 | 31 | 31 | 32 | 30 | 30 |
| Vs456 | 36 | 33 | 34 | 30 | 29 | 29 | 31 | 29 | 35 | 35 | 35 | 37 | 34 | 28 | 28 | 28 | 28 | 31 | 31 | 32 | 30 | 30 |
| Vs457 | 36 | 33 | 34 | 30 | 29 | 29 | 31 | 29 | 34 | 34 | 34 | 36 | 34 | 27 | 27 | 28 | 28 | 31 | 31 | 32 | 30 | 30 |
| Vs326 | 21 | 22 | 22 | 19 | 20 | 20 | 19 | 21 | 29 | 29 | 29 | 28 | 29 | 19 | 19 | 21 | 22 | 25 | 25 | 24 | 22 | 22 |
| Vs350 | 13 | 11 | 11 | 10 | 11 | 11 | 11 | 12 | 25 | 25 | 25 | 26 | 20 | 16 | 16 | 12 | 16 | 13 | 13 | 12 | 11 | 11 |
| Vs353 | 17 | 16 | 15 | 15 | 12 | 12 | 12 | 12 | 26 | 26 | 26 | 27 | 21 | 17 | 17 | 12 | 13 | 17 | 17 | 16 | 15 | 15 |
| Vs322 | 31 | 30 | 30 | 26 | 27 | 27 | 28 | 28 | 36 | 36 | 36 | 38 | 37 | 28 | 28 | 28 | 32 | 31 | 31 | 30 | 27 | 27 |
| Vs345 | 19 | 18 | 20 | 19 | 17 | 17 | 18 | 18 | 29 | 29 | 29 | 30 | 25 | 19 | 19 | 18 | 20 | 20 | 20 | 19 | 18 | 18 |
| Vs356 | 11 | 10 | 15 | 11 | 10 | 10 | 11 | 11 | 21 | 21 | 21 | 22 | 19 | 15 | 15 | 11 | 12 | 10 | 10 | 9 | 10 | 10 |
| Vs327 | 13 | 13 | 22 | 20 | 17 | 17 | 18 | 17 | 25 | 25 | 25 | 26 | 22 | 20 | 20 | 18 | 17 | 17 | 17 | 17 | 18 | 18 |
| Vs334 | 13 | 11 | 20 | 19 | 16 | 16 | 17 | 17 | 26 | 26 | 26 | 27 | 21 | 19 | 19 | 16 | 17 | 16 | 16 | 14 | 16 | 16 |
| Vs845 | 13 | 11 | 20 | 19 | 16 | 16 | 17 | 17 | 26 | 26 | 26 | 27 | 21 | 19 | 19 | 16 | 17 | 16 | 16 | 14 | 16 | 16 |
| Vs337 | 0 | 7 | 18 | 16 | 11 | 11 | 13 | 13 | 22 | 22 | 22 | 24 | 20 | 16 | 16 | 12 | 12 | 11 | 11 | 10 | 12 | 12 |

FIG. 3m

| Vlambda | Vs316 | Vs840 | Vs332 | Vs849 | Vs340 | Vs355 | Vs318 | Vs465 | Vs835 | Vs927 | Vs343 | Vs346 | Vs357 | Vs850 | Vs338 | Vs317 | Vs924 | Vs922 | Vs333 | Vs921 | Vs841 | Vs321 (x) |
|---|---|---|---|---|---|---|---|---|---|---|---|---|---|---|---|---|---|---|---|---|---|---|
| Vs344 | 29 | 28 | 28 | 32 | 30 | 35 | 34 | 34 | 34 | 34 | 31 | 34 | 28 | 31 | 23 | 42 | 42 | 41 | 41 | 41 | 41 | 39 |
| Vs341 | 28 | 27 | 28 | 35 | 30 | 34 | 34 | 34 | 34 | 34 | 33 | 35 | 30 | 34 | 24 | 47 | 47 | 46 | 46 | 46 | 46 | 45 |
| Vs348 | 25 | 24 | 24 | 31 | 24 | 31 | 31 | 31 | 31 | 31 | 30 | 31 | 25 | 30 | 20 | 45 | 45 | 44 | 44 | 44 | 44 | 43 |
| Vs319 | 25 | 24 | 24 | 31 | 24 | 31 | 30 | 30 | 30 | 30 | 27 | 30 | 22 | 26 | 18 | 44 | 44 | 43 | 43 | 43 | 43 | 40 |
| Vs842 | 25 | 24 | 24 | 31 | 24 | 31 | 30 | 30 | 30 | 30 | 27 | 30 | 22 | 26 | 18 | 44 | 44 | 43 | 43 | 43 | 43 | 40 |
| Vs351 | 27 | 26 | 26 | 33 | 26 | 31 | 32 | 32 | 32 | 32 | 30 | 32 | 24 | 28 | 20 | 44 | 44 | 43 | 43 | 43 | 43 | 40 |
| Vs354 | 25 | 24 | 24 | 31 | 24 | 31 | 28 | 28 | 28 | 28 | 26 | 28 | 23 | 27 | 16 | 44 | 44 | 43 | 43 | 43 | 43 | 40 |
| Vs320 | 33 | 32 | 33 | 36 | 34 | 40 | 35 | 35 | 35 | 35 | 34 | 35 | 34 | 36 | 26 | 44 | 44 | 43 | 43 | 43 | 43 | 39 |
| Vs834 | 33 | 32 | 33 | 36 | 34 | 40 | 35 | 35 | 35 | 35 | 34 | 35 | 34 | 36 | 26 | 44 | 44 | 43 | 43 | 43 | 43 | 39 |
| Vs925 | 33 | 32 | 33 | 36 | 34 | 40 | 35 | 35 | 35 | 35 | 34 | 35 | 34 | 36 | 26 | 44 | 44 | 43 | 43 | 43 | 43 | 39 |
| Vs848 | 33 | 34 | 35 | 39 | 37 | 41 | 36 | 36 | 36 | 36 | 33 | 36 | 35 | 38 | 28 | 46 | 46 | 45 | 45 | 45 | 45 | 42 |
| Vs329 | 32 | 31 | 32 | 38 | 31 | 36 | 35 | 35 | 35 | 35 | 33 | 34 | 31 | 34 | 24 | 46 | 46 | 45 | 45 | 45 | 45 | 43 |
| Vs335 | 26 | 25 | 26 | 33 | 28 | 32 | 30 | 30 | 30 | 30 | 27 | 30 | 27 | 32 | 19 | 45 | 45 | 44 | 44 | 44 | 44 | 42 |
| Vs847 | 26 | 25 | 26 | 33 | 28 | 32 | 30 | 30 | 30 | 30 | 27 | 30 | 27 | 32 | 19 | 45 | 45 | 44 | 44 | 44 | 44 | 42 |
| Vs323 (x) | 25 | 24 | 25 | 32 | 25 | 31 | 30 | 30 | 30 | 30 | 27 | 30 | 24 | 28 | 18 | 44 | 44 | 43 | 43 | 43 | 43 | 40 |
| Vs339 | 27 | 26 | 27 | 34 | 28 | 29 | 32 | 32 | 32 | 32 | 30 | 32 | 27 | 32 | 20 | 42 | 42 | 41 | 41 | 41 | 41 | 39 |
| Vs837 | 27 | 26 | 27 | 34 | 28 | 32 | 34 | 34 | 34 | 34 | 31 | 34 | 26 | 30 | 21 | 41 | 41 | 40 | 40 | 40 | 40 | 38 |
| Vs923 | 27 | 26 | 27 | 34 | 28 | 32 | 34 | 34 | 34 | 34 | 31 | 34 | 26 | 30 | 21 | 41 | 41 | 40 | 40 | 40 | 40 | 38 |
| Vs843 (x) | 27 | 26 | 27 | 34 | 28 | 32 | 34 | 34 | 34 | 34 | 31 | 34 | 27 | 31 | 21 | 41 | 41 | 40 | 40 | 40 | 40 | 37 |
| Vs466 | 25 | 24 | 25 | 32 | 25 | 31 | 32 | 32 | 32 | 32 | 30 | 32 | 24 | 28 | 20 | 43 | 43 | 42 | 42 | 42 | 42 | 39 |
| Vs836 | 25 | 24 | 25 | 32 | 25 | 31 | 32 | 32 | 32 | 32 | 30 | 32 | 24 | 28 | 20 | 43 | 43 | 42 | 42 | 42 | 42 | 39 |

FIG. 3n

| Vlambda | Vs336 | Vs846 | Vs358 | Vs325 | Vs331 | Vs342 | Vs851 | Vs324 | Vs328 | Vs366 | Vs371 | Vs360 | Vs362 | Vs364 | Vs373 | Vs365 (x) | Vs368 | Vs370 | Vs369 | Vs367 | Vs374 |
|---|---|---|---|---|---|---|---|---|---|---|---|---|---|---|---|---|---|---|---|---|---|
| Vs344 | 38 | 38 | 38 | 43 | 38 | 41 | 43 | 47 | 51 | 50 | 49 | 41 | 41 | 44 | 46 | 41 | 42 | 42 | 44 | 45 | 38 |
| Vs341 | 45 | 45 | 46 | 49 | 47 | 47 | 50 | 50 | 52 | 52 | 51 | 40 | 42 | 41 | 46 | 41 | 44 | 42 | 42 | 42 | 44 |
| Vs348 | 43 | 43 | 44 | 48 | 45 | 46 | 47 | 48 | 49 | 48 | 48 | 38 | 40 | 40 | 44 | 40 | 41 | 39 | 41 | 41 | 40 |
| Vs319 | 40 | 40 | 43 | 44 | 42 | 43 | 46 | 44 | 48 | 45 | 44 | 37 | 38 | 40 | 44 | 38 | 39 | 39 | 41 | 40 | 39 |
| Vs842 | 40 | 40 | 43 | 44 | 42 | 43 | 46 | 44 | 48 | 45 | 44 | 37 | 38 | 40 | 44 | 38 | 39 | 39 | 41 | 40 | 39 |
| Vs351 | 40 | 40 | 43 | 45 | 42 | 44 | 47 | 45 | 50 | 46 | 45 | 37 | 38 | 40 | 44 | 38 | 39 | 39 | 41 | 40 | 39 |
| Vs354 | 40 | 40 | 43 | 46 | 42 | 43 | 46 | 45 | 49 | 45 | 44 | 37 | 38 | 39 | 44 | 39 | 40 | 39 | 40 | 40 | 39 |
| Vs320 | 40 | 40 | 43 | 49 | 44 | 43 | 45 | 47 | 50 | 48 | 48 | 39 | 41 | 39 | 44 | 40 | 41 | 40 | 42 | 42 | 40 |
| Vs834 | 40 | 40 | 43 | 49 | 44 | 43 | 45 | 47 | 50 | 48 | 48 | 39 | 41 | 39 | 44 | 40 | 41 | 40 | 42 | 42 | 40 |
| Vs925 | 40 | 40 | 43 | 49 | 44 | 43 | 45 | 47 | 50 | 48 | 48 | 39 | 41 | 39 | 44 | 40 | 41 | 40 | 42 | 42 | 40 |
| Vs848 | 43 | 43 | 45 | 51 | 46 | 44 | 46 | 48 | 50 | 49 | 49 | 41 | 44 | 41 | 46 | 42 | 44 | 42 | 45 | 45 | 42 |
| Vs329 | 43 | 43 | 45 | 48 | 45 | 45 | 48 | 48 | 48 | 48 | 48 | 40 | 42 | 44 | 47 | 44 | 45 | 42 | 45 | 44 | 40 |
| Vs335 | 42 | 42 | 43 | 46 | 42 | 43 | 46 | 46 | 48 | 45 | 45 | 36 | 37 | 37 | 41 | 38 | 39 | 38 | 39 | 39 | 37 |
| Vs847 | 42 | 42 | 43 | 46 | 42 | 43 | 46 | 46 | 48 | 45 | 45 | 36 | 37 | 37 | 41 | 38 | 39 | 38 | 39 | 39 | 37 |
| x Vs323 | 40 | 40 | 43 | 45 | 42 | 43 | 46 | 45 | 48 | 45 | 44 | 37 | 38 | 39 | 44 | 39 | 40 | 39 | 40 | 40 | 39 |
| Vs339 | 39 | 39 | 41 | 44 | 41 | 42 | 46 | 44 | 49 | 45 | 45 | 40 | 40 | 42 | 46 | 41 | 42 | 42 | 42 | 44 | 42 |
| Vs837 | 38 | 38 | 40 | 42 | 40 | 41 | 46 | 41 | 48 | 46 | 46 | 39 | 39 | 42 | 44 | 38 | 39 | 41 | 41 | 42 | 40 |
| Vs923 | 38 | 38 | 40 | 42 | 40 | 41 | 46 | 41 | 48 | 46 | 46 | 39 | 39 | 42 | 44 | 38 | 39 | 41 | 41 | 42 | 40 |
| x Vs843 | 38 | 38 | 40 | 43 | 40 | 42 | 46 | 43 | 48 | 46 | 46 | 38 | 39 | 42 | 44 | 39 | 40 | 40 | 41 | 42 | 40 |
| Vs466 | 39 | 39 | 42 | 43 | 41 | 44 | 47 | 43 | 47 | 46 | 45 | 38 | 38 | 41 | 42 | 37 | 38 | 40 | 40 | 41 | 38 |
| Vs836 | 39 | 39 | 42 | 43 | 41 | 44 | 47 | 43 | 47 | 46 | 45 | 38 | 38 | 41 | 42 | 37 | 38 | 40 | 40 | 41 | 38 |

FIG. 3o

| Vlambda | Vs361 | Vs363 | Vs372 | Vs359 | Vs330 | Vs352 | Vs349 | Vs838 | Vs468 | Vs844 | Vs456 | Vs457 | Vs326 | Vs350 | Vs353 | Vs322 | Vs345 | Vs356 | Vs327 | Vs334 | Vs845 |
|---|---|---|---|---|---|---|---|---|---|---|---|---|---|---|---|---|---|---|---|---|---|
| Vs344 | 38 | 38 | 50 | 26 | 23 | 21 | 34 | 34 | 36 | 33 | 33 | 33 | 22 | 11 | 16 | 30 | 18 | 10 | 13 | 11 | 11 |
| Vs341 | 36 | 36 | 53 | 29 | 26 | 24 | 35 | 35 | 36 | 34 | 34 | 34 | 22 | 11 | 15 | 30 | 20 | 15 | 22 | 20 | 20 |
| Vs348 | 34 | 33 | 52 | 27 | 21 | 19 | 31 | 31 | 32 | 30 | 30 | 30 | 19 | 10 | 15 | 26 | 19 | 11 | 20 | 19 | 19 |
| Vs319 | 34 | 36 | 47 | 22 | 19 | 17 | 30 | 30 | 31 | 29 | 29 | 29 | 20 | 11 | 12 | 27 | 17 | 10 | 17 | 16 | 16 |
| Vs842 | 34 | 36 | 47 | 22 | 19 | 17 | 30 | 30 | 31 | 29 | 29 | 29 | 20 | 11 | 12 | 27 | 17 | 10 | 17 | 16 | 16 |
| Vs351 | 33 | 34 | 49 | 25 | 21 | 19 | 31 | 31 | 34 | 31 | 31 | 31 | 19 | 11 | 12 | 28 | 18 | 11 | 18 | 17 | 17 |
| Vs354 | 33 | 36 | 47 | 22 | 19 | 17 | 30 | 30 | 31 | 29 | 29 | 29 | 21 | 12 | 12 | 28 | 18 | 11 | 17 | 17 | 17 |
| Vs320 | 37 | 38 | 49 | 31 | 24 | 24 | 35 | 35 | 36 | 34 | 35 | 34 | 29 | 25 | 26 | 36 | 29 | 21 | 25 | 26 | 26 |
| Vs834 | 37 | 38 | 49 | 31 | 24 | 24 | 35 | 35 | 36 | 34 | 35 | 34 | 29 | 25 | 26 | 36 | 29 | 21 | 25 | 26 | 26 |
| Vs925 | 37 | 38 | 49 | 31 | 24 | 24 | 35 | 35 | 36 | 34 | 35 | 34 | 29 | 25 | 26 | 36 | 29 | 21 | 25 | 26 | 26 |
| Vs848 | 38 | 39 | 50 | 32 | 26 | 26 | 37 | 37 | 38 | 36 | 37 | 36 | 28 | 26 | 27 | 38 | 30 | 22 | 26 | 27 | 27 |
| Vs329 | 40 | 42 | 54 | 30 | 26 | 25 | 35 | 35 | 36 | 34 | 34 | 34 | 29 | 20 | 21 | 37 | 25 | 19 | 22 | 21 | 21 |
| Vs335 | 33 | 36 | 47 | 24 | 19 | 17 | 28 | 28 | 29 | 27 | 28 | 27 | 19 | 16 | 17 | 28 | 19 | 15 | 20 | 19 | 19 |
| Vs847 | 33 | 36 | 47 | 24 | 19 | 17 | 28 | 28 | 29 | 27 | 28 | 27 | 19 | 16 | 17 | 28 | 19 | 15 | 20 | 19 | 19 |
| x Vs323 | 33 | 36 | 47 | 24 | 19 | 17 | 29 | 29 | 30 | 28 | 28 | 28 | 21 | 12 | 12 | 28 | 18 | 11 | 18 | 16 | 16 |
| Vs339 | 36 | 37 | 48 | 28 | 23 | 21 | 29 | 29 | 30 | 28 | 28 | 28 | 22 | 16 | 13 | 32 | 20 | 12 | 17 | 17 | 17 |
| Vs837 | 36 | 36 | 48 | 24 | 23 | 21 | 32 | 32 | 33 | 31 | 31 | 31 | 25 | 13 | 17 | 31 | 20 | 10 | 17 | 16 | 16 |
| Vs923 | 36 | 36 | 48 | 24 | 23 | 21 | 32 | 32 | 33 | 31 | 31 | 31 | 25 | 13 | 17 | 31 | 20 | 10 | 17 | 16 | 16 |
| x Vs843 | 36 | 36 | 48 | 26 | 24 | 22 | 33 | 33 | 34 | 32 | 32 | 32 | 24 | 12 | 16 | 30 | 19 | 9 | 17 | 14 | 14 |
| Vs466 | 34 | 36 | 48 | 25 | 22 | 20 | 31 | 31 | 32 | 30 | 30 | 30 | 22 | 11 | 15 | 27 | 18 | 10 | 18 | 16 | 16 |
| Vs836 | 34 | 36 | 48 | 25 | 22 | 20 | 31 | 31 | 32 | 30 | 30 | 30 | 22 | 11 | 15 | 27 | 18 | 10 | 18 | 16 | 16 |

FIG. 3p

| Vlambda | Vs337 | Vs344 | Vs341 | Vs348 | Vs319 | Vs842 | Vs351 | Vs354 | Vs320 | Vs834 | Vs925 | Vs848 | Vs329 | Vs335 | Vs847 | Vs323 | Vs339 | Vs837 | Vs923 | Vs843 | Vs466 | Vs836 |
|---|---|---|---|---|---|---|---|---|---|---|---|---|---|---|---|---|---|---|---|---|---|---|
| Vs344 | 7 | 0 | 16 | 13 | 10 | 10 | 12 | 12 | 21 | 21 | 21 | 22 | 19 | 15 | 15 | 11 | 11 | 10 | 10 | 9 | 11 | 11 |
| Vs341 | 18 | 16 | 0 | 7 | 11 | 11 | 11 | 12 | 20 | 20 | 20 | 21 | 18 | 13 | 13 | 10 | 15 | 12 | 12 | 11 | 10 | 10 |
| Vs348 | 16 | 13 | 7 | 0 | 8 | 8 | 8 | 9 | 20 | 20 | 20 | 21 | 17 | 12 | 12 | 9 | 13 | 12 | 12 | 11 | 9 | 9 |
| Vs319 | 11 | 10 | 11 | 8 | 0 | 0 | 3 | 3 | 16 | 16 | 16 | 17 | 11 | 7 | 7 | 2 | 9 | 7 | 7 | 7 | 3 | 3 |
| Vs842 | 11 | 10 | 11 | 8 | 0 | 0 | 3 | 3 | 16 | 16 | 16 | 17 | 11 | 7 | 7 | 2 | 9 | 7 | 7 | 7 | 3 | 3 |
| Vs351 | 13 | 12 | 11 | 8 | 3 | 3 | 0 | 6 | 19 | 19 | 19 | 20 | 15 | 10 | 10 | 6 | 12 | 10 | 10 | 10 | 7 | 7 |
| Vs354 | 13 | 12 | 12 | 9 | 3 | 3 | 6 | 0 | 15 | 15 | 15 | 16 | 12 | 8 | 8 | 3 | 10 | 9 | 9 | 9 | 7 | 7 |
| Vs320 | 22 | 21 | 20 | 20 | 16 | 16 | 19 | 15 | 0 | 0 | 0 | 3 | 18 | 13 | 13 | 13 | 17 | 15 | 15 | 15 | 15 | 15 |
| Vs834 | 22 | 21 | 20 | 20 | 16 | 16 | 19 | 15 | 0 | 0 | 0 | 3 | 18 | 13 | 13 | 13 | 17 | 15 | 15 | 15 | 15 | 15 |
| Vs925 | 22 | 21 | 20 | 20 | 16 | 16 | 19 | 15 | 0 | 0 | 0 | 3 | 18 | 13 | 13 | 13 | 17 | 15 | 15 | 15 | 15 | 15 |
| Vs848 | 24 | 22 | 21 | 21 | 17 | 17 | 20 | 16 | 3 | 3 | 3 | 0 | 19 | 15 | 15 | 15 | 18 | 16 | 16 | 16 | 16 | 16 |
| Vs329 | 20 | 19 | 18 | 17 | 11 | 11 | 15 | 12 | 18 | 18 | 18 | 19 | 0 | 11 | 11 | 9 | 16 | 15 | 15 | 13 | 11 | 11 |
| Vs335 | 16 | 15 | 13 | 12 | 7 | 7 | 10 | 8 | 13 | 13 | 13 | 15 | 11 | 0 | 0 | 4 | 11 | 10 | 10 | 9 | 7 | 7 |
| Vs847 | 16 | 15 | 13 | 12 | 7 | 7 | 10 | 8 | 13 | 13 | 13 | 15 | 11 | 0 | 0 | 4 | 11 | 10 | 10 | 9 | 7 | 7 |
| x Vs323 | 12 | 11 | 10 | 9 | 2 | 2 | 6 | 3 | 13 | 13 | 13 | 15 | 9 | 4 | 4 | 0 | 8 | 7 | 7 | 6 | 3 | 3 |
| Vs339 | 12 | 11 | 15 | 13 | 9 | 9 | 12 | 10 | 17 | 17 | 17 | 18 | 16 | 11 | 11 | 8 | 0 | 7 | 7 | 6 | 8 | 8 |
| Vs837 | 11 | 10 | 12 | 12 | 7 | 7 | 10 | 9 | 15 | 15 | 15 | 16 | 15 | 10 | 10 | 7 | 7 | 0 | 0 | 2 | 3 | 3 |
| Vs923 | 11 | 10 | 12 | 12 | 7 | 7 | 10 | 9 | 15 | 15 | 15 | 16 | 15 | 10 | 10 | 7 | 7 | 0 | 0 | 2 | 3 | 3 |
| x Vs843 | 10 | 9 | 11 | 11 | 7 | 7 | 10 | 9 | 15 | 15 | 15 | 16 | 13 | 9 | 9 | 6 | 6 | 2 | 2 | 0 | 3 | 3 |
| Vs466 | 12 | 11 | 10 | 9 | 3 | 3 | 7 | 7 | 15 | 15 | 15 | 16 | 11 | 7 | 7 | 3 | 8 | 3 | 3 | 3 | 0 | 0 |
| Vs836 | 12 | 11 | 10 | 9 | 3 | 3 | 7 | 7 | 15 | 15 | 15 | 16 | 11 | 7 | 7 | 3 | 8 | 3 | 3 | 3 | 0 | 0 |

CANINE ANTIBODY LIBRARIES

This patent application is a continuation of U.S. patent application Ser. No. 16/624,514, filed Dec. 19, 2019, which is the National Stage of International Application No. PCT/EP2018/066563 filed Jun. 21, 2018, which claims the benefit of priority from EP 17177322.9 filed Jun. 22, 2017, each of which is incorporated herein by reference in its entirety.

FIELD OF THE INVENTION

The present invention relates to and provides canine libraries, such as synthetic antibody libraries which are suitable for selection of fully canine antibodies. The invention also relates to synthetic nucleic acid sequences which encode individual or collections of canine antibodies, i.e. nucleic acid sequences encoding canine antibody libraries. Methods for generating and using such libraries are provided. In particular, the invention relates to the preparation of a library of fully canine antibodies by the use of synthetic germline sequences to generate a library of fully canine antibodies having specific biophysical properties.

BACKGROUND OF THE INVENTION

Immunoglobulins, such as antibodies, are of continued and increasing interest for the pharmaceutical industry. Since 2000, the therapeutic market for monoclonal antibodies has grown exponentially and in 2007, eight of the 20 best-selling biotechnology drugs in the U.S. were therapeutic monoclonal antibodies each having worldwide annual sales of more than 5 billion USD. Therapeutic antibodies improve the treatment of many diseases and increasingly improve the quality of lives of patients even with the most severe and challenging diseases.

Companion animals such as dogs develop similar diseases than humans underlying similar or even the same biological mechanisms and disorders. As an example, lymphoma is the most common neoplasm of the canine hemolymphatic system. It represents approximately 4.5% of all canine neoplasms and 15% of all malignant neoplasms. Canine lymphoma (CL) is usually rapidly fatal, resulting in death within one to three months of diagnosis (Squire et al, 1973; Steven E. Crow, 2008). Furthermore, it is estimated that one in five adult dogs in the USA has arthritis and dogs have been used as models of human joint disease, e.g. for osteoarthritis, anterior cruciate ligament disruption and meniscal damage.

Therefore therapeutic monoclonal antibodies not only provide a highly promising drug class for the treatment of humans but also for the treatment of dogs.

There are already attempts to use antibodies for the treatment of dogs. Even prior to the U.S. Food and Drug Administration's (FDA) approval of the first monoclonal antibody for the treatment of human cancer, in 1992 the United States Department of Agriculture (USDA) had approved the monoclonal antibody MAb 231 for use in dogs with lymphoma. MAb 231 is a murine-derived monoclonal antibody which was generated using the hybridoma technology developed by Kohler and Milstein in 1975 and specifically binds the canine lymphoma cell line 17-71 (see e.g.: U.S. Pat. No. 5,169,775A). MAb 231 was demonstrated to bind tumor cells and not normal cells and was of the therapeutically desirable murine isotype IgG2a that mediates cell cytotoxicity.

Meanwhile methods to "caninise" antibodies and therefore mimic canine antibodies are in use. For example, Gearing et al. (BMC Veterinary Research 2013, 9:226) discloses the generation of a "fully caninised" anti-NGF monoclonal antibody by using an algorithm that is based on expressed canine immunoglobulin sequences to convert an existing rat anti-NGF monoclonal antibody into a recombinant caninised anti-NGF mAb.

To the inventors' knowledge, neither a fully synthetic canine antibody library nor any other reliable canine antibody library with a predefined and diverse VHNL composition previously has been disclosed. Within the present invention, rational analysis of the naturally occurring canine antibody sequences and sophisticated design of the libraries, led to the first fully synthetic canine antibody libraries that are broadly useful for biomedical research. The members of the library were also selected for advantageous properties, such as a high monomeric content and a high thermal stability.

As for the methods of screening the synthetic canine antibody libraries, display on phage, E. coli, yeast, or the like can be used. In the preferred phage display, for example, antibodies are presented as a fusion polypeptide on a bacteriophage surface protein. The antibody-displayed phage particles are brought into contact with a target molecule of interest (for example immobilized on a solid phase (e.g.: microtiter plate, magnetic bead etc.) or in solution), to thereby conduct an affinity selection. Phages expressing antibodies having affinity to the target molecule are selected, phages with antibodies that do not bind the target molecule are washed away during the selections round, commonly referred to as "(bio)-panning". In phage display, the antibody presented on the selected phages corresponds one-to-one to the gene coding the same, and therefore, the antibody of interest can be easily identified. Further, the gene encoding the antibody can be easily amplified, and therefore, phage display is widely used as method for screening and isolating antibodies from large libraries.

SUMMARY OF THE INVENTION

Since immunoglobulin sequences encoded by canine germline sequences are expected not to be immunogenic in dogs, we searched for germline immunoglobulin sequences representing classes of the most abundant canine antibodies.

According to Bao et al. (Veterinary Immunology and Immunopathology 137 (2010) 64-75) the canine antibody VH gene repertoire includes 80 VH segments (of which 41 are functional and 39 are pseudogenes), 6 DH and 3 JH segments. The VH gene is formed by the combination of the different V, D and J gene segments from said VH gene repertoire and is joined by the addition or deletion of short coding sequences at the VD and VJ joints to increase the diversity of the antibodies. The VDJ recombination which occurs prior to the germinal center entry is not completely random but specific VH genes are used more frequently than others.

In canine the 1-VH62 (Vs624) and the 1-VH44 (Vs635) were identified to be the most frequent used VH segments in splenic B cells, with an occurrence of 27% for 1-VH62 and 23.4% for 1-VH44 (Bao et al. 2010). All remaining VH were used with less than 11% frequency. In canine three VH families (VH1, VH2 and VH3) exist of which the majority belong to the VH1 family, while 2-VH51, 2-VH64 and 2-VH66 belong to the VH2 family and 3-VH80 represents the only VH3 family member.

The antibody light chains in canine are also based on variable regions encoded by V and J gene segments and a constant region encoded by kappa and lambda genes. *Canis familiaris* immunoglobulin lambda sequences can be grouped in four VL lambda chain families [V-I (GenBankAccession no. XM845300), V-II (GenBank Accession no. XM543519), V-III (GenBank Accession no. XM844188) and V-IV (GenBank Accession no. XM844237)] *C. familiaris* immunoglobulin kappa sequences, also can be grouped in four VL kappa chain families V-I (Gen Bank Accession no. XM849621), V-II (Gen Bank Accession no. XM844874), V-III (Gen BankAccession no. XM849629) and V-IV (Gen Bank Accession no. XM849668) sequences (Braganza et al., Veterinary Immunology and Immunopathology 139 (2011) 27-40). Dogs were found to express 90% lambda and only 10% of kappa light chains (Braganza et al., Veterinary Immunology and Immunopathology 139 (2011) 27-40). However, the distribution and arrangement of the specific light chains of canines as well the VH/VL combinations occurring in dogs are hardly characterized so far.

Based on the distribution of the VH genes as described in the literature and sequence similarity analysis specific VH genes were selected for the synthetic canine antibody library. For the VL genes the information provided in Braganza et al., 2011 and a consensus sequence based on the 86 lambda light chain germline sequences and 29 kappa light chain germline sequences available on http with the extension vgenerepertoire.org of the world wide web were used to select specific light chain germline sequences for the synthetic canine antibody library.

We tested five representative canine VH germline sequences and six representative canine VL germline sequences (4 lambda VLs, 2 kappa VLs). Out of the 30 possible VH/VL combinations we identified 6 combinations which exhibited the following advantageous properties: (i) they showed a high display rate on the tip of filamentous phages in Fab-format, (ii) they are expressed in soluble form with a high monomeric content in Fab format and (iii) are expressed with a high monomeric content in IgG format.

The selection of the frameworks was chosen to optimize the chance of obtaining antibodies which possess favorable biophysical properties and which are devoid of short comings of antibodies derived from synthetic libraries which have not undergone in-vivo maturation. Such favorable and desired biophysical properties for example include higher stability and a low tendency for aggregation as exemplified herein.

For the six most favorable VH/VL combinations the L-CDR3 and the H-CDR3 regions were replaced by highly diversified L-CDR3 and H-CDR3 library cassettes, respectively, thereby achieving an overall library size of more than $5\times10^9$ members. Respective restriction sites were implemented to enable L-CDR3 and H-CDR3-library cassette insertion.

In addition, unfavorable post-translational modification (PTM) sites were removed from specific germline sequences to further optimize expression and biophysical properties of the respective VH or VL genes and corresponding proteins.

It is important to be aware of post-translational modifications that occur in antibody formulations for therapeutic applications. PTMs not necessarily take place in antibody samples produced for initial in vitro characterization, however PTMs might take place in antibody samples of high concentration and under long storage conditions, but also occur in vivo. Thereby, PTMs can interfere with antibody stability and/or homogeneity and might lead to loss of antibody functionality. Examples of PTMs include but are not limited to Oxidation (Met, Trp, His), Deamidation (Asn, Gln), Isomerization (Asp) or N-linked glycosylation (Asn).

The present disclosure provides synthetic canine antibody libraries, preferably libraries comprising members of at least one germline VH1 region and at least one germline VL region.

In one aspect, said libraries provided herein comprise members of at least two germline VH1 region and at least two germline VL regions.

In one aspect, provided herein is a synthetic canine antibody library, wherein said library comprises members of at least one of the following germline VH1 regions: Vs618 (SEQ ID NO:4), Vs624 (SEQ ID NO:1) and Vs635 (SEQ ID NO:2).

In one aspect, provided herein is a synthetic canine antibody library wherein said library comprises members of at least two of the following germline VH1 regions: Vs618 (SEQ ID NO:4), Vs624 (SEQ ID N0:1) and Vs635 (SEQ ID NO:2). In another aspect, provided herein is a synthetic canine antibody library wherein said library further comprises members of at least two germline VL regions.

In one aspect, provided herein is a synthetic canine antibody library, wherein said library comprises at least one of the following germline VL regions: Vs236 (kappa) (SEQ ID NO:12), Vs323 (lambda) (SEQ ID NO:16) and Vs365 (lambda) (SEQ ID NO:13), In one embodiment of the present disclosure said germline VL regions are selected from the following germline VL regions: Vs236 (kappa) (SEQ ID NO:12), Vs323 (lambda) (SEQ ID NO:16) and Vs365 (lambda) (SEQ ID NO:13).

In one aspect, provided herein is a synthetic canine antibody library wherein said library comprises at least two of the germline VH regions: Vs618 (SEQ ID NO:4), Vs624 (SEQ ID NO:1) and Vs635 (SEQ ID NO:2) and at least two of the following germline VL regions: Vs236 (kappa) (SEQ ID NO:12), Vs323 (lambda) (SEQ ID NO:16) and Vs365 (lambda) (SEQ ID NO:13).

In another aspect, provided herein is a synthetic canine antibody library wherein said library comprises the germline VH regions: Vs618 (SEQ ID NO:4), Vs624 (SEQ ID NO:1) and Vs635 (SEQ ID NO:2) and the following germline VL regions: Vs236 (kappa) (SEQ ID NO:12), Vs323 (lambda) (SEQ ID NO:16) and Vs365 (lambda) (SEQ ID NO:13).

In another aspect, provided herein is a synthetic canine antibody library wherein said library consists of at least one of the germline VH regions: Vs618 (SEQ ID NO:4), Vs624 (SEQ ID NO:1) and Vs635 (SEQ ID NO:2) and at least one of the following germline VL regions: Vs236 (kappa) (SEQ ID NO:12), Vs323 (lambda) (SEQ ID NO:16) and Vs365 (lambda) (SEQ ID NO:13).

In another aspect, provided herein is a synthetic canine antibody library wherein said library consists of at least two of the germline VH regions: Vs618 (SEQ ID NO:4), Vs624 (SEQ ID NO:1) and Vs635 (SEQ ID NO:2) and at least two of the following germline VL regions: Vs236 (kappa) (SEQ ID NO:12), Vs323 (lambda) (SEQ ID NO:16) and Vs365 (lambda) (SEQ ID NO:13).

In another aspect, provided herein is synthetic canine antibody library wherein said library consists of the germline VH regions: Vs618 (SEQ ID NO:4), Vs624 (SEQ ID NO:1) and Vs635 (SEQ ID NO:2) and the following germline VL regions: Vs236 (kappa) (SEQ ID NO:12), Vs323 (lambda) (SEQ ID NO:16) and Vs365 (lambda) (SEQ ID NO:13).

In another aspect, provided herein is synthetic canine antibody library, wherein post-translational modification (PTM) sites are removed from one or more of the germline VH regions or the germline VL regions.

In another aspect, provided herein is synthetic canine antibody library, wherein said library comprises the VH regions: Vs618 (SEQ ID NO:4), Vs624-PTM-low (SEQ ID NO:6) and Vs635-PTM-low (SEQ ID NO:7) and the VL regions: Vs236 (kappa) (SEQ ID NO:12), Vs323-PTM-low (lambda) (SEQ ID NO:18) and Vs365 (lambda) (SEQ ID NO:13).

In another aspect, provided herein is synthetic canine antibody library, wherein said library comprises the VH/VL combinations of the VH1 region Vs618 (SEQ ID NO:4) and the VL region Vs236 (kappa) (SEQ ID NO:12), the VHNL combination of the VH1 region Vs624-PTM-low (SEQ ID NO:6) and the VL region Vs236 (kappa) (SEQ ID NO:12), the VH/VL combination of the VH1 region Vs635-PTM-low (SEQ ID NO:7) and the VL region Vs323-PTM-low (lambda) (SEQ ID NO:18), the VH/VL combination of the VH1 region Vs618 (SEQ ID NO:4) and the VL region Vs365 (lambda) (SEQ ID NO:13), the VH/VL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7) and the VL region Vs365 (lambda) (SEQ ID NO:13).

In one aspect, provided herein is a synthetic canine antibody library wherein said library comprises members of at least two of the following germline VH1 regions: Vs618 (SEQ ID NO:4), Vs624 (SEQ ID NO:1), Vs628 (SEQ ID NO:5) and Vs635 (SEQ ID NO:2). In another aspect, provided herein is a synthetic canine antibody library wherein said library further comprises members of at least two germline VL regions.

In one aspect, provided herein is a synthetic canine antibody library, wherein said library comprises at least one of the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In one embodiment of the present disclosure said germline VL regions are selected from the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In one aspect, provided herein is a synthetic canine antibody library wherein said library comprises at least two of the germline VH regions: Vs618 (SEQ ID NO:4), Vs624 (SEQ ID NO:1), Vs628 (SEQ ID NO:5) and Vs635 (SEQ ID NO:2) and at least two of the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In another aspect, provided herein is a synthetic canine antibody library wherein said library comprises the germline VH regions: Vs618 (SEQ ID NO:4), Vs624 (SEQ ID NO:1), Vs628 (SEQ ID NO:5) and Vs635 (SEQ ID NO:2) and the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In another aspect, provided herein is a synthetic canine antibody library wherein said library consists of at least one of the germline VH regions: Vs618 (SEQ ID NO:4), Vs624 (SEQ ID NO:1), Vs628 (SEQ ID NO:5) and Vs635 (SEQ ID NO:2) and at least one of the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In another aspect, provided herein is a synthetic canine antibody library wherein said library consists of at least two of the germline VH regions: Vs618 (SEQ ID NO:4), Vs624 (SEQ ID NO:1), Vs628 (SEQ ID NO:5) and Vs635 (SEQ ID NO:2) and at least two of the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In another aspect, provided herein is synthetic canine antibody library wherein said library consists of the germline VH regions: Vs618 (SEQ ID NO:4), Vs624 (SEQ ID NO:1), Vs628 (SEQ ID NO:5) and Vs635 (SEQ ID NO:2) and the following germline VL regions: Vs236 (kappa) (SEQ ID NO:12), Vs321 (lambda) (SEQ ID NO: 14), Vs323 (lambda) (SEQ ID NO:16), Vs365 (lambda) (SEQ ID NO:13) and Vs843 (lambda) (SEQ ID NO:15).

In another aspect, provided herein is synthetic canine antibody library, wherein post-translational modification (PTM) sites are removed from one or more of the germline VH regions or the germline VL regions.

In another aspect, provided herein is synthetic canine antibody library, wherein said library comprises the VH regions: Vs618 (SEQ ID NO:4), Vs624-PTM-low (SEQ ID NO:6), Vs628-PTM-low (SEQ ID NO:10) and Vs635-PTM-low (SEQ ID NO:7) and the VL regions: Vs236 (kappa) (SEQ ID NO:12), Vs321 (lambda) (SEQ ID NO:14), Vs323-PTM-low (lambda) (SEQ ID NO:18), Vs365 (lambda) (SEQ ID NO:13) and Vs843 (lambda) (SEQ ID NO:15).

In another aspect, provided herein is synthetic canine antibody library, wherein said library comprises one or more of the following VH/VL combinations: the VHNL combination of the VH1 region Vs618 (SEQ ID NO:4) and the VL region Vs236 (kappa) (SEQ ID NO:12), the VHNL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VH/VL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VH/VL combination of the VH1 region Vs624-PTM-low (SEQ ID NO:6) and the VL region Vs843 (lambda) (SEQ ID NO:15), and the VHNL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VH/VL combination of the VH1 region Vs618 (SEQ ID NO:4) and the VL region Vs321 (lambda) (SEQ ID NO:14), the VH/VL combination of the VH1 region Vs624-PTM-low (SEQ ID NO:6) and the VL region Vs321 (lambda) (SEQ ID NO:14), the VH/VL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VH/VL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations comprises one or more of the VHNL combinations disclosed herein.

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations comprise one or more of the following VH/VL combinations: the VH/VL combination of the VH1 region Vs618 (SEQ ID NO:4) and the VL region Vs236 (kappa) (SEQ ID NO:12), the VHNL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VH/VL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VH/VL combination of the VH1 region Vs635-PTM-low (SEQ ID NO:7), the VL region Vs365 (lambda) (SEQ ID NO:13).

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations consist of one or more of the following VH/VL combinations: the VH/VL combination of the VH1 region Vs618 (SEQ ID NO:4) and the VL region Vs236 (kappa) (SEQ ID NO:12), the VHNL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VH/VL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13).

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations consist one or more of the VHNL combinations disclosed herein.

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations comprise at least 2, at least 3, at least 4, at least 5, at least 6 of the following VH/VL combinations: the VHNL combination of the VH1 region Vs618 (SEQ ID NO:4) and the VL region Vs236 (kappa) (SEQ ID NO:12), the VHNL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13).

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations consist of at least 2, at least 3, at least 4, at least 5, at least 6 of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13).

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations consist of at least 2, at least 3, at least 4, at least 5, at least 6 of the VHNL combinations disclosed herein.

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations consist one or more of the following VHNL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VH/VL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365

(lambda) (SEQ ID NO:13), the VH/VL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VHNL combination of the VH1 region Vs635-PTM-low (SEQ ID NO:7) and the VL region Vs843 (lambda) (SEQ ID NO:15), the VHNL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VH/VL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VH/VL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In another aspect, provided herein is a synthetic canine antibody library, wherein at least 50% of the antibodies or functional fragments comprise variable heavy chain and variable light chain combinations, wherein the framework regions of said variable heavy chain and variable light chain combinations comprise one or more of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VHNL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VHNL combination of the VH1 region Vs628-PTM-low (SEQ ID NO:10) and the VL region Vs843 (lambda) (SEQ ID NO:15).

In another aspect, provided herein is a synthetic canine antibody library, wherein at least 50%, at least 60%, at least 70%, at least 80% or at least 90% of the antibodies or functional fragments comprise variable heavy chain and variable light chain combinations, wherein the framework regions of said variable heavy chain and variable light chain combinations consist of at least 2, at least 3, at least 4, at least 5, at least 6, at least 8, at least 10, at least 12, at least 14, at least 16 of the following VHNL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VH/VL combination of the VH1 region Vs635-PTM-low (SEQ ID NO:7) and the VL region Vs323-PTM-low (lambda) (SEQ ID NO:18), the VH/VL combination of the VH1 region Vs618 (SEQ ID NO:4) and the VL region Vs365 (lambda) (SEQ ID NO:13), the VH/VL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VH/VL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VH/VL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VH/VL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In another aspect, provided herein is a synthetic canine antibody library, wherein at least 50% of the antibodies or functional fragments comprise variable heavy chain and variable light chain combinations, wherein the framework regions of said variable heavy chain and variable light chain combinations consist of at least 2, at least 3, at least 4, at least 5, at least 6, at least 8, at least 10, at least 12, at least 14, at least 16 of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VHNL combination of the VH1 region Vs618 (SEQ ID NO:4) and the VL region Vs323-PTM-low (lambda) (SEQ ID NO:18), the VH/VL combination of the VH1 region Vs624-PTM-low (SEQ ID NO:6) and the VL region Vs323-PTM-low (lambda) (SEQ ID NO:18), the VH/VL combination of the VH1 region Vs618 (SEQ ID NO:4) and the VL region Vs321 (lambda) (SEQ ID NO:14), the VH/VL combination of the VH1 region Vs624-PTM-low (SEQ ID NO:6) and the VL region Vs321 (lambda) (SEQ ID NO:14), the VHNL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VH/VL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In another aspect, provided herein is a synthetic canine antibody library, wherein at least 80% of the antibodies or functional fragments comprise variable heavy chain and variable light chain combinations, wherein the framework regions of said variable heavy chain and variable light chain combinations comprise one or more of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VHNL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VHNL combination of the VH1 region Vs628-PTM-low (SEQ ID NO:10) and the VL region Vs843 (lambda) (SEQ ID NO:15).

In another aspect, provided herein is a synthetic canine antibody library, wherein at least 50% of the antibodies or functional fragments comprise variable heavy chain and variable light chain combinations, wherein the framework regions of said variable heavy chain and variable light chain combinations consist of one or more of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VHNL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VHNL combination of the VH1 region Vs628-PTM-low (SEQ ID NO:10) and the VL region Vs843 (lambda) (SEQ ID NO:15).

In another aspect, provided herein is a synthetic canine antibody library, wherein at least 80% of the antibodies or functional fragments comprise variable heavy chain and variable light chain combinations, wherein the framework regions of said variable heavy chain and variable light chain combinations consist of one or more of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the VH1 region Vs618 (SEQ ID NO:4) and the VL region Vs365 (lambda) (SEQ ID NO:13), the VHNL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7), the VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VHNL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In one aspect, provided herein is a synthetic canine antibody library, preferably such library comprising members of at least one germline VH1 region and/or at least two germline VL regions, wherein essentially all VH/VL combinations of said library are efficiently displayed in Fab format.

In one aspect said VH/VL combinations of said library are displayed in Fab format, having a display rate of at least 0.5 Fab per phage.

In one aspect, provided herein is a synthetic canine antibody library, preferably such library comprising members of at least one germline VH1 region and/or at least two germline VL regions, wherein essentially all VH/VL combinations are expressed in E. coli in Fab format. In one embodiment said VHNL combinations expressed in E. coli in Fab format have a monomeric content of at least 75%, 80%, 85%, 90%, 95%, 96%, 97%, 98%, 99%, 100%.

In one aspect, provided herein is a synthetic canine antibody library, preferably such library comprising members of at least one germline VH1 region and/or at least two germline VL regions, wherein essentially all VH/VL combinations are expressed in a mammalian system in IgG format. In one embodiment said VHNL combinations expressed in a mammalian system in IgG format have a monomeric content of at least 75%, 80%, 85%, 90%. 95%, 96%, 97%, 98%, 99%, 100%.

In one aspect, provided herein is a synthetic canine antibody library, preferably such library comprising members of at least one germline VH1 region and/or at least two germline VL regions, wherein essentially all VH/VL combinations are thermally stable.

The present disclosure also provides collections of nucleic acid molecules encoding the antibodies of said synthetic canine antibody libraries.

The present disclosure also provides vectors encoding said nucleic acid molecules.

The present disclosure also provides recombinant host cells comprising said nucleic acid molecules or vectors.

The present disclosure also provides methods to isolate antibodies specific for an antigen, said method comprising the steps of:

(a) contacting the synthetic canine antibody libraries of the present disclosure with an antigen;

(b) removing those members of the library which do not bind to (or are not specific for) the antigen; and (c) recovering those members of the library bound to (or specific for) the antigen.

The present disclosure also provides antibodies isolated from a aforementioned libraries or aforementioned method.

BRIEF DESCRIPTION OF THE DRAWINGS

FIG. 1 and FIGS. 1a, 1b, 1c and 1d provide the identity table analysis of 41 canine VH genes showing distance values for all possible sequence pairs for the sequences that are included in the alignment. Distance scores (i.e., 100 minus identity score) between sequence pairs are indicated. Identity scores between sequence pairs are the percentage of identical residues among all ungapped positions between the pairs.

FIG. 2 provides the identity table analysis of 29 canine Vkappa genes showing distance values for all possible sequence pairs for the sequences that are included in the alignment. Distance scores (i.e., 100 minus identity score) between sequence pairs are indicated. Identity scores between sequence pairs are the percentage of identical residues among all ungapped positions between the pairs.

FIG. 3 and FIGS. 3a, 3b, 3c, 3d, 3e, 3f, 3q, 3h, 3i, 3j, 3k, 3L, 3m, 3n, 3o and 3p provide the identity table analysis of 86 canine Vlambda genes showing distance values for all possible sequence pairs for the sequences that are included in the alignment. Distance scores (i.e., 100 minus identity score) between sequence pairs are indicated. Identity scores between sequence pairs are the percentage of identical residues among all ungapped positions between the pairs.

FIG. 4 is a Western blot analysis of a subset of VHNL constructs to evaluate Fab-display rates.

FIG. 5 shows densiometric analysis of the blot shown in FIG. 4 indicating suitable display rates (typically, 0.5 to 2 Fabs/phage) for efficient phage display.

FIG. 6 shows analysis of 30 VHNL combinations for relative Fab expression in bacterial cell lysates by ELISA where the expression level of each VH/VL pair was determined relative to the expression of a reference Fab control. Essentially all tested Fab VHNL pairs showed a relative expression of at least 0.5 of the controls. Lambda clones had, on average, the highest relative Fab expression levels. Sample numbers are codified in Table 3.

FIG. 7 shows Fab expression yields (indicated as bars; left axis) and monomer contents (indicated as dots; right axis) of 30 VH/VL combinations. Sample numbers are codified in Table 3.

FIG. 8 shows research-scale IgG expression yields (indicated as bars; left axis) and monomer contents (indicated as dots; right axis) of 30 VHNL combinations. Sample numbers are codified in Table 3.

FIG. 9 shows essential parts of the phage display vector pCaDis including relevant unique restriction sites are shown.

FIG. 10 shows essential parts of the bacterial Fab expression vector pCaBx including relevant unique restriction sites are shown.

FIG. 11 shows high quality and correctness of the canine antibody library as shown by the VH mastergene distribution as expected per composition of the library.

FIG. 12 shows the designed amino acid distribution (left bar) in comparison to the obtained amino acids at the corresponding positions (right bar) in the library for an exemplary light chain CDR confirms an accurate and correct composition of the synthetic library.

FIG. 13 shows the design of the CDR-H3 length distribution (white bars) in comparison to the obtained CDR-H3 length distribution (dark bars) after MiSeq NGS quality control of ~7.9 million sequences.

FIG. 14 shows Dot Blot visualization of Fab screening results. Signal over background values of specific binding to eGFP is depicted on the x-axis (direct ELISA), results of the Fab expression are shown on the y-axis (signal over background in a Fab-capture ELISA). Shapes of the dots indicate the respective panning subcode.

FIG. 15 shows antibodies directly isolated from the library exhibit diverse binding strengths with 6/9 candidates showing similar or better binding characteristics as compared to the reference antibody anti-GFP antibody MOR06391.

FIG. 16 shows results of a standard solid phase ELISA confirming IgG reactivity against eGFP.

DETAILED DESCRIPTION OF THE INVENTION

Figure 3:
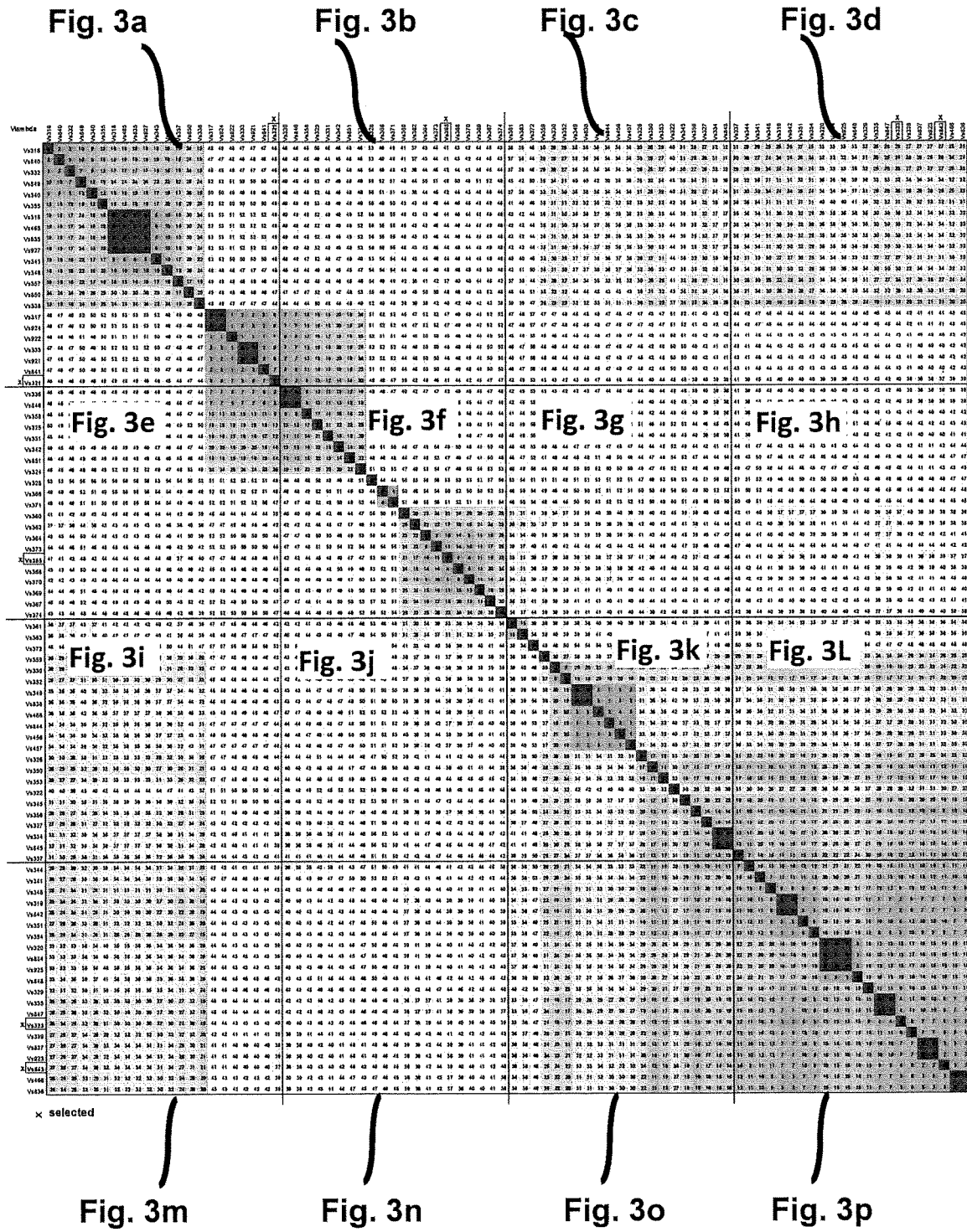

Unless defined otherwise, all technical and scientific terms used herein have the same meaning as commonly understood by those of ordinary skill in the art to which this invention pertains.

The terms "about" or "approximately" in the context of numerical values and ranges refers to values or ranges that approximate or are close to the recited values or ranges such that the invention can perform as intended, such as having a desired number or percentage of sequence homology, as is apparent to the skilled person from the teachings contained herein. This is due, at least in part, to the varying culture conditions and the variability of biological systems. Thus, these terms encompass values beyond those resulting from systematic error. These terms make explicit what is implicit.

All ranges set forth herein in the summary and description of the invention include all numbers or values thereabout or there between of the numbers of the range. The ranges of the invention expressly denominate and set forth all integers, decimals and fractional values in the range. The term "about" can be used to describe a range.

The term "antibody" as used herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region of an IgG, IgA or IgD antibody is comprised of three domains, CH1, CH2 and CH3, whereas the heavy chain of an IgM and IgE antibody is comprised of four domains CH1, CH2, CH3, CH4. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The extent of the framework region and CDRs have been precisely defined (see Kabat, 1991, J. Immunol., 147, 915-920; Chothia & Lesk, 1987, J. Mol. Biol. 196: 901-917; Chothia et al., 1989, Nature 342: 877-883; Al-Lazikani et al., 1997, J. Mol. Biol. 273: 927-948). The framework regions of an antibody, that is, the combined framework regions of the constituent light and heavy chains, serves to position and align the CDRs, which are primarily responsible for binding to an antigen.

The terms "antigen binding portion" or "fragment" of an antibody are used equivalently in the present application. These terms refer to one or more fragments of an intact antibody that retain the ability to specifically bind to a given antigen. Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain; and an isolated complementarity determining region (CDR). Preferred antigen binding portions or fragments of antibodies are Fab fragments.

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies. Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies). Antigen binding portions can be incorporated into single chain molecules comprising a pair of tandem Fv segments (VH—CH1-VH-CH1) which, together with complementary light chain polypeptides, form a pair of antigen binding regions (Zapata et al., 1995 Protein Eng. 8(10):1057-1062; and U.S. Pat. No. 5,641,870).

The term "canine antibody", as used herein, refers to antibodies having variable regions in which both the framework and CDR regions are derived from sequences of canine origin. For example both, the framework and CDR regions may be derived from sequences of canine origin. Furthermore, if the antibody contains a constant region, the constant region also is derived from such canine sequences, e.g., canine germline sequences, or mutated versions of canine germline sequences. The canine antibodies of the invention may include amino acid residues not encoded by canine sequences (e.g., mutations introduced by random or site-specific mutagenesis in vitro or by somatic mutation in vivo).

The term "naïve canine immune repertoire" means a repertoire of the nucleic acids isolated from antigen inexperienced B cells from the immune system of a dog, wherein the nucleic acids encoding the antibodies or functional fragments thereof have not undergone somatic hypermutation, therefore, are considered to comprise the nucleic acids of the germline genes, with the occurrence of V(D)J gene segment rearrangement. A repertoire may be that of an individual, or a population. Preferably, the immune repertoire is obtained from multiple individuals to avoid sample biases.

The term "canine immune repertoire" means a repertoire of the nucleic acids isolated from B cells from the immune system of a dog. A repertoire may be that of an individual, or a population, and may come from naïve B cells and/or antigen experienced B cells. Preferably, the immune repertoire is obtained from multiple individuals to avoid sample biases.

The term "isolated antibody" refers to an antibody that is substantially free of other antibodies having different antigenic binding specificities. An isolated antibody that specifically binds to an antigen may, however, have cross-reactivity to other antigens. Moreover, an isolated antibody may be substantially free of other cellular material and/or chemicals.

The term "isotype" refers to the antibody class (e.g., IgM, IgE, IgA, IgG such as IgG1 or IgG4) that is provided by the heavy chain constant region genes. In canine there are four IgG subclasses: IgG-A, IgG-B, IgG-C and IgG-D (L. M. Bergeron et al. Veterinary Immunology and Immunopathology 157 (2014) 31-41). Isotype also includes modified versions of one of these classes, where modifications have been made to alter the Fc function, for example, to enhance or reduce effector functions or binding to Fc receptors.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "library" refers to a collection of distinct molecules comprising typically more than $10^3$, more than $10^4$, more than $10^5$, more than $10^6$, more than $10^7$, more than $10^8$, more than $10^9$ or even more than $10^{10}$ members. A library in the context of the present invention is a mixture of heterogeneous polypeptides or nucleic acids. The library is composed of members, each of which have a single polypeptide or nucleic acid sequence. Sequence differences between library members are responsible for the diversity present in the library. The library may take the form of a simple mixture of polypeptides or nucleic acids, or may be in the form of organisms or cells, for example bacteria, viruses, phages, animal or plant cells, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a certain aspect, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants. The term "collection" is essentially used interchangeably with the term "library".

Antibody libraries can be derived from immunoglobulins, or fragments thereof, that are biased towards certain specificities present in immunized animals or naturally immunized, or infected, humans. Alternatively, antibody libraries can be derived from naïve immunoglobulins, or fragments thereof, i.e. immunoglobulins that are not biased towards specificities found in the immune system. Such libraries are referred to as "unbiased" libraries. In preferred embodiments, the present disclosure provides unbiased antibody libraries, i.e. the libraries are not pre-exposed to the antigen of interest. Due to the absence of any bias, such libraries comprise antibodies binding to any potential target antigen of interest.

Typically, immune antibody libraries are constructed with VH and VL gene pools that are cloned from source B cells by PCR-based (or related) cloning techniques. In the same way it is also possible to generate unbiased, naïve antibody libraries. Unbiased, naïve antibody libraries can however also be generated in a synthetic way in which the entire library is constructed entirely in vitro. Recombinant DNA technology is employed and may be used to mimic the natural biases and redundancies of the natural antibody repertoire. Such antibody libraries are referred to as "synthetic" antibody libraries. The term "fully synthetic" library refers to antibody libraries which are completely, i.e. fully, de novo constructed by DNA synthesis, e.g. by total gene synthesis, PCR-based methods, or related DNA technologies. In such libraries the entire DNA is constructed de novo, i.e. the part encoding the CDRs, as well as the parts (e.g. the framework regions) encoding the parts surrounding the CDRs of the antibodies of the library. The terms "synthetic" and "fully synthetic" therefore refer to the de novo origin of the DNA. In contrast, in a "semi-synthetic" antibody library only parts of the antibodies of the library are constructed de novo, whereas other parts, e.g. certain CDR regions, are derived from natural sources (numerous reviews on this matter exist, see e.g. Sidhu et al; Nat Chem Biol (2006), 2, 682-8). In certain aspects, the present disclosure provides a synthetic canine antibody library. In preferred aspect, the present disclosure provides a fully synthetic canine antibody library.

The term "fully germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation. The term "germline" refers to fully germline sequences and in addition to germline sequences that have been modified or engineered with minor mutations in the amino acid sequence, such as, for the purpose of removing of undesired post-translational modification (PTM) sites, of removing undesired cysteine, optimizing the antibody (e.g. affinity, half-life) or introduction of desired restriction site, or modifications that result from errors in synthesis, amplification or cloning.

The term "post-translational modification" or "PTM" refers to a generally enzymatic modification of proteins during or after protein biosynthesis. Post-translational modifications can occur on the amino acid side chains or at the protein's C- or N-termini. They can extend the chemical repertoire of the 20 standard amino acids by introducing new functional groups such as phosphate, acetate, amide groups, or methyl groups. Many eukaryotic proteins also have carbohydrate molecules attached to them in a process called glycosylation, which can promote protein folding and improve stability as well as serving regulatory functions. Modifications occur at so-called post-translational modification sites (i.e., defined amino acid motifs) that include specifically, N-linked glycosylation sites (NxS or NxT) or chemical modifications such as Asp cleavage (often at a DP), Asp isomerization (DS, DG), deamidation (NS, NG). Methionines can be oxidized when exposed to solvent. Modifications can occur in vivo (in serum) or upon storage in formulation buffer and lead to loss of antibody binding).

The term "germline variable region" means:

a) a nucleic acid sequence or an amino acid sequence of a variable region of an antibody or a functional fragment thereof encoded by a germline gene;

b) a nucleic acid sequence or an amino acid sequence of a variable region of an antibody or a functional fragment thereof encoded by a germline gene, wherein the nucleic acid sequence is modified by, for example, codon optimization, the addition of desired restriction sites, optimized GC content, the removal of undesired post-translational modification (PTM) sites, the removal of undesired mRNA splice sites or the removal of mRNA instability motifs, or c) a nucleic acid sequence or an amino acid sequence of a variable region of an antibody or a functional fragment thereof encoded by a germline gene, but with minor mutations in the amino acid sequence, such as, for the purpose of removing of undesired post-translational modification (PTM) sites, of removing undesired cysteine, or introduction of desired restriction site, or modifications that result from errors in synthesis, amplification or cloning.

In the sense of the present disclosure a "germline variable region" is a "germline VH region" or a "germline VL region". Examples of canine "germline variable regions" are shown in Table 1.

The term "variable heavy chain and variable light chain combination" or "VH/VL combination" means the combination (pairing) of one variable heavy chain and one variable light chain. An antibody and functional fragment, e.g. a Fab, comprises at least one variable heavy chain bound to a variable light chain, which form the antigen binding region.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary (CHO) cell or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "recominant antibody", as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express a rodent, human or canine antibody, e.g., from a transfectoma, antibodies isolated from a recombinant, combinatorial canine antibody library, and antibodies prepared, expressed, created or isolated by any other means that involve splicing of all or a portion of a canine immunoglobulin gene, sequences to other DNA sequences. Such recombinant canine antibodies have variable regions in which the framework and CDR regions are derived from canine germline immunoglobulin sequences. In certain embodiments, however, such recombinant canine antibodies can be subjected to in vitro mutagenesis (or, when an animal transgenic for canine Ig sequences is used, in vivo somatic mutagenesis) and thus the amino acid sequences of the VH and VL regions of the recombinant antibodies are sequences that, while derived from and related to canine germline VH and VL sequences, may not naturally exist within the germline canine antibody repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" refers to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A "display vector" includes a DNA sequence having the ability to direct replication and maintenance of the recombinant DNA molecule extra chromosomally in a host cell, such as a bacterial host cell, transformed therewith. Such DNA sequences are well known in the art. Display vectors can for example be phage vectors or phagemid vectors originating from the class of fd, M13, or fl filamentous bacteriophage. Such vectors are capable of facilitating the display of a protein including, for example, a binding protein or a fragment thereof, on the surface of a filamentous bacteriophage. Display vectors suitable for display on phage, ribosomes, DNA, bacterial cells or eukaryotic cells, for example yeast or mammalian cells are also known in the art, for example, as are viral vectors or vectors encoding chimeric proteins.

Restriction sites that are "unique" are restriction sites that exist or appear only once on a given nucleic acid molecule. Typically such a nucleic acid molecule is a vector which encodes the library members of the present invention.

The term "position-dependent amino-acid usage" refers to the likelihood of occurrence of a particular amino acid sequence at a given position in a polypeptide. In the present invention, the position-dependent amino acid usage was determined for the re-arranged amino acid sequences classified by the individual germline gene. This enables the individual, precise design of the CDRs within its natural germline context.

As used herein, the term "essentially all" means that the component to which it refers is more or less pure. Only small amounts or other, different components do exits which do not limit or affect the advantageous property of the component. Depending on the nature of the component essentially all may refer to at least 60%, at least 65%, at least 70%, at least 75%, at least 80%, at least 85%, at least 90%, at least 95% or at least 99% of that component.

As used herein, the term "PTM-low" refers to an antibody germline VH and/or VL amino acid sequence that has been modified within Kabat H-CDR1 and/or H-CDR2 to remove potential post translational modification (PTM) sites. Preferably, potential PTM motifs in framework regions FR1, FR2, FR3 and FR4 are not modified.

The J region amino acid sequences for FR4 of heavy chain, of kappa light chain and of lambda light chain are WGQGTLVTVSS (SEQ ID NO: 37), FGAGTKVELK (SEQ ID NO: 38 and FGGGTQLTVL (SEQ ID NO: 39), respectively as shown in Table 2.

Embodiments of the Invention

In certain aspects the present disclosure provides a synthetic canine antibody library which comprises members of at least one germline VH1 region. In other aspects said library comprises members of at least two or at least three or at least four germline VH1 regions.

In certain aspects said germline VH1 regions are selected from Vs618 (SEQ ID NO:4), Vs624 (SEQ ID NO:1), Vs628 (SEQ ID NO:5) and Vs635 (SEQ ID NO:2).

In certain aspects said germline VH1 regions are selected from optimized variants of Vs618 (SEQ ID NO:4), Vs624 (SEQ ID NO:1), Vs628 (SEQ ID NO:5) and Vs635 (SEQ ID NO:2).

In certain aspects said germline VH1 regions are identical with an identity of at least 70%, at least 80%, at least 85%, at least 90%, at least 95% or at least 99% to the germline VH1 regions selected from Vs618 (SEQ ID NO:4), Vs624 (SEQ ID NO:1), Vs628 (SEQ ID NO:5) and Vs635 (SEQ ID NO:2).

In certain aspects said germline VH1 regions are selected from Vs618 (SEQ ID NO:4), Vs624 (SEQ ID NO:1), Vs628 (SEQ ID NO:5) and Vs635 (SEQ ID NO:2), wherein post-translational modification (PTM) sites are removed.

In certain aspects said germline VH1 regions are selected from Vs618-PTM-low (SEQ ID NO:9), Vs624-PTM-low (SEQ ID NO:6), Vs628-PTM-low (SEQ ID NO:10) and Vs635-PTM-low (SEQ ID NO:7).

In certain aspects the synthetic canine antibody libraries as disclosed herein are unbiased. In certain aspects the synthetic canine antibody libraries as disclosed herein are fully synthetic canine antibody libraries.

In certain aspects the present disclosure provides a synthetic canine antibody library which comprises more than 50% of the natural canine VH repertoire. In other aspects said library comprises more than 60%, more than 70%, more than 75%, more than 80%, more than 85%, more than 90% or more than 95% of the natural canine VH repertoire.

In certain aspects the present disclosure provides a synthetic canine antibody library which comprises members of at least one germline VL region.

In other aspects said library comprises members of at least two or at least three or at least four or at least five germline VL regions.

In certain aspects said germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (SEQ ID NO:15).

In certain aspects said germline VL regions are selected from optimized variants of Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (SEQ ID NO:15).

In certain aspects said germline VL regions are identical with an identity of at least 70%, at least 80%, at least 85%, at least 90%, at least 95% or at least 99% to the germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (SEQ ID NO:15).

In certain aspects said germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (SEQ ID NO:15), wherein post-translational modification (PTM) sites are removed.

In certain aspects said germline VL regions are selected from Vs236 (kappa) (SEQ ID NO:12), Vs321 (lambda) (SEQ ID NO:14), Vs323-PTM-low (lambda) (SEQ ID NO:18), Vs365 (lambda) (SEQ ID NO:13), Vs843 (lambda) (SEQ ID NO:15).

In certain aspects the present disclosure provides a synthetic canine antibody library which comprises more than 50% of the natural canine VL repertoire. In other aspects said library comprises more than 60%, more than 70%, more than 75%, more than 80%, more than 85%, more than 90% or more than 95% of the natural canine VL repertoire.

In certain aspects the present disclosure provides a synthetic canine antibody library which comprises members of at least one germline VH1 region and of at least one germline VL region.

In other aspects said library comprises members of at least two or at least three or at least four germline VH1 regions and of at least two or at least three or at least four or at least five germline VL regions.

In certain aspects one or more of said germline VH1 regions and germline VL regions are optimized variants germline VH1 regions or germline VL regions.

In certain aspects said germline VH1 regions are selected from Vs618 (SEQ ID NO:4), Vs624 (SEQ ID NO:1), Vs628 (SEQ ID NO:5) and Vs635 (SEQ ID NO:2) and said germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (lambda) (SEQ ID NO: 15).

In certain aspects said germline VH1 regions are selected from Vs618 (SEQ ID NO:4), Vs624 (SEQ ID NO:1), Vs628 (SEQ ID NO:5) and Vs635 (SEQ ID NO:2) and said germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (lambda) (SEQ ID NO: 15), wherein post-translational modification (PTM) sites are removed.

In certain aspects said germline VH1 regions are identical with an identity of at least 70%, at least 80%, at least 85%, at least 90%, at least 95% or at least 99% to the germline VH1 regions selected from Vs618 (SEQ ID NO:4), Vs624 (SEQ ID NO:1), Vs628 (SEQ ID NO:5) and Vs635 (SEQ ID NO:2) and said germline VL regions are identical with an identity of at least 70%, at least 80%, at least 85%, at least 90%, at least 95% or at least 99% to the germline VL regions selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (lambda) (SEQ ID NO: 15).

In certain aspects said germline VH1 regions are selected from Vs618-PTM-low (SEQ ID NO:9), Vs624-PTM-low (SEQ ID NO:6), Vs628-PTM-low (SEQ ID NO:10) and Vs635-PTM-low (SEQ ID NO:7) and from Vs236 (kappa) (SEQ ID NO:12), Vs321 (lambda) (SEQ ID NO: 14), Vs323-PTM-low (lambda) (SEQ ID NO:18), Vs365 (lambda) (SEQ ID NO:13) and VS843 (lambda) (SEQ ID NO:15).

In certain aspects the present disclosure provides a synthetic canine antibody library which comprises VHNL combinations of at least one germline VH1 region and of at least one germline VL region.

In other aspects said library comprises VHNL combinations of at least two or at least three or at least four germline VH1 regions and of at least two or at least three or at least four or at least five germline VL regions.

In certain aspects said germline VH1 regions are selected from Vs618 (SEQ ID NO:4), Vs624 (SEQ ID NO:1), Vs628 (SEQ ID NO:5) and Vs635 (SEQ ID NO:2) and said germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13), Vs843 (lambda) (SEQ ID NO:15).

In certain aspects said germline VH1 regions are selected from Vs618 (SEQ ID NO:4), Vs624 (SEQ ID NO:1), Vs628 (SEQ ID NO:5) and Vs635 (SEQ ID NO:2) and said germline VL regions are selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (lambda) (SEQ ID NO:15), wherein post-translational modification (PTM) sites are removed.

In certain aspects said germline VH1 regions are identical with an identity of at least 70%, at least 80%, at least 85%, at least 90%, at least 95% or at least 99% to the germline VH1 regions selected from Vs618 (SEQ ID NO:4), Vs628 (SEQ ID NO:5), Vs624 (SEQ ID NO:1) and Vs635 (SEQ ID NO:2) and said germline VL regions are identical with an identity of at least 70%, at least 80%, at least 85%, at least 90%, at least 95% or at least 99% to the germline VL regions selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (lambda) (SEQ ID NO:15). In certain aspects said germline VH1 regions are selected from Vs618-PTM-low (SEQ ID NO:9), Vs624-PTM-low (SEQ ID NO:6), Vs628-PTM-low (SEQ ID NO:10) and Vs635-PTM-low (SEQ ID NO:7) and from Vs236 (kappa) (SEQ ID NO:12), Vs321 (lambda) (SEQ ID NO:14), Vs323-PTM-low (lambda) (SEQ ID NO:18), Vs365 (lambda) (SEQ ID NO:13) and Vs843 (lambda) (SEQ ID NO:15).

In certain aspects the present disclosure provides a synthetic canine antibody library which comprises one or more VHNL combinations selected from the VHNL combinations of the germline VH1 region Vs618 (SEQ ID NO:4) and the germline VL region Vs236 (kappa) (SEQ ID NO:12), the VH/VL combination of the germline VH1 region Vs624 (SEQ ID NO:1) and the germline VL region Vs236 (kappa) (SEQ ID NO:12), the VHNL combination of the germline VH1 region Vs635 (SEQ ID NO:2) and the germline VL region Vs323 (lambda) (SEQ ID NO:16), the VHNL combination of the germline VH1 region Vs618 (SEQ ID NO:4) and the germline VL region Vs365 (lambda) (SEQ ID NO:13), the VH/VL combination of the germline VH1 region Vs624 (SEQ ID NO:1) and the germline VL region Vs365 (lambda) (SEQ ID NO:13) and the VHNL combination of the germline VH1 region Vs635 (SEQ ID NO:2) and the germline VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VHNL combination of the VH1 region Vs618 (SEQ ID NO:4) and the VL region Vs323-PTM-low (lambda) (SEQ ID NO:18), the VH/VL combination of the VH1 region Vs624-PTM-low (SEQ ID NO:6) and the VL region Vs323-PTM-low (lambda) (SEQ ID NO:18), the VH/VL combination of the VH1 region Vs618 (SEQ ID NO:4) and the VL region Vs321 (lambda) (SEQ ID NO:14), the VH/VL combination of the VH1 region Vs624-PTM-low (SEQ ID NO:6) and the VL region Vs321 (lambda) (SEQ ID NO:14), the VHNL combination of the VH1 region Vs635-PTM-low (SEQ ID NO:7) and the VL region Vs321 (lambda) (SEQ ID NO:14), the VHNL combination of the VH1 region Vs635-PTM-low (SEQ ID NO:7) and the VL region Vs236 (kappa) (SEQ ID NO:12) the VHNL combination of the VH1 region Vs628-PTM-low (SEQ ID NO:10) and the VL region VS236 (kappa) (SEQ ID NO:12), the VH/VL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In certain aspects of the present disclosure said VHNL combinations comprise a germline VH1 or a germline VL region which is identical with an identity of at least 70%, at least 80%, at least 85%, at least 90%, at least 95% or at least 99% to the germline VH1 regions and/or germline VL regions according to SEQ ID NO:4, SEQ ID NO:1, SEQ ID NO:2, SEQ ID NO:12, SEQ ID NO:16, SEQ ID NO:14, SEQ ID NO:15 and SEQ ID NO:13.

In certain aspects the present disclosure provides a synthetic canine antibody library which comprises at least one, at least two, at least three, at least four, at least five, at least six, at least seven, at least eight or at least nine VHNL combinations selected from the VHNL combinations of the germline VH1 region Vs618 (SEQ ID NO:4) and the germline VL region Vs236 (kappa) (SEQ ID NO:12), the VHNL combination of the germline VH1 region Vs624 (SEQ ID NO:1) and the germline VL region Vs236 (kappa) (SEQ ID NO:12), the VH/VL combination of the germline VH1 region Vs635 (SEQ ID NO:2) and the germline VL region Vs323 (lambda) (SEQ ID NO:16), the VHNL combination of the germline VH1 region Vs618 (SEQ ID NO:4) and the germline VL region Vs365 (lambda) (SEQ ID NO:13), the VHNL combination of the germline VH1 region Vs624 (SEQ ID NO:1) and the germline VL region Vs365 (lambda) (SEQ ID NO:13) and the VHNL combination of the germline VH1 region Vs635 (SEQ ID NO:2) and the germline VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VHNL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VH/VL combination of the VH1 region Vs635-PTM-low (SEQ ID NO:7) and the VL region Vs321 (lambda) (SEQ ID NO:14), and the VH/VL combination of the VH1 region Vs635-PTM-low (SEQ ID NO:7) and the VL region Vs236 (kappa) (SEQ ID NO:12).

In certain aspects the present disclosure provides a synthetic canine antibody library which consists of at least one, at least two, at least three, at least four, at least five at least six, at least seven, at least eight or at least nine VH/VL combinations selected from the VHNL combinations of the germline VH1 region Vs618 (SEQ ID NO:4) and the germline VL region Vs236 (kappa) (SEQ ID NO:12), the VHNL combination of the germline VH1 region Vs624 (SEQ ID NO:1) and the germline VL region Vs236 (kappa) (SEQ ID NO:12), the VH/VL combination of the germline VH1 region Vs635 (SEQ ID NO:2) and the germline VL region Vs323 (lambda) (SEQ ID NO:16), the VHNL combination of the germline VH1 region Vs618 (SEQ ID NO:4) and the germline VL region Vs365 (lambda) (SEQ ID NO:13), the VHNL combination of the germline VH1 region Vs624 (SEQ ID NO:1) and the germline VL region Vs365

(lambda) (SEQ ID NO:13) and the VHNL combination of the germline VH1 region Vs635 (SEQ ID NO:2) and the germline VL region Vs365 (lambda) (SEQ ID NO:13), the VHNL combination of the VH1 region Vs618 (SEQ ID NO:4) and the VL region Vs843 (lambda) (SEQ ID NO:15), the VHNL combination of the VH1 region Vs624-PTM-low (SEQ ID NO:6) and the VL region Vs843 (lambda) (SEQ ID NO:15), and the VHNL combination of the VH1 region Vs635-PTM-low (SEQ ID NO:7) and the VL region Vs843 (lambda) (SEQ ID NO:15), the VHNL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), the VH/VL combination of the VH1 region Vs635-PTM-low (SEQ ID NO:7) and the VL region Vs321 (lambda) (SEQ ID NO:14), and the VH/VL combination of the VH1 region Vs635-PTM-low (SEQ ID NO:7) and the VL region Vs236 (kappa) (SEQ ID NO:12).

In certain aspects the present disclosure provides a synthetic canine antibody library which consists of the VHNL combinations of the germline VH1 region Vs618 (SEQ ID NO:4) and the germline VL region Vs236 (kappa) (SEQ ID NO:12), the VHNL combination of the germline VH1 region Vs624 (SEQ ID NO:1) and the germline VL region Vs236 (kappa) (SEQ ID NO:12), the VH/VL combination of the germline VH1 region Vs635 (SEQ ID NO:2) and the germline VL region Vs323 (lambda) (SEQ ID NO:16), the VHNL combination of the germline VH1 region Vs618 (SEQ ID NO:4) and the germline VL region Vs365 (lambda) (SEQ ID NO:13), the VHNL combination of the germline VH1 region Vs624 (SEQ ID NO:1) and the germline VL region Vs365 (lambda) (SEQ ID NO:13) and the VHNL combination of the germline VH1 region Vs635 (SEQ ID NO:2) and the germline VL region Vs365 (lambda) (SEQ ID NO:13).

In certain embodiments the present disclosure provides a synthetic canine antibody library which comprises H-CDR3s which cover more than 50% of the naturally occurring H-CDR3 lengths of the canine H-CDR3 repertoire. In other aspects said library comprises more than 60%, more than 70%, more than 75%, more than 80%, more than 85%, more than 90% or more than 95% of the naturally occurring H-CDR3 lengths of the canine H-CDR3 repertoire.

In certain embodiments the present disclosure provides a synthetic canine antibody library, wherein the H-CDR3 regions of essentially all members of the library are flanked by unique restriction sites.

In certain aspects the present disclosure provides a synthetic canine antibody library which comprises H-CDR3s of the Kabat length of 5-16 amino acids. In other aspects the present disclosure provides a synthetic canine antibody library which comprises H-CDR3s of the Kabat length of 5 amino acids and/or 6 amino acids and/or 7 amino acids and/or 8 amino acids and/or 9 amino acids and/or 10 amino acids and/or 11 amino acids and/or 12 amino acids and/or 13 amino acids and/or 14 amino acids and/or 15 amino acids and/or 16 amino acids.

In certain aspects the present disclosure provides a synthetic canine antibody library which comprises an H-CDR3 design as shown in Tables 4-15.

In certain aspects the present disclosure provides a synthetic canine antibody library in which the H-CDR3 region has a diversity of at least $1.0*10^9$. In other aspects the present disclosure provides a synthetic canine antibody library which the H-CDR3 region has a diversity of at least $1.0*10^{10}$, of at least $1.0*10^{11}$, of at least $1.0*10^{12}$ or of at least $1.0*10^{13}$.

In certain aspects the present disclosure provides a synthetic canine antibody library wherein the L-CDR3 regions of essentially all members of the library are flanked by unique restriction sites.

In certain aspects the present disclosure provides a synthetic canine antibody library which comprises L-CDR3s which cover more than 80% of the naturally occurring L-CDR3 lengths of the canine L-CDR3 repertoire. In other aspects said library comprises more than 85%, more than 90% or more than 95% of the naturally occurring L-CDR3 lengths of the canine L-CDR3 repertoire.

In certain aspects the present disclosure provides a synthetic canine antibody library which comprises a Kabat L-CDR3 for Vkappa of the length of 9 amino acids. In certain aspects the present invention provides a synthetic canine antibody library in which the L-CDR3 of essentially all Vkappa members of the library is of the Kabat length of 9 amino acids.

In certain aspects the present disclosure provides a synthetic canine antibody library which comprises an L-CDR3 for Vlambda of the Kabat length of 10 and/or 11 amino acids. In certain aspects the present invention provides a synthetic canine antibody library in which the L-CDR3 of essentially all Vlambda members of the library is of the length of 10 and/or 11 amino acids.

In certain aspects the present disclosure provides a synthetic canine antibody library which comprises a Vkappa L-CDR3 design as shown in Table 16.

In certain aspects the present disclosure provides a synthetic canine antibody library which comprises a Vlambda L-CDR3 design as shown in Tables 17-18.

In certain aspects the present disclosure provides a synthetic canine antibody library in which the L-CDR3 region has a diversity of at least $1.0*10^4$. In other aspects the present invention provides a synthetic canine antibody library which the L-CDR3 region has a diversity of at least $1.0*10^5$, of at least $1.0*10^6$, of at least $1.0*10^7$ or of at least $1.0*10^8$.

In certain aspects the present disclosure provides a synthetic canine antibody library which comprises an H-CDR3 design as shown in Tables 4-15 and an L-CDR3 design as shown in Table 16 and in Tables 17-18.

In certain aspects the present disclosure provides a synthetic canine antibody library wherein essentially all VH/VL combinations are efficiently displayed on a phage particle.

In yet other aspects the present disclosure provides a synthetic canine antibody library comprising at least two or at least three germline VH regions and at least two or at least three germline VL regions, wherein each of the VH/VL combinations comprised in said library is efficiently displayed. Efficiency of display can be measured by sandwich phage ELISA as described herein in Example 2.6. In other aspects the present disclosure provides a synthetic canine antibody library comprising at least two or at least three germline VH regions and at least two or at least three germline VL regions, wherein each of the VHNL combinations comprised in said library are efficiently displayed, having a display rate of at least 0.5 Fab per phage. In further embodiments the display rate is at least 0.6, at least 0.7, at least 0.8, at least 0.9, at least 1, at least 1.1, at least 1.2, at least 1.3, at least 1.4 at least 1.5, at least 1.6, at least 1.7, at least 1.8, at least 1.9, at least 2, at least 2.1, at least 2.2, at least 2.3, at least 2.4 at least 2.5, at least 2.6, at least 2.7, at least 2.8, at least 2.9, at least 3.0, at least 3.1, at least 3.2, at least 3.3, at least 3.4, at least 3.5, at least 3.6, at least 3.7, at least 3.8, at least 3.9 or at least 4 Fab per phage.

In yet other aspects the present disclosure provides a synthetic canine antibody library comprising at least two or at least three germline VH regions and at least two or at least three germline VL regions, wherein essentially all VH/VL combinations expressed in *E. coli* in Fab format have a monomeric content of at least 60%, at least 70%, at least 80%, at least 85%, at least 90%, at least 95%, at least 98% or at least 99%. In yet other aspects the present disclosure provides a synthetic canine antibody library comprising at least two or at least three germline VH regions and at least two or at least three germline VL regions, wherein each of the VH/VL combinations comprised in said library is expressed in *E. coli* in Fab format have a monomeric content of at least 60%, at least 70%, at least 80%, at least 85%, at least 90%, at least 95%, at least 98% or at least 99%.

In certain aspects the present disclosure provides a synthetic canine antibody library wherein essentially all VH/VL combinations are expressed in *E. coli* in Fab format. In yet other aspects the present disclosure provides a synthetic canine antibody library comprising at least two or at least three germline VH regions and at least two or at least three germline VL regions, wherein each of the VH/VL combinations comprised in said library is well expressed in *E. coli* in Fab format. Expression in Fab format in *E. coli* can be quantified.

In certain aspects the present disclosure provides a synthetic canine antibody library wherein essentially all VH/VL combinations are expressed at levels of more than 1 mg/L in a bacterial culture.

In certain aspects the present disclosure provides a synthetic canine antibody library wherein essentially all VH/VL combinations are expressed at levels of more than 5 mg/L in a bacterial culture.

In certain aspects the present disclosure provides a synthetic canine antibody library wherein most VH/VL combinations are expressed at levels of more than 10 mg/L in a bacterial culture.

In certain aspects the present disclosure provides a synthetic canine antibody library wherein at least two, at least three, at least four or at least five VH/VL combinations are expressed at levels of more than 1 mg/L in a bacterial culture.

In certain aspects the present disclosure provides a synthetic canine antibody library wherein essentially all VH/VL combinations are well expressed in a mammalian system in IgG format. In yet other aspects the present disclosure provides a synthetic canine antibody library comprising at least two or at least three germline VH regions and at least two or at least three germline VL regions, wherein each of the VHNL combinations comprised in said library is well expressed in a mammalian system in IgG format. Expression in a mammalian system in IgG format can be quantified. In certain aspects said mammalian system is a mammalian suspension culture. In other aspects said mammalian system is a mammalian adherent cell culture. In certain aspects said IgG format is a canine IgG-B format. In other aspects said IgG format is a canine IgG-A, IgG-C or IgG-D format. In certain aspects said mammalian system comprises HKB11 cells. In other aspects said mammalian system comprises PERC.6 cells. In yet other aspects said mammalian system comprises CHO cells. In certain aspects the present disclosure provides a synthetic canine antibody library wherein essentially all VH/VL combinations are expressed at levels of more than 5 mg/L in a mammalian system in IgG format. In certain aspects the present disclosure provides a synthetic canine antibody library wherein essentially all VHNL combinations are expressed at levels of more than 10 mg/L in a mammalian system in IgG format. In certain aspects the present disclosure provides a synthetic canine antibody library wherein most VH/VL combinations are expressed at levels of more than 15 mg/L in a mammalian system in IgG format. In certain aspects the present disclosure provides a synthetic canine antibody library wherein at least two, at least three, at least four, at least five or at least six VHNL combinations are expressed at levels of more than 20 mg/L in a mammalian system in IgG format.

In certain aspects the present disclosure provides a synthetic canine antibody library wherein all or substantially all of the members of said library are stable in isoproanol at a concentration of 30% (v/v). It is an assumption that all CDR derivatives of a stable framework will behave like the tested VHNL pairs.

In certain aspects the present disclosure provides a synthetic canine antibody library wherein all or substantially all VHNL combinations are thermally stable. Thermal stability can be measured as described in the present application. In certain aspects the present disclosure provides a synthetic canine antibody library wherein essentially all VH/VL combinations have a $T_m$ of more than 62° C. In other aspects the present disclosure provides a synthetic canine antibody library wherein essentially all VHNL combinations have a $T_m$ of more than 64° C. In yet other aspects the present disclosure provides a synthetic canine antibody library wherein essentially all VH/VL combinations have a $T_m$ of more than 66° C. In yet other aspects the present disclosure provides a synthetic canine antibody library wherein most VH/VL combinations have a $T_m$ of more than 68° C. In yet other aspects the present disclosure provides a synthetic canine antibody library wherein many VH/VL combinations have a $T_m$ of more than 70° C. In certain aspects the present disclosure provides a synthetic canine antibody library wherein all or substantially all VH1-combinations have a $T_m$ of more than 70° C.

In certain aspects the present disclosure provides a collection of nucleic acid molecules encoding the library as disclosed herein.

In certain aspects the present disclosure provides a collection of nucleic acid molecules encoding a synthetic canine antibody library which comprises members of at least one germline VH1 region and of at least one germline VL region. In other aspects the present disclosure provides a collection of nucleic acid molecules encoding a synthetic canine antibody library wherein said library comprises members of at least two or at least three germline VH1 regions and of at least two or at least three germline VL regions. In other aspects the present disclosure provides a collection of nucleic acid molecules encoding a synthetic canine antibody library wherein said library comprises members of at least two or at least three or at least four germline VH1 regions and of at least two or at least three or at least four germline VL regions and wherein said nucleic acid molecules encoding said germline VH1 regions are selected from Vs618 (SEQ ID NO:22), Vs624 (SEQ ID NO:19), Vs628 (SEQ ID NO:23) and Vs635 (SEQ ID NO:20) and wherein said nucleic acid molecules encoding said germline VL regions are selected from Vs236 (kappa) (SEQ ID NO:30), Vs321 (lambda) (SEQ ID NO:32), Vs323 (lambda) (SEQ ID NO:34), Vs365 (lambda) (SEQ ID NO:31) and Vs834 (lambda) (SEQ ID NO:33). In certain aspects said nucleic acid molecules encoding said germline VH1 regions are selected from Vs618 (SEQ ID NO:22), Vs624 (SEQ ID NO:19), Vs628 (SEQ ID NO:23) and Vs635 (SEQ ID NO:20) and said nucleic acid molecules encoding said germline VL regions are selected from Vs236 (kappa) (SEQ ID NO:30), Vs321 (lambda) (SEQ ID NO:32), Vs323 (lambda) (SEQ ID NO:34), Vs365 (lambda) (SEQ ID NO:31), and Vs834 (lambda) (SEQ ID NO:33), wherein post-translational modification (PTM) sites are removed. In certain aspects said nucleic acid molecules are selected from Vs618-PTM-low (SEQ ID NO:22), Vs624-PTM-low (SEQ ID NO:24), Vs628-PTM-low (SEQ ID NO:28) and Vs635-PTM-low (SEQ ID NO:25) and from Vs236 (kappa) (SEQ ID NO:30), Vs321 (lambda) (SEQ ID NO:32), Vs323-PTM-low (lambda) (SEQ ID NO:36), VS843 (lambda) (SEQ ID NO:33) and Vs365 (lambda) (SEQ ID NO:31).

In certain aspects the present disclosure provides a collection of nucleic acid molecules encoding a synthetic canine antibody library which comprises VH/VL combinations of at least one germline VH1 region and of at least one germline VL region. In other aspects the present disclosure provides a collection of nucleic acid molecules encoding a synthetic canine antibody library which comprises VH/VL combinations of at least two or at least three or at least four germline VH1 regions and of at least two or at least three or at least four or at least five germline VL regions. In certain aspects said nucleic acid molecules encoding said germline VH1 regions are selected from Vs618 (SEQ ID NO:22), Vs624 (SEQ ID NO:19) and Vs635 (SEQ ID NO:20) and said nucleic acid molecules encoding said germline VL regions are selected from Vs236 (kappa) (SEQ ID NO:30), Vs323 (lambda) (SEQ ID NO:34) and Vs365 (lambda) (SEQ ID NO:31). In certain aspects said nucleic acid molecules encoding said germline VH1 regions are selected from Vs618 (SEQ ID NO:22), Vs624 (SEQ ID NO:19), Vs628 (SEQ ID NO:23) and Vs635 (SEQ ID NO:20) and said nucleic acid molecules encoding said germline VL regions are selected from Vs236 (kappa) (SEQ ID NO:30), Vs321 (lambda) (SEQ ID NO:32), Vs323 (lambda) (SEQ ID NO:34), Vs365 (lambda) (SEQ ID NO:31) and Vs843 (lambda) (SEQ ID NO:33), wherein post-translational modification (PTM) sites are removed. In certain aspects said nucleic acid molecules are selected from Vs618-PTM-low (SEQ ID NO:22), Vs624-PTM-low (SEQ ID NO:24) and Vs635-PTM-low (SEQ ID NO:25) and from Vs236 (kappa) (SEQ ID NO:30), Vs321 (lambda) (SEQ ID NO:32), Vs323-PTM-low (lambda) (SEQ ID NO:36), Vs365 (lambda) (SEQ ID NO:31) and Vs843 (lambda) (SEQ ID NO: 33).

In certain aspects the present disclosure provides a collection of nucleic acid molecules encoding a synthetic canine antibody library which comprises VH/VL combinations selected from the VH/VL combinations encoded by the nucleic acid molecules encoding the germline VH1 regions selected from Vs618 (SEQ ID NO:22), Vs624 (SEQ ID NO:19), Vs628 (SEQ ID NO:23 and Vs635 (SEQ ID NO:20) and nucleic acid molecules encoding the germline VL regions selected from Vs236 (kappa) (SEQ ID NO:30), Vs321 (lambda) (SEQ ID NO:32), Vs323 (lambda) (SEQ ID NO:34), Vs365 (lambda) (SEQ ID NO:31) and Vs843 (lambda) (SEQ ID NO:33). In certain aspects of the present disclosure said nucleic acid molecules encoding a synthetic canine antibody library are identical with an identity of at least 70%, at least 80%, at least 85%, at least 90%, at least 95% or at least 99% to the nucleic acid molecules selected from Vs618 (SEQ ID NO:22), Vs624 (SEQ ID NO:19), Vs628 (SEQ ID NO:23 or Vs635 (SEQ ID NO:20), Vs236 (kappa) (SEQ ID NO:30), Vs321 (lambda) (SEQ ID NO:32), Vs323 (lambda) (SEQ ID NO:34), Vs365 (lambda) (SEQ ID NO:31) and/or Vs843 (lambda) (SEQ ID NO:33).

In certain aspects the present disclosure provides a collection of nucleic acid molecules encoding a synthetic canine antibody library which comprises at least one, at least two, at least three, at least four, at least five, at least six, at least seven, at least eight or at least nine VH/VL combinations encoded by the nucleic acid molecules encoding the germline VH1 region Vs618 (SEQ ID NO:22) and the germline VL region Vs236 (kappa) (SEQ ID NO:30), the nucleic acid molecules encoding the germline VH1 region Vs624 (SEQ ID NO:19) and the germline VL region Vs236 (kappa) (SEQ ID NO:30), the nucleic acid molecules encoding the germline VH1 region Vs635 (SEQ ID NO:20) and the germline VL region Vs323 (lambda) (SEQ ID NO:34), the nucleic acid molecules encoding the germline VH1 region Vs618 (SEQ ID NO:22) and the germline VL region Vs365 (lambda) (SEQ ID NO:31), the nucleic acid molecules encoding the germline VH1 region Vs624 (SEQ ID NO:19) and the germline VL region Vs365 (lambda) (SEQ ID NO:31) and the nucleic acid molecules encoding the germline VH1 region Vs635 (SEQ ID NO:20) and the germline VL region Vs365 (lambda) (SEQ ID NO:31). In certain aspects the nucleic acids are optimized variants of one or more of the nucleic acids encoding the germline VH1 region Vs618 (SEQ ID NO:22), the germline VL region Vs236 (kappa) (SEQ ID NO:30), the germline VH1 region Vs624 (SEQ ID NO:19), the germline VL region Vs236 (kappa) (SEQ ID NO:30), the germline VH1 region Vs635 (SEQ ID NO:20), the germline VL region Vs323 (lambda) (SEQ ID NO:34), the germline VH1 region Vs618 (SEQ ID NO:22), the germline VL region Vs365 (lambda) (SEQ ID NO:31), the germline VH1 region Vs624 (SEQ ID NO:19), the germline VL region Vs365 (lambda) (SEQ ID NO:31), the germline VH1 region Vs635 (SEQ ID NO:20) and/or the germline VL region Vs365 (lambda) (SEQ ID NO:31). In certain aspects the nucleic acids are PTM-low variants of one or more of the nucleic acids the nucleic acids encoding the germline VH1 region Vs618 (SEQ ID NO:22), the germline VL region Vs236 (kappa) (SEQ ID NO:30), the germline VH1 region Vs624 (SEQ ID NO:19), the germline VL region Vs236 (kappa) (SEQ ID NO:30), the germline VH1 region Vs635 (SEQ ID NO:20), the germline VL region Vs323 (lambda) (SEQ ID NO:34), the germline VH1 region Vs618 (SEQ ID NO:22), the germline VL region Vs365 (lambda) (SEQ ID NO:31), the germline VH1 region Vs624 (SEQ ID NO:19), the germline VL region Vs365 (lambda) (SEQ ID NO:31), the germline VH1 region Vs635 (SEQ ID NO:20) and/or the germline VL region Vs365 (lambda) (SEQ ID NO:31).

In certain aspects the present disclosure provides a collection of nucleic acid molecules encoding a synthetic canine antibody library which comprises at least one, at least two, at least three, at least four, at least five, at least six, at least seven, at least eight or at least nine VH/VL combinations encoded by the nucleic acid molecules encoding the germline VH1 region Vs618-PTM-low (SEQ ID NO:27) and the germline VL region Vs236 (kappa) (SEQ ID NO:30), the nucleic acid molecules encoding the germline VH1 region Vs624-PTM-low (SEQ ID NO:24) and the germline VL region Vs236 (kappa) (SEQ ID NO:30), the nucleic acid molecules encoding the germline VH1 region Vs635-PTM-low (SEQ ID NO:25) and the germline VL region Vs323-PTM-low (lambda) (SEQ ID NO:36), the nucleic acid molecules encoding the germline VH1 region Vs618-PTM-low (SEQ ID NO:27) and the germline VL region Vs365 (lambda) (SEQ ID NO:31), the nucleic acid molecules encoding the germline VH1 region Vs624-PTM-low (SEQ ID NO:24) and the germline VL region Vs365 (lambda) (SEQ ID NO:31) and the nucleic acid molecules encoding the germline VH1 region Vs635-PTM-low (SEQ ID NO:25) and the germline VL region Vs365 (lambda) (SEQ ID NO:31), the nucleic acid molecules encoding the germline VH1 region Vs618 (SEQ ID NO:22) and the germline VL region Vs843 (lambda) (SEQ ID NO:33), the nucleic acid molecules encoding the germline VH1 region Vs624-PTM-low (SEQ ID NO:24) and the germline VL region Vs843 (lambda) (SEQ ID NO:33), the nucleic acid molecules encoding the germline VH1 region Vs635-PTM-low (SEQ ID NO:25) and the germline VL region Vs843 (lambda) (SEQ ID NO:33), the nucleic acid molecules encoding the germline VH1 region Vs618 (SEQ ID NO:22) and the germline VL region Vs323-PTM-low (lambda) (SEQ ID NO:36), the nucleic acid molecules encoding the germline VH1 region Vs624-PTM-low (SEQ ID NO:24) and the germline VL region Vs323-PTM-low (lambda) (SEQ ID NO:36), the nucleic acid molecules encoding the germline VH1 region Vs618 (SEQ ID NO:22) and the germline VL region Vs321 (lambda) (SEQ ID NO:32), the nucleic acid molecules encoding the germline VH1 region Vs624-PTM-low (SEQ ID NO:24) and the germline VL region Vs321 (lambda) (SEQ ID NO:32), the nucleic acid molecules encoding the germline VH1 region Vs635-PTM-low (SEQ ID NO:25) and the germline VL region Vs321 (lambda) (SEQ ID NO:32).

In certain aspects the present disclosure provides a vector encoding the nucleic acid molecules as disclosed in the embodiments of the present disclosure.

In certain aspects the present disclosure provides a recombinant host cell comprising the nucleic acid molecules as disclosed in the embodiments of the present disclosure.

In one aspect the present disclosure provides a method to isolate an antibody specific for an antigen, said method comprising the steps of:
(a) contacting the library according to any one of the embodiments disclosed herein with an antigen;
(b) removing those members of the library which do not bind to the antigen; and
(c) recovering those members of the library bound to the antigen.

In certain aspects the present disclosure provides canine antibodies which possess favorable biophysical properties. Such antibodies are devoid of short comings of antibodies derived from synthetic libraries which have not undergone in-vivo maturation. Such favorable and desired biophysical properties include higher stability, higher expression levels and a low tendency for aggregation.

In certain aspects the present disclosure provides an antibody isolated from a canine library contemplated by the present disclosure. In certain aspects said antibody may be a modified or a variant antibody of an antibody isolated from a canine library contemplated by the present disclosure.

In certain aspects the present disclosure provides synthetic canine antibody library.

In certain aspects the present disclosure provides a synthetic canine antibody library comprising members of at least one of the following germline VH1 regions: Vs618 (SEQ ID NO:4), Vs624 (SEQ ID NO:1), Vs628 (SEQ ID NO:5) and Vs635 (SEQ ID NO:2).

In certain aspects the present disclosure provides a synthetic canine antibody library comprising at least one of the following germline VL regions: Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs834 (lambda) (SEQ ID NO:15).

In certain aspects the present disclosure provides a synthetic canine antibody library, wherein post-translational modification (PTM) sites are removed from one or more of the germline VH regions or the germline VL regions.

In certain aspects the present disclosure provides a synthetic canine antibody library, wherein said library comprises the VH regions: Vs618 (SEQ ID NO:4), Vs624-PTM-low (SEQ ID NO:6), Vs628-PTM-low (SEQ ID NO:10) and Vs635-PTM-low (SEQ ID NO:7) and the VL regions: Vs236 (kappa) (SEQ ID NO:12), Vs321 (lambda) (SEQ ID NO:14), Vs323-PTM-low (lambda) (SEQ ID NO:18), Vs365 (lambda) (SEQ ID NO:13) and Vs834 (lambda) (SEQ ID NO:15).

In certain aspects the present disclosure provides a synthetic canine antibody library, wherein said library comprises one or more of the following VH/VL combinations: the VHNL combination of the VH1 region Vs618 (SEQ ID NO:4) and the VL region Vs236 (kappa) (SEQ ID NO:12), the VH/VL combination of the VH1 region Vs624-PTM-low (SEQ ID NO:6) and the VL region Vs236 (kappa) (SEQ ID NO:12), the VH/VL combination of the VH1 region Vs635-PTM-low (SEQ ID NO:7) and the VL region Vs323-PTM-low (lambda) (SEQ ID NO:18), the VH/VL combination of the VH1 region Vs618 (SEQ ID NO:4) and the VL region Vs365 (lambda) (SEQ ID NO:13), the VH/VL combination of the VH1 region Vs624-PTM-low (SEQ ID NO:6) and the VL region Vs365 (lambda) (SEQ ID NO:13) and the VHNL combination of the VH1 region Vs635-PTM-low (SEQ ID NO:7) and the VL region Vs365 (lambda) (SEQ ID NO:13), the VH/VL combination of the VH1 region Vs618 (SEQ ID NO:4) and the VL region Vs843 (lambda) (SEQ ID NO:15), the VH/VL combination of the VH1 region Vs624-PTM-low (SEQ ID NO:6) and the VL region Vs843 (lambda) (SEQ ID NO:15), and the VH/VL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VH/VL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VHNL combination of the VH1 region Vs624-PTM-low (SEQ ID NO:6) and the VL region Vs321 (lambda) (SEQ ID NO:14), and the VH/VL combination of the VH1 region Vs635-PTM-low (SEQ ID NO:7) and the VL region Vs321 (lambda) (SEQ ID NO:14), and the VH/VL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VH/VL combination of the VH1 region Vs628-PTM-low (SEQ ID NO:10) and the VL region Vs843 (lambda) (SEQ ID NO:15).

In certain aspects the present disclosure provides a synthetic canine antibody library, wherein essentially all VH/VL combinations of said library are efficiently displayed at a display rate of at least 0.5 Fab per phage.

In certain aspects the present disclosure provides a synthetic canine antibody library, wherein essentially all VH/VL combinations have a monomeric content of at least 85% when expressed in *E. coli* in Fab format.

In certain aspects the present disclosure provides a synthetic canine antibody library, wherein essentially all VH/VL combinations have a monomeric content of at least 90% when expressed in a mammalian system in IgG format.

In certain aspects the present disclosure provides a synthetic canine antibody library, wherein all VHNL combinations are thermally stable. In certain aspects the present disclosure provides a collection of nucleic acid molecules encoding the members of aforementioned library.

In certain aspects the present disclosure provides a vector encoding aforementioned nucleic acid molecules.

In certain aspects the present disclosure provides a recombinant host cell comprising the aforementioned nucleic acid molecules or aforementioned vector.

In certain aspects the present disclosure provides a method to isolate an antibody specific for an antigen, said method comprising the steps of:
(a) contacting aforementioned library with an antigen;
(b) removing those members of the library which do not bind to the antigen; and
(c) recovering those members of the library bound to the antigen.

In certain aspects the present disclosure provides an antibody isolated from aforementioned library or isolated by aforementioned method.

In certain aspects the present disclosure provides a synthetic canine antibody library comprising members of germline VH regions selected from VH1.

In certain aspects the present disclosure provides a synthetic canine antibody library comprising members of at least one of the following VH1 regions: Vs618 (SEQ ID NO:4), Vs624-PTM-low (SEQ ID NO:6), Vs628-PTM-low (SEQ ID NO:10) and Vs635-PTM-low (SEQ ID NO:7).

In certain aspects the present disclosure provides a synthetic canine antibody library comprising members of germline VL regions selected from kappa V-Ill, lambda V-I, and lambda VAIII.

In certain aspects the present disclosure provides a synthetic canine antibody library comprising at least one of the following VL regions: Vs236 (kappa) (SEQ ID NO:12), Vs321 (lambda) (SEQ ID NO:14), Vs323-PTM-low (lambda) (SEQ ID NO:18), Vs365 (lambda) (SEQ ID NO:13) and Vs843 (lambda) (SEQ ID NO:15).

In certain aspects the present disclosure provides a synthetic canine antibody library comprising the VH regions: Vs618 (SEQ ID NO:4), Vs624-PTM-low (SEQ ID NO:6), Vs628-PTM-low (SEQ ID NO:10) and Vs635-PTM-low (SEQ ID NO:7) and the VL regions: Vs236 (kappa) (SEQ ID NO:12), Vs321 (lambda) (SEQ ID NO:14), Vs323-PTM-low (lambda) (SEQ ID NO:18), Vs365 (lambda) (SEQ ID NO:13) and Vs843 (lambda) (SEQ ID NO:15). In certain aspects the present disclosure provides a synthetic canine antibody library comprises VH/VL combinations selected from the VHNL combinations of the germline VH1 region Vs618 (SEQ ID NO:4) and the germline VL region Vs236 (kappa) (SEQ ID NO:12), the VHNL combination of the VH1 region Vs624-PTM-low (SEQ ID NO:6) and the germline VL region Vs236 (kappa) (SEQ ID NO:12), the VHNL combination of the VH1 region Vs635-PTM-low (SEQ ID NO:7) and the VL region Vs323-PTM-low (lambda) (SEQ ID NO:18), the VHNL combination of the germline VH1 region Vs618 (SEQ ID NO:4) and the germline VL region Vs365 (lambda) (SEQ ID NO:13), the VH/VL combination of the VH1 region Vs624-PTM-low (SEQ ID NO:6) and the germline VL region Vs365 (lambda) (SEQ ID NO:13) and the VH/VL combination of the VH1 region Vs635-PTM-low (SEQ ID NO:7) and the germline VL region Vs365 (lambda) (SEQ ID NO:13), the VHNL combination of the VH1 region Vs618 (SEQ ID NO:4) and the VL region Vs843 (lambda) (SEQ ID NO:15), the VH/VL combination of the VH1 region Vs624-PTM-low (SEQ ID NO:6) and the VL region Vs843 (lambda) (SEQ ID NO:15), and the VHNL combination of the VH1 region Vs635-PTM-low (SEQ ID NO:7) and the VL region Vs843 (lambda) (SEQ ID NO:15), the VH/VL combination of the VH1 region Vs618 (SEQ ID NO:4) and the VL region Vs323-PTM-low (lambda) (SEQ ID NO:18), the VHNL combination of the VH1 region Vs624-PTM-low (SEQ ID NO:6) and the VL region Vs323-PTM-low (lambda) (SEQ ID NO:18), the VHNL combination of the VH1 region Vs618 (SEQ ID NO:4) and the VL region Vs321 (lambda) (SEQ ID NO:14), the VH/VL combination of the VH1 region Vs624-PTM-low (SEQ ID NO:6) and the VL region Vs321 (lambda) (SEQ ID NO:14), and the VH/VL combination of the VH1 region Vs635-PTM-low (SEQ ID NO:7) and the VL region Vs321 (lambda) (SEQ ID NO:14), and the VH/VL combination of the VH1 region Vs635-PTM-low (SEQ ID NO:7) and the VL region Vs236 (kappa) (SEQ ID NO:12), the VHNL combination of the VH1 region Vs628-PTM-low (SEQ ID NO:10) and the VL region VS236 (kappa) (SEQ ID NO:12), the VHNL combination of the VH1 region Vs628-PTM-low (SEQ ID NO:10) and the VL region Vs365 (lambda) (SEQ ID NO:13), and the VHNL combination of the VH1 region Vs628-PTM-low (SEQ ID NO:10) and the VL region Vs843 (lambda) (SEQ ID NO:15).

In certain aspects the present disclosure provides a synthetic canine antibody library, wherein said library comprises H-CDR3s which cover more than 50% of the naturally occurring H-CDR3 lengths of the canine H-CDR3 repertoire.

In certain aspects the present disclosure provides a synthetic canine antibody library, wherein said library comprises H-CDR3s of the Kabat length of 5-16 amino acids.

In certain aspects the present disclosure provides a synthetic canine antibody library, wherein said library has an H-CDR3 design as shown in Table 4-Table 15.

In certain aspects the present disclosure provides a synthetic canine antibody library, wherein said library has a diversity of at least 5E+09 in the H-CDR3 region.

In certain aspects the present disclosure provides a synthetic canine antibody library, where the L-CDR3 of the library is of the Kabat length of 8 amino acids (kappa) and of the Kabat length 10 and 11 amino acids (lambda).

In certain aspects the present disclosure provides a synthetic canine antibody library, wherein said library has an L-CDR3 design as shown in Table 16 and Tables 17-18.

In certain aspects the present disclosure provides a synthetic canine antibody library, wherein said library has a diversity of at least 1E+04 in the L-CDR3 region.

In certain aspects the present disclosure provides a synthetic canine antibody library, wherein essentially all VH/VL combinations of said library are efficiently displayed.

In certain aspects the present disclosure provides a synthetic canine antibody library, wherein essentially all VH/VL combinations of said library are efficiently displayed, having a display rate of at least 0.5 Fab per phage.

In certain aspects the present disclosure provides a synthetic canine antibody library, wherein essentially all VH/VL combinations are expressed in *E. coli* in Fab format.

In certain aspects the present disclosure provides a synthetic canine antibody library, wherein essentially all VH/VL combinations expressed in *E. coli* in Fab format have a monomeric content of at least 85%.

In certain aspects the present disclosure provides a synthetic canine antibody library, wherein essentially all VH/VL combinations are expressed in a mammalian system in IgG format.

In certain aspects the present disclosure provides a synthetic canine antibody library, wherein essentially all VH/VL combinations expressed in a mammalian system in IgG format have a monomeric content of at least 90%.

In certain aspects the present disclosure provides a synthetic canine antibody library, wherein all VH/VL combinations are thermally stable.

In certain aspects the present disclosure provides a synthetic canine antibody library, wherein the H-CDR3 regions of essentially all members of the library are flanked by unique restriction sites.

In certain aspects the present disclosure provides a synthetic canine antibody library, wherein the L-CDR3 regions of essentially all members of the library are flanked by unique restriction sites.

In certain aspects the present disclosure provides a synthetic canine antibody library, wherein said library is an unbiased library.

TABLE 1

| | Germline variable region# | SEQ ID NO: | [aa]/DNA |
|---|---|---|---|
| VH (protein) | Vs624 (VH1-62) | SEQ ID NO: 1 | EVQLVESGGDLVKPAGSLRLSCVASGFTFS SYSMSWVRQAPEKGLQLVAGINSGGSSTYY TDAVKGRFTISRDNAKNTVYLQMNSLRAEDT AMYYC |
| | Vs635 (VH1-44) | SEQ ID NO: 2 | EVQLVESGGDLVKPGGTLRLSCVASGFTFS SYDMSWVRQSPGKGLQWVAVIWNDGSSTY YADAVKGRFTISRDNAKNTLYLQMNSLRAED TAVYYC |
| | Vs639 (VH1-21) | SEQ ID NO: 3 | EVQLVESGGNLVKPGGSLRLSCVASGLTFY SYAIYWVHEAPGKGLQWVAAITTDGSSTYYT DAVKGRFTISRDNAKNTLYLQMNSLRAEDM PVYYC |
| | Vs618 (VH1-73) | SEQ ID NO: 4 | EVQLVESGGDLVKPGGSLRLSCVASGFTFS NYEMYWVRQAPGKGLEWVARIYESGSTTY YAEAVKGRFTISRDNAKNMAYLQMNSLRAE DTAVYYC |
| | Vs628 (VH1-51) | SEQ ID NO: 5 | EVQLVQSGAEVKKPGASVKVSCKTSGYTFIN YYMIWVRQAPGAGLDWMGQIDPEDGATSY AQKFQGRVTLTADTSTSTAYMELSSLRAGDI AVYYC |
| | Vs624-PTM-low | SEQ ID NO: 6 | EVQLVESGGDLVKPAGSLRLSCVASGFTFS SYSMSWVRQAPEKGLQLVAGISSGGSSTYY TDAVKGRFTISRDNAKNTVYLQMNSLRAEDT AMYYC |
| | Vs635-PTM-low | SEQ ID NO: 7 | EVQLVESGGDLVKPGGTLRLSCVASGFTFS SYDMSWVRQSPGKGLQWVAVIWNEGSSTY YADAVKGRFTISRDNAKNTLYLQMNSLRAED TAVYYC |
| | Vs639-PTM-low | SEQ ID NO: 8 | EVQLVESGGNLVKPGGSLRLSCVASGLTFY SYAIYWVHEAPGKGLQWVAAITTGGSSTYY TDAVKGRFTISRDNAKNTLYLQMNSLRAED MPVYYC |
| | Vs618-PTM-low | SEQ ID NO: 9 | equal to SEQ ID NO: 4 |
| | Vs628-PTM-low | SEQ ID NO: 10 | EVQLVQSGAEVKKPGASVKVSCKTSGYTFIN YYMIWVRQAPGAGLDWMGQIDPEGGATSY AQKFQGRVTLTADTSTSTAYMELSSLRAGDI AVYYC |
| VL (protein) | Vs744 | SEQ ID NO: 11 | DIVMTQTPLSLSVSPGEPASISCKASQSLLHS NGNTYLYWFRQKPGQSPQRLIYKVSNRDPG VPDRFSGSGSGTDFTLRISRVEAEDAGVYY C |
| | Vs236 | SEQ ID NO: 12 | EIVMTQSPASLSLSQEEKVTITCRASQSVSS YLAWYQQKPGQAPKLLIYGTSNRATGVPSR FSGSGSGTDFSFTISSLEPEDVAVYYC |
| | Vs365 | SEQ ID NO: 13 | SYVLTQLPSVSVTLRQTARITCGGDSIGSKN VYWYQQKLGQAPVLIIYDDSSRPSGIPERFS GANSGNTATLTISGALAEDEADYYC |
| | Vs321 | SEQ ID NO: 14 | QTVVTQEPSLSVSPGGTVTLTCGLSSGSVS TSNYPGWYQQTLGRAPRTIIYRTSSRPSGVP NRFSGSISGNKAALTITGAQPEDEADYYC |
| | Vs843 | SEQ ID NO: 15 | QSVLTQPASVSGSLGQRVTISCTGSSSNVG YGNYVGWYQQLPGTGPRTLIYRSSSRPSGV PDRFSGSRSGSTATLTISGLQAEDEADYYC |
| | Vs323 | SEQ ID NO: 16 | QSVLTQPASVSGSLGQRVTISCTGSSSNIGR GYVGWYQQLPGTGPRTLIYGNSNRPSGVP DRFSGSRSGSTATLTISGLQAEDEADYYC |
| | Vs744-PTM-low | SEQ ID NO: 17 | DIVMTQTPLSLSVSPGEPASISCKASQSLLHS SGNTYLYWFRQKPGQSPQRLIYKVSNRDPG VPDRFSGSGSGTDFTLRISRVEAEDAGVYY C |

TABLE 1-continued

| | Germline variable region# | SEQ ID NO: | [aa]/DNA |
|---|---|---|---|
| | Vs323-PTM-low | SEQ ID NO: 18 | QSVLTQPASVSGSLGQRVTISCTGSSSNIGR GYVGWYQQLPGTGPRTLIYGISNRPSGVPD RFSGSRSGSTATLTISGLQAEDEADYYC |
| VH (DNA) | Vs624(VH1-62) | SEQ ID NO: 19 | gaagtgcaattggtggaaagcggtggcgatctggtgaaacc agccggcagcctgcgcctgagctgcgtggccagcggctttac ctttagcagctatagcatgagctgggttcgccaggccccgga aaaaggcctgcagctggtggccggcattAATagggcggc agcagcaccttattataccgatgccgtgaaaggccgctttacca ttagccgcgataacgccaaaaacaccgtgtacctgcagatg aacagcctgcgggccgaagataccgccatgtattattgc |
| | Vs635 (VH1-44) | SEQ ID NO: 20 | gaagtgcaattggttgaaagcggtggtgatctggttaaaccgg gtggcaccctgcgtctgagctgtgttgcaagcggtttttacctta gcagctatgatatgagctgggtgcgccagagtccgggtaaag gtctgcagtggggttgcagttatttggaatGATggtagcagcac ctattatgcagatgcagttaaagggcgttttaccattagccgtga taatgccaaaaatacctgtatctgcagatgaatagcctgcgt gcagaggataccgcagtgtattattgc |
| | Vs639 (VH1-21) | SEQ ID NO: 21 | gaagtgcaattggttgaaagcggtggtaatctggttaaaccgg gtggtagcctgcgtctgagctgtgttgcaagcggtctgaccttt atagctatgcaatttattgggtgcacgaagcaccgggaaaag gtctgcagtggggttgcagcaattaccaccGATggcagcagc acctattacaccgatgcagttaaagggcgttttaccattagccg tgataatgccaaaaatacctgtatctgcagatgaatagcctg cgtgcagaggatatgccggtgtattattgc |
| | Vs618 (VH1-73) | SEQ ID NO: 22 | gaagtgcaattggttgaaagcggtggtgatctggttaaaccgg gtggtagcctgcgtctgagctgtgttgcaagcggttttaccttag caactatgaaatgtattgggtgcggcaggcaccgggtaaag gtctggaatggggttgcacgcatttatgaaagcggtagcaccac ctattatgcagaagcagttaaagggcgttttaccattagccgtg ataacgccaaaaatatggcatatctgcagatgaatagcctgc gtgcagaggataccgcagtgtattattgc |
| | Vs628 (VH1-51) | SEQ ID NO: 23 | gaagtgcaattggttcagagcggtgccgaagttaaaaaacc gggtgcaagcgttaaagttagctgtaaaaccagcggctatac cttcatcaactattatatgatttgggtgcgccaggcaccgggtg caggtctggattggatgggtcagattgatccggaaGAAggt gcaaccagctatgcacagaaatttcagggtcgtgttaccctga ccgcagataccagcaccagcaccgcatatatggaactgagc agcctgcgtgccggtgatattgcagtgtattattgc |
| | Vs624-PTM-low | SEQ ID NO:24 | gaagtgcaattggtggaaagcggtggcgatctggtgaaacc agccggcagcctgcgcctgagctgcgtggccagcggctttac ctttagcagctatagcatgagctgggttcgccaggccccgga aaaaggcctgcagctggtggccggcattagcagcggcggc agcagcaccttattataccgatgccgtgaaaggccgctttacca ttagccgcgataacgccaaaaacaccgtgtacctgcagatg aacagcctgcgggccgaagataccgccatgtattattgc |
| | Vs635-PTM-low | SEQ ID NO: 25 | gaagtgcaattggttgaaagcggtggtgatctggttaaaccgg gtggcaccctgcgtctgagctgtgttgcaagcggtttttaccttta gcagctatgatatgagctgggtgcgccagagtccgggtaaag gtctgcagtggggttgcagttatttggaatgaaggtagcagcac ctattatgcagatgcagttaaagggcgttttaccattagccgtga taatgccaaaaatacctgtatctgcagatgaatagcctgcgt gcagaggataccgcagtgtattattgc |
| | Vs639-PTM-low | SEQ ID NO: 26 | gaagtgcaattggttgaaagcggtggtaatctggttaaaccgg gtggtagcctgcgtctgagctgtgttgcaagcggtctgaccttt atagctatgcaatttattgggtgcacgaagcaccgggaaaag gtctgcagtggggttgcagcaattaccaccggtggcagcagca cctattacaccgatgcagttaaagggcgttttaccattagccgt gataatgccaaaaatacctgtatctgcagatgaatagcctgc gtgcagaggatatgccggtgtattattgc |
| | Vs618-PTM-low | SEQ ID NO: 27 | Equal to SEQ ID NO: 22 |
| | Vs628-PTM-low | SEQ ID NO: 28 | gaagtgcaattggttcagagcggtgccgaagttaaaaaacc gggtgcaagcgttaaagttagctgtaaaaccagcggctatac cttcatcaactattatatgatttgggtgcgccaggcaccgggtg caggtctggattggatgggtcagattgatccggaaggtggtgc aaccagctatgcacagaaatttcagggtcgtgttaccctgacc gcagataccagcaccagcaccgcatatatggaactgagca gcctgcgtgccggtgatattgcagtgtattattgc |
| VL (DNA) | Vs744 (kappa) | SEQ ID NO: 29 | gatattgtgatgacccagaccccactgagcctgagcgtgagc ccaggcgaaccagccagcattagctgcaaagccagcaga gcctgctgcatagcAATggcaacacctatctgtattggtttcg ccagaaaccaggccagagcccacagcgcctgatctataaa gtgagcaaccgcgatccaggcgtgccggatcgctttagcggc agcggtagcggcaccgattttaccctgcgcattagtcgcgtgg aagccgaagacgcaggcgtgtattattgc |

TABLE 1-continued

| Germline variable region# | SEQ ID NO: | [aa]/DNA |
|---|---|---|
| Vs236 (kappa) | SEQ ID NO: 30 | gaaattgttatgacccagagtccggcaagcctgagcctgagccaagaagaaaaagttaccattacctgtcgtgcaagccagagcgttagcagctatctggcatggtatcagcagaaaccgggtcaggcaccgaaactgctgatttatggcaccagcaatcgtgcaaccggtgttccgagccgttttagcggtagcggtagtggcaccgattttagctttaccattagcagcctggaaccggaagacgtggccgtgtattattgc |
| Vs365 (lambda) | SEQ ID NO: 31 | agctatgtgctgacccagctgccgagcgtgagcgtgaccctgcgccagaccgcacgcattacctgcggtggcgatagcattggcagcaaaaacgtgtattggtatcagcagaaactgggccaggcaccggtgctgattatctatgatgatagcagtcgcccaagcggcattccggaacgctttagcggtgccaacagcggcaacaccgccaccctgaccattagcggtgccctggccgaagacgaagccgattattactgc |
| Vs321 (lambda) | SEQ ID NO: 32 | cagaccgttgttacccaagaaccgagcctgagcgttagtccgggtggcaccgttacccctgacctgtggtctgagcagcggtagcgttagcaccagcaattatccagggtggtatcagcagacccctggtcgtgcaccgcgtaccattatctatcgtaccagcagccgtcgagcggtgttccgaatcgttttagcggtagcattagcggtaataaagcagcactgaccattaccggtgcacagccggaagacgaagccgattattactgc |
| Vs843 (lambda) | SEQ ID NO: 33 | cagagcgttctgacccagcctgcaagcgttagcggtagcctgggtcagcgtgttaccattagctgtaccggtagtagtagcaatgttggttatggtaattatgttggttggtatcagcagctgcctggcaccggtccgcgtaccctgatttatcgtagcagcagccgtccgagcggtgttccggatcgttttagcggtagtcgtagcggtagcaccgcaaccctgaccattagcggtctgcaggcagaagacgaagccgattattactgc |
| Vs323 (lambda) | SEQ ID NO: 34 | cagagcgttctgacccagcctgcaagcgttagcggtagcctgggtcagcgtgttaccattagctgtaccggtagtagcagcaatattggtcgtggttatgttggttggtatcagcagctgcctggcaccggtccgcgtaccctgatttatggtAATagcaatcgtccgagcggtgttccggatcgttttagcggtagtcgtagcggtagcaccgcaaccctgaccattagcggtctgcaggcagaagacgaagccgattattactgc |
| Vs744-PTM-low | SEQ ID NO: 35 | gatattgtgatgacccagaccccactgagcctgagcgtgagcccaggcgaaccagccagcattagctgcaaagccagccagagcctgctgcatagcagcggcaacacctatctgtattggtttcgcagaaaaccaggccagagcccacagcgcctgatctataaagtgagcaaccgcgatccaggcgtgccggatcgctttagcggcagcggtagcggcaccgattttaccctgcgcattagtcgcgtggaagccgaagacgcaggcgtgtattattgc |
| Vs323-PTM-low | SEQ ID NO: 36 | cagagcgttctgacccagcctgcaagcgttagcggtagcctgggtcagcgtgttaccattagctgtaccggtagtagcagcaatattggtcgtggttatgttggttggtatcagcagctgcctggcaccggtccgcgtaccctgatttatggtattagcaatcgtccgagcggtgttccggatcgttttagcggtagtcgtagcggtagcaccgcaaccctgaccattagcggtctgcaggcagaagacgaagccgattattactgc |

TABLE 2

| | | SEQ ID NO: | |
|---|---|---|---|
| J (FR4) (Protein) | JH | SEQ ID NO: 37 | WGQGTLVTVSS |
| | Jkappa | SEQ ID NO: 38 | FGAGTKVELK |
| | Jlambda | SEQ ID NO: 39 | FGGGTQLTVL |
| J (FR4) (DNA) | JH | SEQ ID NO: 40 | tggggccagggcaccctggttaccgtctcgagc |
| | Jkappa | SEQ ID NO: 41 | tttggcgcaggtaccaaagtggaactgaaa |
| | Jlambda | SEQ ID NO: 42 | tttggcggtggtacccagctgaccgtgctg |

TABLE 3

| ID | Light chain type | VH | VL | Fab Expression [mg/L] | Fab Monomer [%] | IgG Expression [mg/L] | IgG Monomer content [%] |
|---|---|---|---|---|---|---|---|
| 1A | kappa | Vs624-PTM-low | Vs744-PTM-low | 0.7 | 89.3 | 3.0 | 97 |
| 1B | kappa | Vs635-PTM-low | Vs744-PTM-low | 0.3 | | 12.1 | 97.1 |
| 1C | kappa | Vs639-PTM-low | Vs744-PTM-low | 0.4 | | 0.0 | |
| 1D | kappa | Vs618 | Vs744-PTM-low | 0.3 | | 15.1 | 85.7 |
| 1E | kappa | Vs628-PTM-low | Vs744-PTM-low | 0.2 | | 0.0 | |
| 2A | kappa | Vs624-PTM-low | Vs236 | 2.8 | 89.8 | 12.1 | 98 |
| 2B | kappa | Vs635-PTM-low | Vs236 | 0.6 | 83.9 | 54.3 | 98.6 |

TABLE 3-continued

| ID | Light chain type | VH | VL | Fab Expression [mg/L] | Fab Monomer [%] | IgG Expression [mg/L] | IgG Monomer content [%] |
|---|---|---|---|---|---|---|---|
| 2C | kappa | Vs639-PTM-low | Vs236 | 0.2 | | 0.0 | |
| 2D | kappa | Vs618 | Vs236 | 2.2 | 89.1 | 57.3 | 98.2 |
| 2E | kappa | Vs628-PTM-low | Vs236 | 1.1 | 90.6 | 3.0 | 98.3 |
| 3A | lambda | Vs624-PTM-low | Vs365 | 1.9 | 85.9 | 15.1 | 97.9 |
| 3B | lambda | Vs635-PTM-low | Vs365 | 1.4 | 90.0 | 57.3 | 98.5 |
| 3C | lambda | Vs639-PTM-low | Vs365 | 0.3 | | 0.0 | |
| 3D | lambda | Vs618 | Vs365 | 3.7 | 94.8 | 69.4 | 98.7 |
| 3E | lambda | Vs628-PTM-low | Vs365 | 1.1 | 89.1 | 6.0 | 98.4 |
| 4A | lambda | Vs624-PTM-low | Vs321 | 6.1 | 93.0 | 0.0 | |
| 4B | lambda | Vs635-PTM-low | Vs321 | 3.0 | 94.6 | 3.0 | |
| 4C | lambda | Vs639-PTM-low | Vs321 | 0.2 | | 0.0 | |
| 4D | lambda | Vs618 | Vs321 | 6.3 | 93.0 | 3.0 | 98.2 |
| 4E | lambda | Vs628-PTM-low | Vs321 | 0.6 | 71.3 | 0.0 | |
| 5A | lambda | Vs624-PTM-low | Vs843 | 4.5 | 95.3 | 0.0 | |
| 5B | lambda | Vs635-PTM-low | Vs843 | 1.6 | 93.9 | 3.0 | 98.6 |
| 5C | lambda | Vs639-PTM-low | Vs843 | 0.3 | | 0.0 | |
| 5D | lambda | Vs618 | Vs843 | 6.3 | 91.9 | 6.0 | 98.7 |
| 5E | lambda | Vs628-PTM-low | Vs843 | 0.6 | 83.5 | 0 0 | |
| 6A | lambda | Vs624-PTM-low | Vs323-PTM-low | 4.8 | 93.2 | 0.0 | |
| 6B | lambda | Vs635-PTM-low | Vs323-PTM-low | 3.2 | 95.3 | 3.0 | 99.4 |
| 6C | lambda | Vs639-PTM-low | Vs323-PTM-low | 0.3 | | 0.0 | |
| 6D | lambda | Vs618 | Vs323-PTM-low | 7.3 | 92.5 | 6.0 | 98.4 |
| 6E | lambda | Vs628-PTM-low | Vs323-PTM-low | 0.6 | 77.7 | 0.0 | |

EXAMPLES

Example 1: Generation of a Synthetic Canine Antibody Library

The present disclosure provides a collection or library of antibody candidates comprising canine VH and VL gene pairs present in the canine immune repertoire, wherein each member comprises germline gene sequences or modified germline sequences (referred to as PTM-low) to remove unfavorable post-translational modification (PTM) sites to further optimize antibody expression and biophysical properties. The VH and VL pairs selected for incorporation into the library comprise advantageous biophysical properties that increase the likelihood that each of the antibodies selected from the library will be conveniently developable. In order to determine the composition of the library, multiple criteria had to be evaluated. The following examples describe the criteria evaluated, methods of evaluating and results.

Example 1.1: Selection of Candidate VL- and VH-Qermline Sequences

Figure 1:
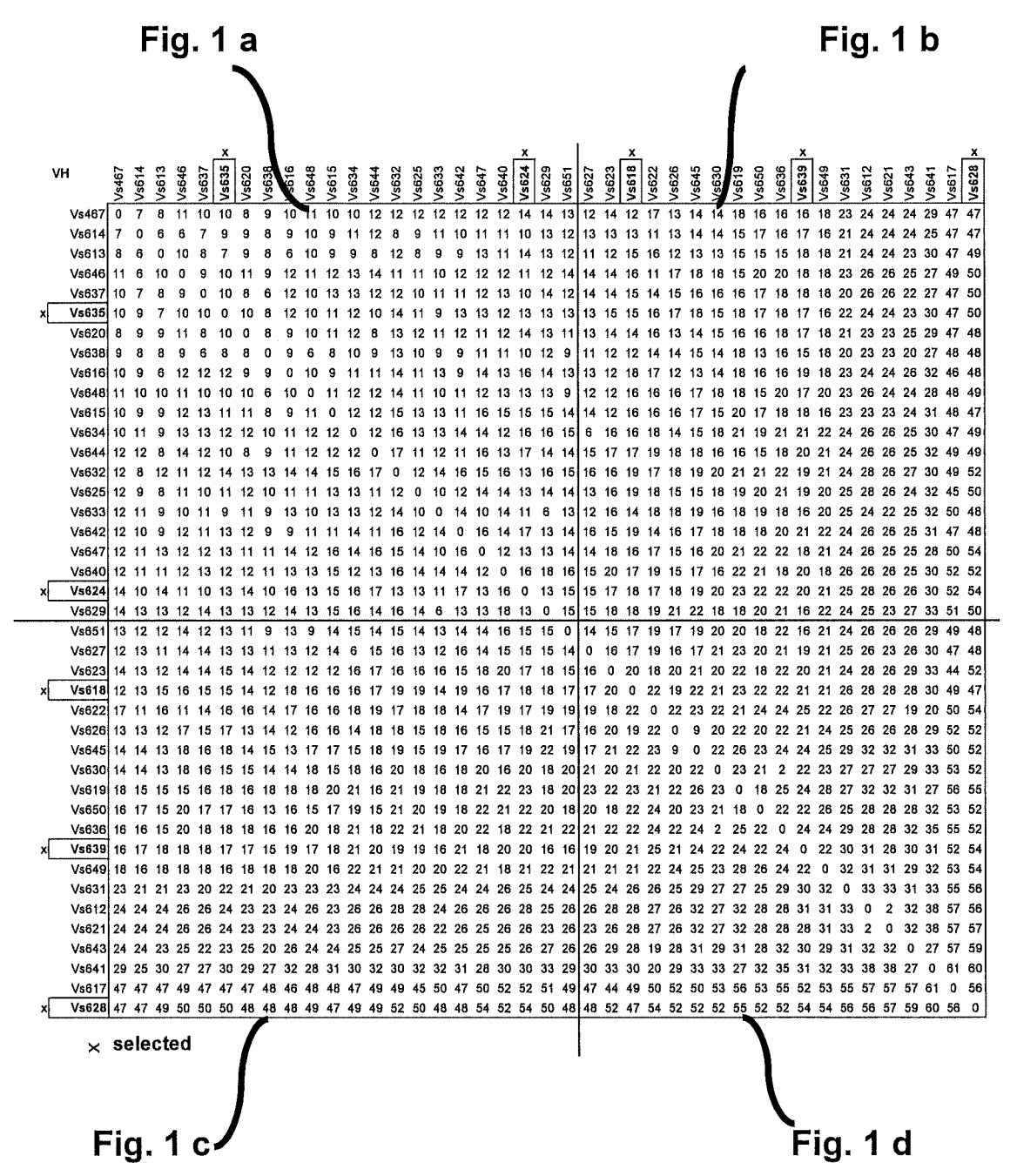
Figure 2:
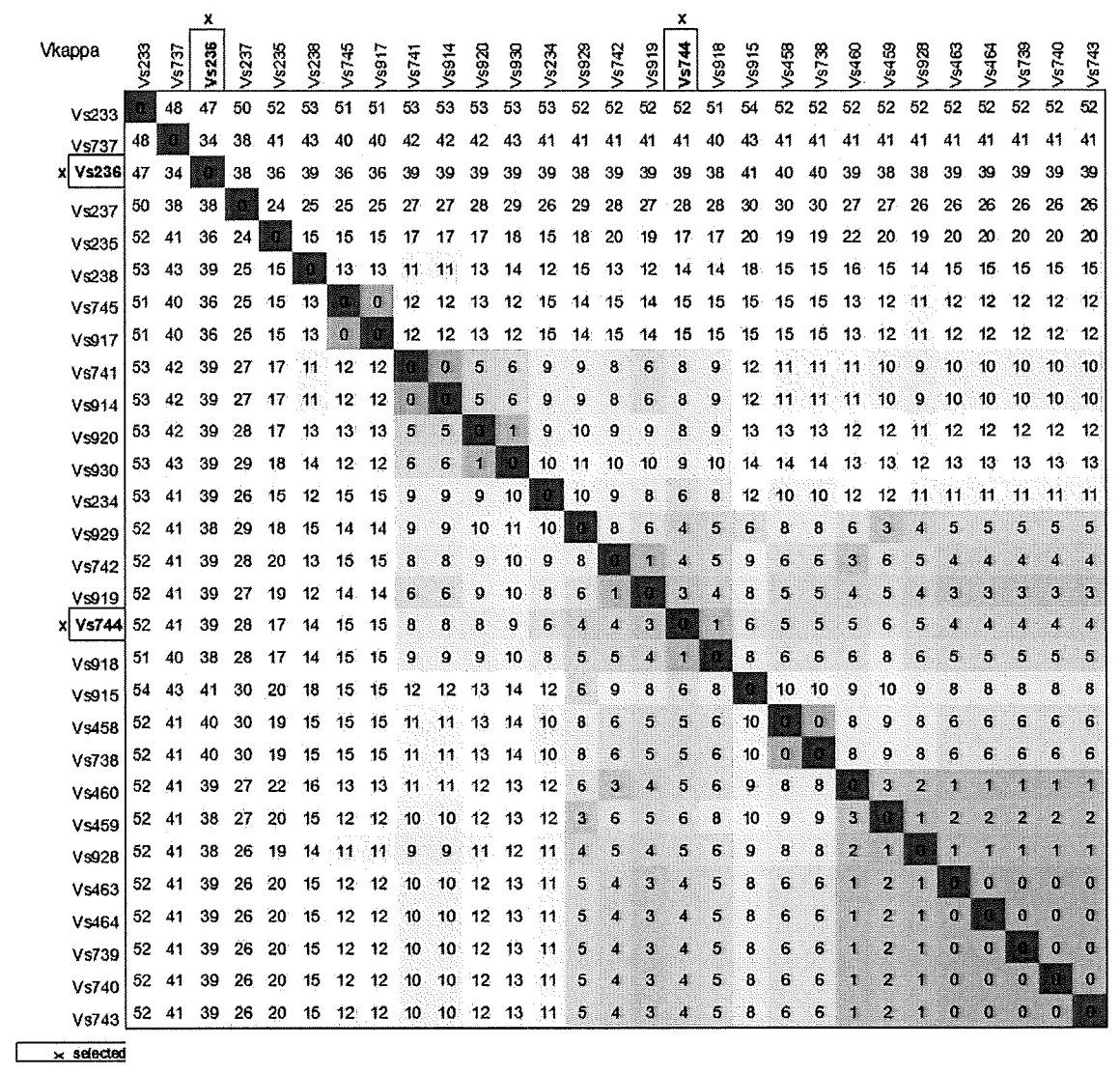

In a first step, predominant VH and VL germline genes from the canine immune repertoire were identified from the literature (Bao et al. Vet Immunol Immunopathol. 2010 Sep. 15; 137 (1-2):64-75; Steiniger et al. Mol Immunol. 2014 May; 59(1):71-8) and by analysis of re-arranged canine antibody sequences available from Bao et al. (Vet Immunol Immunopathol. 2010 September; 137 (1-2):64-75), Braganza et al. (Vet Immunol Immunopathol. 2011 January; 139(1):27-40), Vgenerepertoire.org and AbYsis (http with the extension bioinf.org.uk/abysis2.7/index.html of the world wide web). In total, more than 300 re-arranged canine VH, >100 Vkappa and >150 Vlambda sequences were analyzed. Since it has been recognized that for efficient antigen-antibody interaction a broad conformation-space might be beneficial, care was taken to include structurally different sequences in the final selection. Thus, in a second step, structurally diverse VH and VL (Vkappa and Vlambda) genes from the canine germline repertoire were identified by distance analysis. Results are shown in FIGS. 1, 2 and 3.

V regions with flanking sites for restriction enzymes were synthesized by GeneArt with CDR-H3 (WGGDGFYAMDY) (SEQ ID NO:43) and kappa CDR-L3 (QQHYTTPPT) (SEQ ID NO: 44) of the hu4D5-8 antibody and lambda-like CDR-L3 (QSYDSSLSGW) (SEQ ID NO: 45) sequences and the canine JH, Jkappa and Jlambda germline protein sequences (see Table 2), respectively. Codon usage optimization with respect to E. coli expression (avoiding rare human codons), avoidance of regions of very high (>80%) or very low (<30%) GC content and removal of potential cis-acting sequence motifs such as RNA instability motifs and cryptic splice donor and acceptor sites were performed by GeneArt. The synthesized Ig V region heavy chain genes covered the full sequences from the first amino acids (EVQL) (SEQ ID NO:46) containing a unique 5' restriction site for MfeI to the unique 3' restriction site for XhoI located at the V to C region border. Upstream from the CDR-H3, a restriction site for BssHII was incorporated to enable subsequent CDR-H3 library insertion. The Ig Vkappa and Vlambda region light chain gene sequences ranged from the first unique 5' restriction site for NdeI located in the modified ompA leader sequence to the 3' restriction sites for Acc65I/KpnI in framework region (FR4). Upstream from the CDR-L3, a restriction site for BbsI was incorporated to enable subsequent CDR-L3 library insertion. Then VH/VL gene pairs were combined from 5 selected VH, 4 Vlambda and 2 Vkappa genes creating 30 VH/VL combinations. The 5 VH region constructs (constructs A—E) were cloned together with 2 Vkappa region constructs (#1-#2) or 4 Vlambda region constructs (#3-#6) into the phage display vector pCaDis18 (gIII—Fab genetic fusion) (see FIG. 9) and the bacterial Fab expression vector pCaBx_FH (see FIG. 10) using standard molecular biology methods. All retained combinations were sequence verified. Finally, these 30 VH/VL pairs were experimentally compared to identify the subset of VH/VL gene pairs having favourable biophysical properties. At least the following properties were evaluated: 1) in silico analysis: a) CDR1+CDR2 length; b) post translational modification motifs (PTMs); c) the presence of Methionines in the CDRs; d) the presence of Cysteines; 2) Fab display rates; 3) Fab and IgG expression rates and yields; 4) Fab and IgG monomer content.

Example 1.2: Design of Canine H-CDR3s

The sites of the closest contact between antibody and antigen are the complementary determining regions (CDR) of the antibody. H-CDR3 and L-CDR3 are playing major roles in antigen-binding, thus variability was mainly introduced into these two CDRs. For all other CDRs, germline sequences or modified germline sequences with removed PTM motifs were used.

Cysteine residues were generally avoided in the design of the CDR3s because cysteine residues can be engaged in the formation of disulfide bonds covalently linking a binder with the panning target or in formation of antibody homodimers. Such binders are unlikely to be target-selective.

Re-arranged antibody-sequences were compiled and H-CDR3 and L-CDR3s analysed for design of canine CDR3s. The analysis of the H-CDR3 was done for all re-arranged sequences irrespective of the VH germline family, since H-CDR3 is encoded VH-independent by the D- and J-segment.

Our amino acid distribution analysis confirmed as described the most frequent amino acid motifs in the canine VH CDR3 to be CAR/CAK at IMGT position 104-106 (Chothia positions 92-94)-, and for the positions IMGT 115-117 (Chothia positions 100x-94) the FDY motif (Steiniger Molecular Immunology 59 (2014) 71-78).

The observed amino acid distribution was slightly modified to finalize the design of the H-CDR3 lengths 5 to 16 amino acids in the library (see Tables 4 to 15), e.g. by complete avoidance of cysteines, reduced usage of tryptophan and avoidance of glycosylation-sites (NxS, NxT).

TABLE 4

| L = 5aa pos | 93 | 94 | mix H1 95 | mix H2 96 | mix H4 100x | mix H5 101 | mix H6 102 |
|---|---|---|---|---|---|---|---|
| D | | | 5 | 2 | 0 | 90 | 0 |
| E | | | 5 | 4 | 0 | 0 | 0 |
| K | | | 0 | 5 | 0 | 0 | 0 |
| R | | 100 | 5 | 10 | 0 | 0 | 0 |
| H | | | 5 | 4 | 0 | 0 | 5 |
| T | | | 5 | 4 | 0 | 0 | 0 |
| S | | | 7.5 | 15 | 0 | 0 | 0 |
| N | | | 0 | 0 | 0 | 0 | 0 |
| Q | | | 5 | 2 | 0 | 0 | 0 |
| G | | | 22.5 | 15 | 5 | 5 | 0 |
| A | 100 | | 7.5 | 5 | 5 | 5 | 0 |
| C | | | 0 | 0 | 0 | 0 | 0 |
| P | | | 2.5 | 5 | 0 | 0 | 5 |
| V | | | 10 | 4 | 5 | 0 | 5 |
| I | | | 5 | 4 | 5 | 0 | 5 |
| L | | | 5 | 4 | 15 | 0 | 5 |
| M | | | 0 | 0 | 10 | 0 | 0 |
| F | | | 5 | 5 | 50 | 0 | 5 |
| Y | | | 5 | 10 | 5 | 0 | 70 |
| W | | | 0 | 2 | 0 | 0 | 0 |
| sum | 100 | 100 | 100 | 100 | 100 | 100 | 100 |
| # of aa | 1 | 1 | 15 | 17 | 8 | 3 | 7 |

TABLE 5

| L = 6aa pos | 93 | 94 | mix H1 95 | mix H2 96 | mix H2 97 | mix H4 100x | mix H5 101 | mix H6 102 |
|---|---|---|---|---|---|---|---|---|
| D | | | 5 | 2 | 2 | 0 | 90 | 0 |
| E | | | 5 | 4 | 4 | 0 | 0 | 0 |
| K | | | 0 | 5 | 5 | 0 | 0 | 0 |
| R | | 100 | 5 | 10 | 10 | 0 | 0 | 0 |
| H | | | 5 | 4 | 4 | 0 | 0 | 5 |
| T | | | 5 | 4 | 4 | 0 | 0 | 0 |
| S | | | 7.5 | 15 | 15 | 0 | 0 | 0 |
| N | | | 0 | 0 | 0 | 0 | 0 | 0 |
| Q | | | 5 | 2 | 2 | 0 | 0 | 0 |
| G | | | 22.5 | 15 | 15 | 5 | 5 | 0 |
| A | 100 | | 7.5 | 5 | 5 | 5 | 5 | 0 |
| C | | | 0 | 0 | 0 | 0 | 0 | 0 |
| P | | | 2.5 | 5 | 5 | 0 | 0 | 5 |
| V | | | 10 | 4 | 4 | 5 | 0 | 5 |
| I | | | 5 | 4 | 4 | 5 | 0 | 5 |
| L | | | 5 | 4 | 4 | 15 | 0 | 5 |
| M | | | 0 | 0 | 0 | 10 | 0 | 0 |
| F | | | 5 | 5 | 5 | 50 | 0 | 5 |
| Y | | | 5 | 10 | 10 | 5 | 0 | 70 |
| W | | | 0 | 2 | 2 | 0 | 0 | 0 |
| sum | 100 | 100 | 100 | 100 | 100 | 100 | 100 | 100 |
| # of aa | 1 | 1 | 15 | 17 | 17 | 8 | 3 | 7 |

TABLE 6

| L = 7aa Pos | 93 | 94 | mix H1 95 | mix H2 96 | mix H2 97 | mix H2 98 | mix H4 100x | mix H5 101 | mix H6 102 |
|---|---|---|---|---|---|---|---|---|---|
| D | | | 5 | 2 | 2 | 2 | 0 | 90 | 0 |
| E | | | 5 | 4 | 4 | 4 | 0 | 0 | 0 |
| K | | | 0 | 5 | 5 | 5 | 0 | 0 | 0 |
| R | | 100 | 5 | 10 | 10 | 10 | 0 | 0 | 0 |
| H | | | 5 | 4 | 4 | 4 | 0 | 0 | 5 |
| T | | | 5 | 4 | 4 | 4 | 0 | 0 | 0 |
| S | | | 7.5 | 15 | 15 | 15 | 0 | 0 | 0 |
| N | | | 0 | 0 | 0 | 0 | 0 | 0 | 0 |
| Q | | | 5 | 2 | 2 | 2 | 0 | 0 | 0 |
| G | | | 22.5 | 15 | 15 | 15 | 5 | 5 | 0 |
| A | 100 | | 7.5 | 5 | 5 | 5 | 5 | 5 | 0 |
| C | | | 0 | 0 | 0 | 0 | 0 | 0 | 0 |
| P | | | 2.5 | 5 | 5 | 5 | 0 | 0 | 5 |
| V | | | 10 | 4 | 4 | 4 | 5 | 0 | 5 |
| I | | | 5 | 4 | 4 | 4 | 5 | 0 | 5 |
| L | | | 5 | 4 | 4 | 4 | 15 | 0 | 5 |
| M | | | 0 | 0 | 0 | 0 | 10 | 0 | 0 |
| F | | | 5 | 5 | 5 | 5 | 50 | 0 | 5 |
| Y | | | 5 | 10 | 10 | 10 | 5 | 0 | 70 |
| W | | | 0 | 2 | 2 | 2 | 0 | 0 | 0 |
| sum | 100 | 100 | 100 | 100 | 100 | 100 | 100 | 100 | 100 |
| # of aa | 1 | 1 | 15 | 17 | 17 | 17 | 8 | 3 | 7 |

TABLE 7

| L = 8aa pos | 93 | 94 | mix H1 95 | mix H2 96 | mix H2 97 | mix H2 98 | mix H3 99 | mix H4 100x | mix H5 101 | mix H6 102 |
|---|---|---|---|---|---|---|---|---|---|---|
| D | | | 5 | 2 | 2 | 2 | 2 | 0 | 90 | 0 |
| E | | | 5 | 4 | 4 | 4 | 4 | 0 | 0 | 0 |
| K | | | 0 | 5 | 5 | 5 | 5 | 0 | 0 | 0 |
| R | | 100 | 5 | 10 | 10 | 10 | 5 | 0 | 0 | 0 |
| H | | | 5 | 4 | 4 | 4 | 4 | 0 | 0 | 5 |
| T | | | 5 | 4 | 4 | 4 | 4 | 0 | 0 | 0 |
| S | | | 7.5 | 15 | 15 | 15 | 12.5 | 0 | 0 | 0 |
| N | | | 0 | 0 | 0 | 0 | 0 | 0 | 0 | 0 |
| Q | | | 5 | 2 | 2 | 2 | 2 | 0 | 0 | 0 |
| G | | | 22.5 | 15 | 15 | 15 | 15 | 5 | 5 | 0 |
| A | 100 | | 7.5 | 5 | 5 | 5 | 5 | 5 | 5 | 0 |

TABLE 7-continued

| L = 8aa pos | 93 | 94 | mix H1 95 | mix H2 96 | mix H2 97 | mix H2 98 | mix H3 99 | mix H4 100x | mix H5 101 | mix H6 102 |
|---|---|---|---|---|---|---|---|---|---|---|
| C |  |  | 0 | 0 | 0 | 0 | 0 | 0 | 0 | 0 |
| P |  |  | 2.5 | 5 | 5 | 5 | 5 | 0 | 0 | 5 |
| V |  |  | 10 | 4 | 4 | 4 | 4 | 5 | 0 | 5 |
| I |  |  | 5 | 4 | 4 | 4 | 4 | 5 | 0 | 5 |
| L |  |  | 5 | 4 | 4 | 4 | 4 | 15 | 0 | 5 |
| M |  |  | 0 | 0 | 0 | 0 | 0 | 10 | 0 | 0 |
| F |  |  | 5 | 5 | 5 | 5 | 5 | 50 | 0 | 5 |
| Y |  |  | 5 | 10 | 10 | 10 | 17.5 | 5 | 0 | 70 |
| W |  |  | 0 | 2 | 2 | 2 | 2 | 0 | 0 | 0 |
| sum |  | 100 | 100 | 100 | 100 | 100 | 100 | 100 | 100 | 100 |
| # of aa |  | 1 | 1 | 15 | 17 | 17 | 17 | 17 | 8 | 3 | 7 |

TABLE 8

| L = 9aa pos | 93 | 94 | mix H1 95 | mix H2 96 | mix H2 97 | mix H2 98 | mix H3 99 | mix H3 100 | mix H4 100x | mix H5 101 | mix H6 102 |
|---|---|---|---|---|---|---|---|---|---|---|---|
| D |  |  | 5 | 2 | 2 | 2 | 2 | 2 | 0 | 90 | 0 |
| E |  |  | 5 | 4 | 4 | 4 | 4 | 4 | 0 | 0 | 0 |
| K |  |  | 0 | 5 | 5 | 5 | 5 | 5 | 0 | 0 | 0 |
| R |  | 100 | 5 | 10 | 10 | 10 | 5 | 5 | 0 | 0 | 0 |
| H |  |  | 5 | 4 | 4 | 4 | 4 | 4 | 0 | 0 | 5 |
| T |  |  | 5 | 4 | 4 | 4 | 4 | 4 | 0 | 0 | 0 |
| S |  |  | 7.5 | 15 | 15 | 15 | 12.5 | 12.5 | 0 | 0 | 0 |
| N |  |  | 0 | 0 | 0 | 0 | 0 | 0 | 0 | 0 | 0 |
| Q |  |  | 5 | 2 | 2 | 2 | 2 | 2 | 0 | 0 | 0 |
| G |  |  | 22.5 | 15 | 15 | 15 | 15 | 15 | 5 | 5 | 0 |
| A | 100 |  | 7.5 | 5 | 5 | 5 | 5 | 5 | 5 | 5 | 0 |
| C |  |  | 0 | 0 | 0 | 0 | 0 | 0 | 0 | 0 | 0 |
| P |  |  | 2.5 | 5 | 5 | 5 | 5 | 5 | 0 | 0 | 5 |
| V |  |  | 10 | 4 | 4 | 4 | 4 | 4 | 5 | 0 | 5 |
| I |  |  | 5 | 4 | 4 | 4 | 4 | 4 | 5 | 0 | 5 |
| L |  |  | 5 | 4 | 4 | 4 | 4 | 4 | 15 | 0 | 5 |
| M |  |  | 0 | 0 | 0 | 0 | 0 | 0 | 10 | 0 | 0 |
| F |  |  | 5 | 5 | 5 | 5 | 5 | 5 | 50 | 0 | 5 |
| Y |  |  | 5 | 10 | 10 | 10 | 17.5 | 17.5 | 5 | 0 | 70 |
| W |  |  | 0 | 2 | 2 | 2 | 2 | 2 | 0 | 0 | 0 |
| sum | 100 | 100 | 100 | 100 | 100 | 100 | 100 | 100 | 100 | 100 | 100 |
| # of aa | 1 | 1 | 15 | 17 | 17 | 17 | 17 | 17 | 8 | 3 | 7 |

TABLE 9

| L = 10aa pos | 93 | 94 | mix H1 95 | mix H2 96 | mix H2 97 | mix H2 98 | mix H3 99 | mix H3 100 | mix H3 100a | mix H4 100x | mix H5 101 | mix H6 102 |
|---|---|---|---|---|---|---|---|---|---|---|---|---|
| D |  |  | 5 | 2 | 2 | 2 | 2 | 2 | 2 | 0 | 90 | 0 |
| E |  |  | 5 | 4 | 4 | 4 | 4 | 4 | 4 | 0 | 0 | 0 |
| K |  |  | 0 | 5 | 5 | 5 | 5 | 5 | 5 | 0 | 0 | 0 |
| R |  | 100 | 5 | 10 | 10 | 10 | 5 | 5 | 5 | 0 | 0 | 0 |
| H |  |  | 5 | 4 | 4 | 4 | 4 | 4 | 4 | 0 | 0 | 5 |
| T |  |  | 5 | 4 | 4 | 4 | 4 | 4 | 4 | 0 | 0 | 0 |
| S |  |  | 7.5 | 15 | 15 | 15 | 12.5 | 12.5 | 12.5 | 0 | 0 | 0 |
| N |  |  | 0 | 0 | 0 | 0 | 0 | 0 | 0 | 0 | 0 | 0 |
| Q |  |  | 5 | 2 | 2 | 2 | 2 | 2 | 2 | 0 | 0 | 0 |
| G |  |  | 22.5 | 15 | 15 | 15 | 15 | 15 | 15 | 5 | 5 | 0 |
| A | 100 | 7.5 | 5 | 5 | 5 | 5 | 5 | 5 | 5 | 5 | 5 | 0 |
| C |  |  | 0 | 0 | 0 | 0 | 0 | 0 | 0 | 0 | 0 | 0 |
| P |  |  | 2.5 | 5 | 5 | 5 | 5 | 5 | 5 | 0 | 0 | 5 |
| V |  |  | 10 | 4 | 4 | 4 | 4 | 4 | 4 | 5 | 0 | 5 |
| I |  |  | 5 | 4 | 4 | 4 | 4 | 4 | 4 | 5 | 0 | 5 |
| L |  |  | 5 | 4 | 4 | 4 | 4 | 4 | 4 | 15 | 0 | 5 |
| M |  |  | 0 | 0 | 0 | 0 | 0 | 0 | 0 | 10 | 0 | 0 |
| F |  |  | 5 | 5 | 5 | 5 | 5 | 5 | 5 | 50 | 0 | 5 |

TABLE 9-continued

| L = 10aa pos | 93 | 94 | mix H1 95 | mix H2 96 | mix H2 97 | mix H2 98 | mix H3 99 | mix H3 100 | mix H3 100a | mix H4 100x | mix H5 101 | mix H6 102 |
|---|---|---|---|---|---|---|---|---|---|---|---|---|
| Y |   |   | 5 | 10 | 10 | 10 | 17.5 | 17.5 | 17.5 | 5 | 0 | 70 |
| W |   |   | 0 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 8 | 3 | 7 |

TABLE 10

| L = 11aa pos | 93 | 94 | mix H1 95 | mix H2 96 | mix H2 97 | mix H2 98 | mix H3 99 | mix H3 100 | mix H3 100a | mix H3 100b | mix H4 100x | mix H5 101 | mix H6 102 |
|---|---|---|---|---|---|---|---|---|---|---|---|---|---|
| D |   |   | 5 | 2 | 2 | 2 | 2 | 2 | 2 | 2 | 0 | 90 | 0 |
| E |   |   | 5 | 4 | 4 | 4 | 4 | 4 | 4 | 4 | 0 | 0 | 0 |
| K |   |   | 0 | 5 | 5 | 5 | 5 | 5 | 5 | 5 | 0 | 0 | 0 |
| R |   | 100 | 5 | 10 | 10 | 10 | 5 | 5 | 5 | 5 | 0 | 0 | 0 |
| H |   |   | 5 | 4 | 4 | 4 | 4 | 4 | 4 | 4 | 0 | 0 | 5 |
| T |   |   | 5 | 4 | 4 | 4 | 4 | 4 | 4 | 4 | 0 | 0 | 0 |
| S |   |   | 7.5 | 15 | 15 | 15 | 12.5 | 12.5 | 12.5 | 12.5 | 0 | 0 | 0 |
| N |   |   | 0 | 0 | 0 | 0 | 0 | 0 | 0 | 0 | 0 | 0 | 0 |
| Q |   |   | 5 | 2 | 2 | 2 | 2 | 2 | 2 | 2 | 0 | 0 | 0 |
| G |   |   | 22.5 | 15 | 15 | 15 | 15 | 15 | 15 | 15 | 5 | 5 | 0 |
| A | 100 | 7.5 | 5 | 5 | 5 | 5 | 5 | 5 | 5 | 5 | 5 | 0 |   |
| C |   |   | 0 | 0 | 0 | 0 | 0 | 0 | 0 | 0 | 0 | 0 | 0 |
| P |   |   | 2.5 | 5 | 5 | 5 | 5 | 5 | 5 | 5 | 0 | 0 | 5 |
| V |   |   | 10 | 4 | 4 | 4 | 4 | 4 | 4 | 4 | 5 | 0 | 5 |
| I |   |   | 5 | 4 | 4 | 4 | 4 | 4 | 4 | 4 | 5 | 0 | 5 |
| L |   |   | 5 | 4 | 4 | 4 | 4 | 4 | 4 | 4 | 15 | 0 | 5 |
| M |   |   | 0 | 0 | 0 | 0 | 0 | 0 | 0 | 0 | 10 | 0 | 0 |
| F |   |   | 5 | 5 | 5 | 5 | 5 | 5 | 5 | 5 | 50 | 0 | 5 |
| Y |   |   | 5 | 10 | 10 | 10 | 17.5 | 17.5 | 17.5 | 17.5 | 5 | 0 | 70 |
| W |   |   | 0 | 2 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 17 | 8 | 3 | 7 |

TABLE 11

| L = 12aa pos | 93 | 94 | mix H1 95 | mix H2 96 | mix H2 97 | mix H2 98 | mix H3 99 | mix H3 100 | mix H3 100a | mix H3 100b | mix H3 100c | mix H4 100x | mix H5 101 | mix H6 102 |
|---|---|---|---|---|---|---|---|---|---|---|---|---|---|---|
| D |   |   | 5 | 2 | 2 | 2 | 2 | 2 | 2 | 2 | 2 | 0 | 90 | 0 |
| E |   |   | 5 | 4 | 4 | 4 | 4 | 4 | 4 | 4 | 4 | 0 | 0 | 0 |
| K |   |   | 0 | 5 | 5 | 5 | 5 | 5 | 5 | 5 | 5 | 0 | 0 | 0 |
| R |   | 100 | 5 | 10 | 10 | 10 | 5 | 5 | 5 | 5 | 5 | 0 | 0 | 0 |
| H |   |   | 5 | 4 | 4 | 4 | 4 | 4 | 4 | 4 | 4 | 0 | 0 | 5 |
| T |   |   | 5 | 4 | 4 | 4 | 4 | 4 | 4 | 4 | 4 | 0 | 0 | 0 |
| S |   |   | 7.5 | 15 | 15 | 15 | 12.5 | 12.5 | 12.5 | 12.5 | 12.5 | 0 | 0 | 0 |
| N |   |   | 0 | 0 | 0 | 0 | 0 | 0 | 0 | 0 | 0 | 0 | 0 | 0 |
| Q |   |   | 5 | 2 | 2 | 2 | 2 | 2 | 2 | 2 | 2 | 0 | 0 | 0 |
| G |   |   | 22.5 | 15 | 15 | 15 | 15 | 15 | 15 | 15 | 15 | 5 | 5 | 0 |
| A | 100 |   | 7.5 | 5 | 5 | 5 | 5 | 5 | 5 | 5 | 5 | 5 | 5 | 0 |
| C |   |   | 0 | 0 | 0 | 0 | 0 | 0 | 0 | 0 | 0 | 0 | 0 | 0 |
| P |   |   | 2.5 | 5 | 5 | 5 | 5 | 5 | 5 | 5 | 5 | 0 | 0 | 5 |
| V |   |   | 10 | 4 | 4 | 4 | 4 | 4 | 4 | 4 | 4 | 5 | 0 | 5 |
| I |   |   | 5 | 4 | 4 | 4 | 4 | 4 | 4 | 4 | 4 | 5 | 0 | 5 |
| L |   |   | 5 | 4 | 4 | 4 | 4 | 4 | 4 | 4 | 4 | 15 | 0 | 5 |
| M |   |   | 0 | 0 | 0 | 0 | 0 | 0 | 0 | 0 | 0 | 10 | 0 | 0 |
| F |   |   | 5 | 5 | 5 | 5 | 5 | 5 | 5 | 5 | 5 | 50 | 0 | 5 |
| Y |   |   | 5 | 10 | 10 | 10 | 17.5 | 17.5 | 17.5 | 17.5 | 17.5 | 5 | 0 | 70 |
| W |   | 0 | 2 | 2 | 2 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 17 | 17 | 8 | 3 | 7 |

TABLE 12

| L = 13aa pos | 93 | 94 | mix H1 95 | mix H2 96 | mix H2 97 | mix H2 98 | mix H3 99 | mix H3 100 | mix H3 100a | mix H3 100b | mix H3 100c | mix H3 100d | mix H4 100x | mix H5 101 | mix H6 102 |
|---|---|---|---|---|---|---|---|---|---|---|---|---|---|---|---|
| D | | | 5 | 2 | 2 | 2 | 2 | 2 | 2 | 2 | 2 | 2 | 0 | 90 | 0 |
| E | | | 5 | 4 | 4 | 4 | 4 | 4 | 4 | 4 | 4 | 4 | 0 | 0 | 0 |
| K | | | 0 | 5 | 5 | 5 | 5 | 5 | 5 | 5 | 5 | 5 | 0 | 0 | 0 |
| R | | 100 | 5 | 10 | 10 | 10 | 5 | 5 | 5 | 5 | 5 | 5 | 0 | 0 | 0 |
| H | | | 5 | 4 | 4 | 4 | 4 | 4 | 4 | 4 | 4 | 4 | 0 | 0 | 5 |
| T | | | 5 | 4 | 4 | 4 | 4 | 4 | 4 | 4 | 4 | 4 | 0 | 0 | 0 |
| S | | | 7.5 | 15 | 15 | 15 | 12.5 | 12.5 | 12.5 | 12.5 | 12.5 | 12.5 | 0 | 0 | 0 |
| N | | | 0 | 0 | 0 | 0 | 0 | 0 | 0 | 0 | 0 | 0 | 0 | 0 | 0 |
| Q | | | 5 | 2 | 2 | 2 | 2 | 2 | 2 | 2 | 2 | 2 | 0 | 0 | 0 |
| G | | | 22.5 | 15 | 15 | 15 | 15 | 15 | 15 | 15 | 15 | 15 | 5 | 5 | 0 |
| A | 100 | | 7.5 | 5 | 5 | 5 | 5 | 5 | 5 | 5 | 5 | 5 | 5 | 5 | 0 |
| C | | | 0 | 0 | 0 | 0 | 0 | 0 | 0 | 0 | 0 | 0 | 0 | 0 | 0 |
| P | | | 2.5 | 5 | 5 | 5 | 5 | 5 | 5 | 5 | 5 | 5 | 0 | 0 | 5 |
| V | | | 10 | 4 | 4 | 4 | 4 | 4 | 4 | 4 | 4 | 4 | 5 | 0 | 5 |
| I | | | 5 | 4 | 4 | 4 | 4 | 4 | 4 | 4 | 4 | 4 | 5 | 0 | 5 |
| L | | | 5 | 4 | 4 | 4 | 4 | 4 | 4 | 4 | 4 | 4 | 15 | 0 | 5 |
| M | | | 0 | 0 | 0 | 0 | 0 | 0 | 0 | 0 | 0 | 0 | 10 | 0 | 0 |
| F | | | 5 | 5 | 5 | 5 | 5 | 5 | 5 | 5 | 5 | 5 | 50 | 0 | 5 |
| Y | | | 5 | 10 | 10 | 10 | 17.5 | 17.5 | 17.5 | 17.5 | 17.5 | 17.5 | 5 | 0 | 70 |
| W | | | 0 | 2 | 2 | 2 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 17 | 17 | 17 | 8 | 3 | 7 |

TABLE 13

| L = 14aa pos | 93 | 94 | mix H1 95 | mix H2 96 | mix H2 97 | mix H2 98 | mix H3 99 | mix H3 100 | mix H3 100a | mix H3 100b | mix H3 100c | mix H3 100d | mix H3 100e | mix H4 100x | mix H5 101 | mix H6 |
|---|---|---|---|---|---|---|---|---|---|---|---|---|---|---|---|---|
| D | | | 5 | 2 | 2 | 2 | 2 | 2 | 2 | 2 | 2 | 2 | 2 | 0 | 90 | 0 |
| E | | | 5 | 4 | 4 | 4 | 4 | 4 | 4 | 4 | 4 | 4 | 4 | 0 | 0 | 0 |
| K | | | 0 | 5 | 5 | 5 | 5 | 5 | 5 | 5 | 5 | 5 | 5 | 0 | 0 | 0 |
| R | | 100 | 5 | 10 | 10 | 10 | 5 | 5 | 5 | 5 | 5 | 5 | 5 | 0 | 0 | 0 |
| H | | | 5 | 4 | 4 | 4 | 4 | 4 | 4 | 4 | 4 | 4 | 4 | 0 | 0 | 5 |
| T | | | 5 | 4 | 4 | 4 | 4 | 4 | 4 | 4 | 4 | 4 | 4 | 0 | 0 | 0 |
| S | | | 7.5 | 15 | 15 | 15 | 12.5 | 12.5 | 12.5 | 12.5 | 12.5 | 12.5 | 12.5 | 0 | 0 | 0 |
| N | | | 0 | 0 | 0 | 0 | 0 | 0 | 0 | 0 | 0 | 0 | 0 | 0 | 0 | 0 |
| Q | | | 5 | 2 | 2 | 2 | 2 | 2 | 2 | 2 | 2 | 2 | 2 | 0 | 0 | 0 |
| G | | | 22.5 | 15 | 15 | 15 | 15 | 15 | 15 | 15 | 15 | 15 | 15 | 5 | 5 | 0 |
| A | 100 | | 7.5 | 5 | 5 | 5 | 5 | 5 | 5 | 5 | 5 | 5 | 5 | 5 | 5 | 0 |
| C | | | 0 | 0 | 0 | 0 | 0 | 0 | 0 | 0 | 0 | 0 | 0 | 0 | 0 | 0 |
| P | | | 2.5 | 5 | 5 | 5 | 5 | 5 | 5 | 5 | 5 | 5 | 5 | 0 | 0 | 5 |
| V | | | 10 | 4 | 4 | 4 | 4 | 4 | 4 | 4 | 4 | 4 | 4 | 5 | 0 | 5 |
| I | | | 5 | 4 | 4 | 4 | 4 | 4 | 4 | 4 | 4 | 4 | 4 | 5 | 0 | 5 |
| L | | | 5 | 4 | 4 | 4 | 4 | 4 | 4 | 4 | 4 | 4 | 4 | 15 | 0 | 5 |
| M | | | 0 | 0 | 0 | 0 | 0 | 0 | 0 | 0 | 0 | 0 | 0 | 10 | 0 | 0 |
| F | | | 5 | 5 | 5 | 5 | 5 | 5 | 5 | 5 | 5 | 5 | 5 | 50 | 0 | 5 |
| Y | | | 5 | 10 | 10 | 10 | 17.5 | 17.5 | 17.5 | 17.5 | 17.5 | 17.5 | 17.5 | 5 | 0 | 70 |
| W | | | 0 | 2 | 2 | 2 | 2 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 17 | 17 | 17 | 17 | 8 | 3 | 7 |

TABLE 14

| L = 15aa pos | 93 | 94 | mix H1 95 | mix H2 96 | mix H2 97 | mix H2 98 | mix H3 99 | mix H3 100 | mix H3 100a | mix H3 100b | mix H3 100c | mix H3 100d | mix H3 100e | mix H3 100f | mix H4 100x | mix H5 101 | mix H6 102 |
|---|---|---|---|---|---|---|---|---|---|---|---|---|---|---|---|---|---|
| D | | | 5 | 2 | 2 | 2 | 2 | 2 | 2 | 2 | 2 | 2 | 2 | 2 | 0 | 90 | 0 |
| E | | | 5 | 4 | 4 | 4 | 4 | 4 | 4 | 4 | 4 | 4 | 4 | 4 | 0 | 0 | 0 |
| K | | | 0 | 5 | 5 | 5 | 5 | 5 | 5 | 5 | 5 | 5 | 5 | 5 | 0 | 0 | 0 |
| R | | 100 | 5 | 10 | 10 | 10 | 5 | 5 | 5 | 5 | 5 | 5 | 5 | 5 | 0 | 0 | 0 |
| H | | | 5 | 4 | 4 | 4 | 4 | 4 | 4 | 4 | 4 | 4 | 4 | 4 | 0 | 0 | 5 |
| T | | | 5 | 4 | 4 | 4 | 4 | 4 | 4 | 4 | 4 | 4 | 4 | 4 | 0 | 0 | 0 |
| S | | | 7.5 | 15 | 15 | 15 | 12.5 | 12.5 | 12.5 | 12.5 | 12.5 | 12.5 | 12.5 | 12.5 | 0 | 0 | 0 |

TABLE 14-continued

| L = 15aa pos | 93 | 94 | mix H1 95 | mix H2 96 | mix H2 97 | mix H2 98 | mix H3 99 | mix H3 100 | mix H3 100a | mix H3 100b | mix H3 100c | mix H3 100d | mix H3 100e | mix H3 100f | mix H4 100x | mix H5 101 | mix H6 102 |
|---|---|---|---|---|---|---|---|---|---|---|---|---|---|---|---|---|---|
| N |   |   | 0 | 0 | 0 | 0 | 0 | 0 | 0 | 0 | 0 | 0 | 0 | 0 | 0 | 0 | 0 |
| Q |   |   | 5 | 2 | 2 | 2 | 2 | 2 | 2 | 2 | 2 | 2 | 2 | 2 | 0 | 0 | 0 |
| G |   |   | 22.5 | 15 | 15 | 15 | 15 | 15 | 15 | 15 | 15 | 15 | 15 | 15 | 5 | 5 | 0 |
| A | 100 |   | 7.5 | 5 | 5 | 5 | 5 | 5 | 5 | 5 | 5 | 5 | 5 | 5 | 5 | 5 | 0 |
| C |   |   | 0 | 0 | 0 | 0 | 0 | 0 | 0 | 0 | 0 | 0 | 0 | 0 | 0 | 0 | 0 |
| P |   |   | 2.5 | 5 | 5 | 5 | 5 | 5 | 5 | 5 | 5 | 5 | 5 | 5 | 0 | 0 | 5 |
| V |   |   | 10 | 4 | 4 | 4 | 4 | 4 | 4 | 4 | 4 | 4 | 4 | 4 | 5 | 0 | 5 |
| I |   |   | 5 | 4 | 4 | 4 | 4 | 4 | 4 | 4 | 4 | 4 | 4 | 4 | 5 | 0 | 5 |
| L |   |   | 5 | 4 | 4 | 4 | 4 | 4 | 4 | 4 | 4 | 4 | 4 | 4 | 15 | 0 | 5 |
| M |   |   | 0 | 0 | 0 | 0 | 0 | 0 | 0 | 0 | 0 | 0 | 0 | 0 | 10 | 0 | 0 |
| F |   |   | 5 | 5 | 5 | 5 | 5 | 5 | 5 | 5 | 5 | 5 | 5 | 5 | 50 | 0 | 5 |
| Y |   |   | 5 | 10 | 10 | 10 | 17.5 | 17.5 | 17.5 | 17.5 | 17.5 | 17.5 | 17.5 | 17.5 | 5 | 0 | 70 |
| W |   |   | 0 | 2 | 2 | 2 | 2 | 2 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 17 | 17 | 17 | 17 | 17 | 8 | 3 | 7 |

TABLE 15

| L = 16aa pos | 93 | 94 | mix H1 95 | mix H2 96 | mix H2 97 | mix H2 98 | mix H3 99 | mix H3 100 | mix H3 100a | mix H3 100b | mix H3 100c | mix H3 100d | mix H3 100e | mix H3 100f | mix H3 100f | mix H4 100x | mix H5 101 | mix H6 102 |
|---|---|---|---|---|---|---|---|---|---|---|---|---|---|---|---|---|---|---|
| D |   |   | 5 | 2 | 2 | 2 | 2 | 2 | 2 | 2 | 2 | 2 | 2 | 2 | 2 | 0 | 90 | 0 |
| E |   |   | 5 | 4 | 4 | 4 | 4 | 4 | 4 | 4 | 4 | 4 | 4 | 4 | 4 | 0 | 0 | 0 |
| K |   |   | 0 | 5 | 5 | 5 | 5 | 5 | 5 | 5 | 5 | 5 | 5 | 5 | 5 | 0 | 0 | 0 |
| R | 100 |   | 5 | 10 | 10 | 10 | 5 | 5 | 5 | 5 | 5 | 5 | 5 | 5 | 5 | 0 | 0 | 0 |
| H |   |   | 5 | 4 | 4 | 4 | 4 | 4 | 4 | 4 | 4 | 4 | 4 | 4 | 4 | 0 | 0 | 5 |
| T |   |   | 5 | 4 | 4 | 4 | 4 | 4 | 4 | 4 | 4 | 4 | 4 | 4 | 4 | 0 | 0 | 0 |
| S |   |   | 7.5 | 15 | 15 | 15 | 12.5 | 12.5 | 12.5 | 12.5 | 12.5 | 12.5 | 12.5 | 12.5 | 12.5 | 0 | 0 | 0 |
| N |   |   | 0 | 0 | 0 | 0 | 0 | 0 | 0 | 0 | 0 | 0 | 0 | 0 | 0 | 0 | 0 | 0 |
| Q |   |   | 5 | 2 | 2 | 2 | 2 | 2 | 2 | 2 | 2 | 2 | 2 | 2 | 2 | 0 | 0 | 0 |
| G |   |   | 22.5 | 15 | 15 | 15 | 15 | 15 | 15 | 15 | 15 | 15 | 15 | 15 | 15 | 5 | 5 | 0 |
| A | 100 |   | 7.5 | 5 | 5 | 5 | 5 | 5 | 5 | 5 | 5 | 5 | 5 | 5 | 5 | 5 | 5 | 0 |
| C |   |   | 0 | 0 | 0 | 0 | 0 | 0 | 0 | 0 | 0 | 0 | 0 | 0 | 0 | 0 | 0 | 0 |
| P |   |   | 2.5 | 5 | 5 | 5 | 5 | 5 | 5 | 5 | 5 | 5 | 5 | 5 | 5 | 0 | 0 | 5 |
| V |   |   | 10 | 4 | 4 | 4 | 4 | 4 | 4 | 4 | 4 | 4 | 4 | 4 | 4 | 5 | 0 | 5 |
| I |   |   | 5 | 4 | 4 | 4 | 4 | 4 | 4 | 4 | 4 | 4 | 4 | 4 | 4 | 5 | 0 | 5 |
| L |   |   | 5 | 4 | 4 | 4 | 4 | 4 | 4 | 4 | 4 | 4 | 4 | 4 | 4 | 15 | 0 | 5 |
| M |   |   | 0 | 0 | 0 | 0 | 0 | 0 | 0 | 0 | 0 | 0 | 0 | 0 | 0 | 10 | 0 | 0 |
| F |   |   | 5 | 5 | 5 | 5 | 5 | 5 | 5 | 5 | 5 | 5 | 5 | 5 | 5 | 50 | 0 | 5 |
| Y |   |   | 5 | 10 | 10 | 10 | 17.5 | 17.5 | 17.5 | 17.5 | 17.5 | 17.5 | 17.5 | 17.5 | 17.5 | 5 | 0 | 70 |
| W |   |   | 0 | 2 | 2 | 2 | 2 | 2 | 2 | 2 | 2 | 2 | 2 | 2 | 2 | 0 | 0 | 0 |
| sum | 100 | 100 | 100 | 100 | 100 | 100 | 100 | 100 | 100 | 100 | 100 | 100 | 100 | 100 | 100 | 100 | 100 | 100 |
| # of aa | 1 | 1 | 15 | 17 | 17 | 17 | 17 | 17 | 17 | 17 | 17 | 17 | 17 | 17 | 17 | 8 | 3 | 7 |

Example 1.3: Design of L-CDR3

The analysis of the L-CDR3 was done for all re-arranged sequences irrespective of the VL germline family, since L-CDR3 is partly encoded germline-independent by the J-segment. Based on analysis of canine re-arranged Vkappa-sequences, it was found, that a Kabat L-CDR3-length of 9 amino acids occurs in about 85% of all Vkappa sequences. Thus, the length of the Kabat L-CDR3 for the Vkappa regions in the library was set to a length of 9 amino acids (see Table 16). For Vlambda-sequences the most frequent Kabat L-CDR3 length is 11 aa (60%) followed by 10 aa (30%). Thus the lengths of the Kabat L-CDR3 for the Vlambda regions in the library was set to the lengths of 10 and 11 amino acids (see Table 17 and Table 18). The observed amino acid distribution was slightly modified to finalize the design of the L-CDR3 in the library, e.g. by complete avoidance of cysteines and avoidance of glycosylation-sites (NxS, NxT).

TABLE 16

| L = 9aa pos | mix K9 89 | mix K2 90 | mix K3 91 | mix K4 92 | mix K5 93 | mix K6 94 | mix K7 95 | mix K8 96 | 97 |
|---|---|---|---|---|---|---|---|---|---|
| D | 0 | 0 | 5 | 0 | 0 | 5 | 0 | 0 | 0 |
| E | 0 | 0 | 0 | 5 | 0 | 5 | 0 | 0 | 0 |
| K | 0 | 0 | 0 | 5 | 5 | 0 | 0 | 10 | 0 |
| R | 0 | 0 | 5 | 5 | 5 | 5 | 0 | 10 | 0 |
| H | 2.5 | 5 | 5 | 5 | 5 | 2.5 | 0 | 4 | 0 |
| T | 0 | 0 | 5 | 25 | 5 | 10 | 2 | 0 | 100 |
| S | 0 | 0 | 12.5 | 5 | 15 | 10 | 2 | 4 | 0 |
| N | 0 | 0 | 0 | 0 | 0 | 0 | 0 | 0 | 0 |
| Q | 70 | 95 | 0 | 0 | 30 | 0 | 0 | 4 | 0 |
| G | 27.5 | 0 | 25 | 5 | 5 | 5 | 0 | 4 | 0 |
| A | 0 | 0 | 12.5 | 5 | 5 | 5 | 0 | 0 | 0 |
| C | 0 | 0 | 0 | 0 | 0 | 0 | 0 | 0 | 0 |
| P | 0 | 0 | 0 | 0 | 0 | 5 | 94 | 20 | 0 |
| V | 0 | 0 | 5 | 5 | 0 | 5 | 0 | 5 | 0 |
| I | 0 | 0 | 5 | 10 | 5 | 5 | 0 | 5 | 0 |
| L | 0 | 0 | 5 | 10 | 5 | 5 | 2 | 5 | 0 |
| M | 0 | 0 | 0 | 0 | 0 | 0 | 0 | 0 | 0 |
| F | 0 | 0 | 5 | 5 | 5 | 20 | 0 | 10 | 0 |

TABLE 16-continued

| L = 9aa pos | mix K9 89 | mix K2 90 | mix K3 91 | mix K4 92 | mix K5 93 | mix K6 94 | mix K7 95 | mix K8 96 | 97 |
|---|---|---|---|---|---|---|---|---|---|
| Y | 0 | 0 | 5 | 5 | 5 | 10 | 0 | 15 | 0 |
| W | 0 | 0 | 5 | 5 | 5 | 2.5 | 0 | 10 | 0 |
| sum | 100 | 100 | 100 | 100 | 100 | 100 | 100 | 100 | 100 |
| # of aa | 3 | 2 | 13 | 14 | 14 | 15 | 4 | 13 | 1 |

TABLE 17

| L = 10aa pos | mix L1 89 | mix L2 90 | mix L3 91 | mix L4 92 | mix L5 93 | mix L6 94 | mix L7 95 | mix L8 95a | mix L9 96 | 97 |
|---|---|---|---|---|---|---|---|---|---|---|
| D | 0 | 0 | 0 | 60 | 5 | 5 | 0 | 5 | 0 | 0 |
| E | 0 | 0 | 0 | 0 | 0 | 0 | 0 | 0 | 0 | 0 |
| K | 0 | 0 | 0 | 0 | 0 | 5 | 5 | 10 | 0 | 0 |
| R | 0 | 0 | 2.5 | 0 | 10 | 10 | 5 | 10 | 2.5 | 0 |
| H | 0 | 0 | 5 | 2.5 | 2.5 | 2.5 | 5 | 5 | 5 | 0 |
| T | 0 | 15 | 2.5 | 7.5 | 15 | 20 | 7.5 | 12.5 | 12.5 | 0 |
| S | 55 | 50 | 0 | 0 | 25 | 30 | 12.5 | 20 | 5 | 0 |
| N | 0 | 0 | 0 | 0 | 0 | 0 | 0 | 0 | 0 | 0 |
| Q | 30 | 0 | 0 | 0 | 0 | 0 | 0 | 0 | 0 | 0 |
| G | 5 | 0 | 0 | 5 | 10 | 15 | 10 | 10 | 10 | 0 |
| A | 10 | 25 | 2.5 | 15 | 5 |  | 5 | 5 | 10 | 0 |
| C | 0 | 0 | 0 | 0 | 0 | 0 | 0 | 0 | 0 | 0 |
| P | 0 | 0 | 0 | 0 | 5 | 5 | 5 | 5 | 15 | 0 |
| V | 0 | 5 | 0 | 5 | 0 | 0 | 5 | 0 | 10 | 100 |
| I | 0 | 0 | 0 | 0 | 5 | 5 | 0 | 5 | 5 | 0 |
| L | 0 | 5 | 0 | 0 | 5 | 2.5 | 30 | 2.5 | 2.5 | 0 |
| M | 0 | 0 | 0 | 0 | 0 | 0 | 0 | 0 | 0 | 0 |
| F | 0 | 0 | 10 | 0 | 5 | 0 | 5 | 5 | 7.5 | 0 |
| Y | 0 | 0 | 30 | 5 | 5 | 0 | 5 | 5 | 10 | 0 |
| W | 0 | 0 | 47.5 | 0 | 2.5 | 0 | 0 | 0 | 5 | 0 |
| sum | 100 | 100 | 100 | 100 | 100 | 100 | 100 | 100 | 100 | 100 |
| # of aa | 4 | 5 | 7 | 7 | 13 | 10 | 12 | 13 | 13 | 1 |

TABLE 18

| L =11aa pos | mix L1 89 | mix L2 90 | mix L3 91 | mix L4 92 | mix L5 93 | mix L6 94 | mix L7 95 | mix L8 95a | mix L10 95b | mix L9 96 | 97 |
|---|---|---|---|---|---|---|---|---|---|---|---|
| D | 0 | 0 | 0 | 60 | 5 | 5 | 0 | 5 | 0 | 0 | 0 |
| E | 0 | 0 | 0 | 0 | 0 | 0 | 0 | 0 | 0 | 0 | 0 |
| K | 0 | 0 | 0 | 0 | 0 | 5 | 5 | 10 | 0 | 0 | 0 |
| R | 0 | 0 | 2.5 | 0 | 10 | 10 | 5 | 10 | 5 | 2.5 | 0 |
| H | 0 | 0 | 5 | 2.5 | 2.5 | 2.5 | 5 | 5 | 5 | 5 | 0 |
| T | 0 | 15 | 2.5 | 7.5 | 15 | 20 | 7.5 | 12.5 | 15 | 12.5 | 0 |
| S | 55 | 50 | 0 | 0 | 25 | 30 | 12.5 | 20 | 10 | 5 | 0 |
| N | 0 | 0 | 0 | 0 | 0 | 0 | 0 | 0 | 0 | 0 | 0 |
| Q | 30 | 0 | 0 | 0 | 0 | 0 | 0 | 0 | 0 | 0 | 0 |
| G | 5 | 0 | 0 | 5 | 10 | 15 | 10 | 10 | 25 | 10 | 0 |
| A | 10 | 25 | 2.5 | 15 | 5 |  | 5 | 5 | 15 | 10 | 0 |
| C | 0 | 0 | 0 | 0 | 0 | 0 | 0 | 0 | 0 | 0 | 0 |
| P | 0 | 0 | 0 | 0 | 5 | 5 | 5 | 5 | 0 | 15 | 0 |
| V | 0 | 5 | 0 | 5 | 0 | 0 | 5 | 0 | 7.5 | 10 | 100 |
| I | 0 | 0 | 0 | 0 | 5 | 5 | 0 | 5 | 5 | 5 | 0 |
| L | 0 | 5 | 0 | 0 | 5 | 2.5 | 30 | 2.5 | 5 | 2.5 | 0 |
| M | 0 | 0 | 0 | 0 | 0 | 0 | 0 | 0 | 0 | 0 | 0 |
| F | 0 | 0 | 10 | 0 | 5 | 0 | 5 | 5 | 2.5 | 7.5 | 0 |
| Y | 0 | 0 | 30 | 5 | 5 | 0 | 5 | 5 | 5 | 10 | 0 |
| W | 0 | 0 | 47.5 | 0 | 2.5 | 0 | 0 | 0 | 0 | 5 | 0 |
| sum | 100 | 100 | 100 | 100 | 100 | 100 | 100 | 100 | 100 | 100 | 100 |
| # of aa | 4 | 5 | 7 | 7 | 13 | 10 | 12 | 13 | 11 | 13 | 1 |

Example 1.4: Diversification of the Canine Library

The canine antibody library generated in the present study comprises diversified L-CDR3 and H-CDR3 regions. CDR3 library cassettes were generated by Slonomics technology which allows controlled incorporation of only desirable codons in the CDR3-cassettes preventing introduction of cysteine- and stop-codons (Van den Brulle et al. Biotechniques. 2008 September; 45(3):340-3). Sequencing of unselected clones after library generation indicated that overall incidence of undesirable DNA mutations, deletions, insertions and frameshifts of the L-CDR3 and H-CDR3 cassettes was low.

We reasoned that biochemical and biophysical properties of the VH and VL-domains depend also on their H-CDR3 and L-CDR3 sequence, respectively and therefore we decided to introduce one particular H-CDR3, kappa L-CDR3 and lambda L-CDR3 sequence into the selected canine VH, Vkappa and Vlambda genes, respectively for the purpose of the VH/VL comparison. The H-CDR3 (WGGDGFYAMDY) (SEQ ID NO:43) and kappa L-CDR3 sequence (QQHYTTPPT) (SEQ ID NO:44) were derived from antibody hu4D5-8 (Carter et al. Proc Natl Acad Sci USA 1992; 89:4285-9;) and a lambda-like L-CDR-3 (QSYDSSLSGVV) (SEQ ID NO:45) has been used which all had been applied previously for the assessment of human master-genes (Knappik et al., 2000, J Mol Biol 296, 57-86, Ewert et al., J Mol Biol 2003; 325:531-53).

Example 1.5 Display and Expression Vectors

The pMORPH18 (Rauchenberger et al. J Biol Chem. 2003 Oct. 3; 278 (40):38194-205) and pMORPHx30 (Prassler et al. J Mol Biol. 2011 Oct. 14; 413(1):261-78) vectors were used as templates for the generation of the new Fab Display pCaDis18 and the Fab expression vector pCaBx, respectively, with the following modifications. For both vectors, the ompA leader sequences upstream of the Ig light chain encoding sequences were modified at their C-termini to introduce the restriction sites Ndel, respectively, to assure authentic N-termini of the VL and VH protein sequences and to allow convenient sub-cloning of Fab fragments into pCaMx IgG vectors. In addition a mammalian IgG expression vector set was constructed. Canine IgG CH1 and Clambda & Ckappa sequences were synthesized by GeneArt (*H. sapiens* codon optimization). The CH construct was cloned into a pM4_Vector containing a Kan stuffer (pCaMx_Stuffer). The two codon optimized Clambda & Ckappa sequences were cloned into a generic Geneart vector. (pMA-T_CaMin kappa pMA-T_CaMin lambda). IgG conversion was performed using state of the art molecular biology methods.

Example 2. Biophysical Characterization of Canine VHNL Pairs

The following examples describe methods and results of the biophysical characterization of canine VH/VL pairs.

Example 2.1 Phage Preparation

The antibody combinations synthesized in Example 1.1, were cloned into the Fab display vector pCaDis for functional testing. Vectors contained combinations of 5 VH and 6 VL master genes, which yield 30 possible combinations. A masterplate was generated by filling each of the wells with 2×YT/Cam/1% Glucose medium and inoculating them with single clones from the 30 generated antibody constructs. The plate was incubated overnight at 37° C. while shaking. Next day, the masterplate was stored in a final concentration of 15% glycerol and frozen at −80° C. For phage preparations, 2×YT/Cam/1% Glucose was inoculated with glycerostocks derived from masterplates and incubated while shaking at 400 rpm until an OD600 nm of 0.5 was reached. The cells were then infected with VCSM 13 helper phage and incubated at 37° x for 30 min without shaking and then for another 30 min while shaking at 400 rpm. Bacteria were centrifuged and re-suspended in 2×YT medium with 34 µg/ml chloramphenicol, 50 µg/ml kanamycin and 0.25 mM isopropyl-β-D-thiogalactopyranoside (2×YT/Cam/Kan/IPTG) and further incubated at 22° C. for 18-20 h for phage production. Supernatants containing the Fab-presenting phages were transferred to new tubes and phages were precipitated using ⅕ of the supernatant volume of PEG/NaCl (20% PEG 6000, 2.5 M NaCl in ddH2O). After centrifugation and removal of supernatants, phage pellets were resuspended in sterile PBS. Phage titers were determined by absorbance measurement at OD268 nm (Nanodrop, peqlab) and confirmed by limiting dilution plating of infected *E. coli* TG1F+ cells on LB/Cam/Gluc plates.

Example 2.2 Fab Phage Display Rates by Western Blot

Phage supernatants prepared as in Example 2.1 were used for determination of Fab display rates on phage particles using Western blotting techniques.

Around 1E+09 phages in a total volume of 10 µl were mixed with 4×LDS loading dye and heated for 10 min at 80° C. A gel (NUPAGE 4-12% Bis-Tris-Gel, 1.0 mm×12 well, Novex, Cat. NP0322Box) was placed into a running chamber and the chamber filled with 1×MES running buffer (prepared from NUPAGE MES SDS Running Buffer, 20×, Invitrogen). Samples and marker were loaded onto the gel and electrophoresis was performed for 35 min at 200 V. The gel was removed, washed with ddH20 and transfer of proteins to Western Blot membrane was carried out with an iBlot aperture. Subsequently, the membrane was blocked with 10% milk powder in TBS-T at RT for 1.5 h. The membrane was washed quickly with TBS-T and incubated with an anti-pIII antibody (mouse anti-pIII, MoBiTec, Cat.: PSKAN3; 1:1000 in TBS-T 3% MP) for 1 h at RT. After 3×5 min washing steps, the membrane was incubated with anti-mouse IgG-HRP (Anti-mouse IgG-HRP (P9), Jackson Immuno Research, Code 115-036-062; 1:10'000 in TBS-T, 3% MP) for 1 h at RT. Membrane was washed 3×5 min with TBS-T and chemiluminescence was recorded with the Biorad Imager (Program: "blot colorimetric" to show the protein marker and "blot chem" to show the HRP detection) after addition of HRP-substrate (Immobilon Western Chemiluminescent HRP Substrate, Millipore, Cat. WBKLS0500). On the anti-pIII western blot, relative amounts of pIII(fl) and pIII(ct)-Fd were determined. Results are shown in FIG. 4.

Efficient display of library members on phage particles is a prerequisite for successful phage display selections. We used Western-Blot for determination of display efficiency of the canine VH/VL combinations in Fab-format. Our data indicate that essentially all tested canine VH/VL combinations were displayed on phages. Results are shown in FIG. 5.

Example 2.3 Relative Fab Expression ELISA

Clones of the 30 VH/VL combinations cloned into pCaBx were inoculated in growth medium (2×YT/Cam/IPTG/0.1% glucose) and incubated at 37° C. shaking at 400 rpm for ~3 h until cultures became slightly turbid. Subsequently, cultures were incubated overnight at 22° C. shaking before cells were lysed using BEL buffer (24.7 mg/ml boric acid, 18.7 mg/ml NaCl, 1.48 mg/ml EDTA, 2.5 mg/ml lysozyme, adjusted to pH 8.0 with 10 M NaOH) and blocked with 10% milk powder in PBS. Fab expression was determined by ELISA using an anti-canine F(ab')2 fragment specific capture antibody (rabbit anti-dog IgG Fab'2 antibody unconjugated; LifeSpan BioSciences, LS-C69729) and an AP-conjugated anti-dog IgG F(ab')2 fragment detection antibody (Goat Anti-Dog IgG (H+L)-Alkaline Phosphatase antibody, Sigma SAB3700097) with AttoPhos (Roche). Relative Fab expression levels were calculated by dividing the signal of a respective Fab VH/VL pair through the signal of the reference human/canine chimeric antibody. More than 85% of the tested Fab VH/VL pairs showed a relative expression of at least 0.5 of the controls. Lambda clones had, on average, the highest relative Fab expression levels. Results are shown in FIG. 6.

Example 2.4 Exploratory Scale Production of His-Tagged Fab Fragments

Expression of Fab fragments encoded by bacterial expression vector in *E. coli* TG1F− cells was carried out in shake flask cultures using 500 mL of 2×YT medium supplemented with 0.1% glucose and 34 µg/mL chloramphenicol. Cultures were shaken until the OD600 reached a value of 0.5. Fab expression was induced by adding IPTG (isopropyl-ß-D-thiogalactopyranoside) and further cultivation for 20 h. Cells were harvested and disrupted using lysozyme. His6-tagged (SEQ ID NO:47) Fab fragments were isolated via IMAC (Bio-Rad) and eluted using imidazole. Buffer exchange to 1× Dulbecco's PBS (pH 7.2) was performed using 'PD10' columns (GE Healthcare). Samples were sterile filtered (0.2 µm). Protein concentrations were determined by UV-spectrophotometry. The purity of the samples was analyzed in denaturing, non-reducing 15% SDS-PAGE. The % monomer of purified Fab fragments representing each of the 30 canine VHNL pairs were determined by size exclusion chromatography (SEC). SEC was performed on an ÄKTA Purifier system (GE Healthcare Europe GmbH, Freiburg, Germany). For separation a Superdex75 HR 10/30 column was used (GE Healthcare Europe GmbH, Freiburg, Germany). For each sample 10 µl of protein was loaded onto the column, separation was performed at a flow rate of 0.05 ml/min and recorded analyzing the UV absorption at 260 and 280 nm. The running buffer was composed of Gibco D-PBS, pH 7.4 (Invitrogen, Paisley, USA). Results are shown in FIG. 7.

As shown in FIG. 6 and FIG. 7 all tested canine VH/VL combinations, are expressed in *E. coli* and the expression rate of purified Fab ranges from 0.2 mg/L to 8 mg/L bacterial culture (bars, left y-axis). Furthermore, characterization of isolated material revealed that the majority of purified canine Fab VHNL was at monomeric form above 85%. This indicates usefulness for the development of canine antibodies using the library.

Example 2.5 Exploratory Scale Production of IgG and Determination of Monomer Content Eukaryotic HKB11 cells were transfected with pCaMx mammalian expression vector DNA encoding both heavy and light chains of IgG. Cell culture supernatants were harvested on day 3 or 6 post transfection and subjected to standard Protein A affinity chromatography (MabSelect SURE, GE Healthcare). Buffer exchange was performed to 1× Dulbcecco's PBS (pH 7.2) and samples were sterile filtered (0.2 µm pore size).

Protein concentrations were determined by UV-spectrophotometry and purities of IgG were analyzed under denaturing, reducing and non-reducing conditions using CE-SDS (LabChip GXII, Perkin Elmer). The % monomer of purified IgG1 representing each of the 30 canine VHNL pairs were determined by size exclusion chromatography (SEC). HP-SEC was performed on a Dionex UltiMate 3000 Titanium HPLC system (Dionex Corporation, Germering, Germany) in combination with Wyatt miniDAWN Treos and Wyatt Optilab rEX (Wyatt Technology Europe, Dernbach, Germany). For separation a Tosoh TSK-Gel G3000SWxl column was used (Tosoh Bioscience, Stuttgart, Germany). For each sample 15 µg of protein was loaded onto the column, separation was performed at a flow rate of 0.5 ml/min and recorded analyzing the UV absorption at 280 nm. The running buffer was composed of Gibco D-PBS, pH 7.4 (Invitrogen, Paisley, USA). The results are shown in FIG. 8 (dots, right Y-axis). Constructs with sufficient expression rates showed excellent monomer contents >95%. For selection of VH/VL combinations used as scaffold for library cloning and CDR3 diversification, both, Fab as well as IgG production data were taken into consideration.

Example 2.6 Relative Fab Phage Display Rate ELISA

Fab display on M13 phage was determined by ELISA using an anti-M13 antibody (Amersham) to capture the phage via the major coat protein pVIII and using an anti-Fd antibody (The Binding Site) that binds to the displayed Fab. Appropriate dilutions of the phage supernatants and reference samples were detected with an anti-M13 peroxidase conjugate (Amersham) and QuantaBlu™ (Pierce). Calculations of relative display rates for each sample were performed by dividing the anti-Fd titer by the titer of anti-M13. Titers were obtained from calibration curves of reference phage preparations.

Example 2.7 Fab Temperature Stability ELISA

Appropriate dilutions of bacterial lysates are exposed to different temperatures (0° C., 60° C., 70° C. and 80° C.) for 45 min. Intact Fab molecules are detected by ELISA using an anti-6×His (SEQ ID NO:47) capture antibody (R&D Systems) and AP-labeled anti-canine Ig detection antibody with AttoPhos (Roche).

Example 2.8. Purified IgG Thermal Stability Determination

IgG thermal stability is determined by differential scanning fluorometry (DSF). DSF is a fluorescence dye based technique that monitors thermal unfolding (melting point) of a protein of interest. Changes in the fluorescence of a hydrophobic dye interacting with the hydrophobic amino acid side-chains of the unfolding protein are monitored over a temperature ramp. The following materials are used: Sypro Orange fluorescent dye (Sigma, #S5692); iCycler iQ PCR Plates, 96-well (Biorad, #2239441); Microseal B Adhesive Sealer (Biorad #MSB-1001); 96-well Optical Pad (Biorad, #ADR3296); and iCycler iQ5 Thermal cycler (Biorad). Diluted Sypro Orange is added to each well of a 96 well iCycler iQ PCR Plate, and the samples are tested at a final concentration of at least 0.1 mg/ml. The temperature is scanned from 20° C. to 95° C. at a heating rate of 60° C./h, and the temperature of unfolding is calculated by analysis of the midpoint of the fluorescence transition.

Example 2.9. Isoelectric Point (pI) Calculation

The Isoelectric point of each IgG is calculated. Methods of determining the pI of a protein are known to one of skill in the art. For example, the following tools can be used: http with the extension expasy.org/tools/pi_tool.html of the world wide web; Vector NTI (Invitrogen, Carlsbad, Calif.).

Example 3. Antibody Selections and Characterization

In order to confirm the effectiveness of the library design, the library is tested against various antigens. The antibodies selected are then tested in both Fab and IgG formats for developability characteristics, such as: a) Fab display rate; b) Fab expression yield, c) Fab thermal stability; d) Fab serum stability; e) Fab SEC % monomer; f) IgG expression yield; g) IgG thermal stability; h) IgG serum stability; i) IgG SEC % monomer; j) IgG isoelectric point (pI); k) thermal stability in Fab or IgG formats before and after exposure to acid using differential scanning fluorometry; l) Absorption in Fab or IgG formats before and after exposure to acid; m) molecular radius and % polydispersity before and after exposure to acid as measured by dynamic light scattering; and/or n) particle staining in Fab or IgG formats. In addition, the affinity for the antigen in Fab format is determined.

Example 3.1 Phage Preparation

Phage displaying the respective VH/VL pairs in Fab format were prepared as follows. For each library phage preparation 80 ml 2×YT/Cam/Glc medium were inoculated with bacteria from the corresponding library glycerol stock resulting in an OD600 nm of 0.2-0.3. Cultures were shaken for 30-90 min at 120 rpm and 37° C. until an OD600 nm of 0.45-0.55 is reached. Then helper phage was added at a multiplicity of infection of 10 to the bacterial culture followed by an incubation for 45 min at 37° C. without shaking and then for 45 min at 37° C. shaking at 120 rpm. Bacteria were spun down and helper phage containing supernatant was discarded. Phage-infected bacteria were resuspended in 400 ml 2×YT/Cam/Kan/IPTG medium and incubated overnight at 22° C. with shaking at 120 rpm. The next day bacteria from the overnight culture were pelleted and the supernatant containing the Fab-presenting phage was collected. Phage precipitation was performed by adding ⅕ total volume of pre-cooled PEG/NaCl to the phage-containing supernatant. The sample was incubated for at least 30 min on ice until clouds of precipitating phage became visible. Precipitated phages were spun down and were resuspended in 20 ml PBS. The sample was rotated slowly to obtain a homogeneous suspension and residual bacterial debris was pelleted and discarded. From the phage-containing supernatant the phage were precipitated again using PEG/NaCl. Finally, the phage pellet was resuspended in PBS, transferred to a sterile tube and shaken slowly to obtain a homogeneous suspension. Phage titers were determined by spot titration and ELISA. Phage titers and display levels of Fab fragments expressed by the display vector pCaDis (shown in FIG. 9) and presented on the phage were evaluated for each individual phage preparation by ELISA and/or Westernblot (see Example 2.6) For ELISA two different antibodies were used for capturing: (1) anti-M13 antibody (Amersham #27-9420-01) was used, as it captures phage particles via the major coat protein g8p; therefore, phage titer can be determined. (2) anti-canine-Fab'2 (LS Bio, #LS-C69729) was used, which binds to the displayed Fab; therefore, only phage displaying Fabs were captured. For (1) and (2) separate reference curves were used. A monoclonal anti-M13 (directed against major coat protein of M13 phage, g8p) conjugated to HRP was used as a detection antibody. The evaluation of the ELISA data was completed as follows: calibration curves are created and the titers of the phage supernatants and control were calculated. For each sample, the titer on anti-Fd is divided by the titer on anti-M13 (anti-pVIII), the resulting ratio is the relative display rate.

Example 3.2. Antibody Selections

Phage display selection may be done as described below or by another method known to one of skill in the art. For example, parallel panning strategies (e.g., solution panning, Fc capture panning, direct solid phase panning) are performed in order to maximize the chance of identifying diverse binding antibodies with the desired biophysical characteristics. Various soluble proteins can be chosen as model antigens for library validation (e.g. lysozyme). Collection screening against the model antigen is performed in a bead-based solution panning with the antigen covalently coupled to magnetic Dynabeads via amide bond formation to carboxylic acid groups (Dynal/Invitrogen Prod. no. 143.06) as described below. Selection against the model antigen can also be performed with an Fc-capture panning strategy, described below.

Example 3.2.1. Bead-Based Solution Panning

Model antigen and control BSA coated carboxyl-beads (Dynal) are blocked with 5% Milkpowder+0.1% Tween20 in PBS for 2 h at room-temperature (RT) before incubation with pre-adsorbed phages for 2 h at RT. After several washing steps, bound phage are eluted and amplified by infecting TG1F+ cells for the next round of selection. After 3 rounds of selection, pCaDis (shown in FIG. 9) phagemid DNA is isolated and Fab encoding fragments are excised by restriction digestion with XbaI and EcoRI and ligated into the expression vector pCaBx (shown in FIG. 10) and transformed into E. coli TG1F-. The infected cultures are then plated on large LB/Cam/Gluc plates and allowed to grow at 34° C. Single clones are isolated and tested for Fab expression yield and antigen binding by ELISA. Fab expression is detected by incubating Fab containing cell extracts on a rabbit anti-dog IgG F(ab)'2 antibody (LifeSpan BioSciences, LS-C69729) coated ELISA plate followed by detection with goat anti-dog IgG (H+L) Alkaline Phosphatase antibody (Sigma, SAB37000097). Antigen specificity is tested e.g., by screening Fab containing cell extracts on model antigen coupled-Carboxylbeads and BSA coupled-Carboxylbeads (Dynal) with a fluorometric microvolume assay technology (FMAT®) for bead based assays (Applied Biosystems 8200 Cellular Detection System/PE Biosystems). Primary Hits are defined as Fabs that result in an FMAT mean fluorescence signal of at least 5-fold above the background which is set to a value of 200. Specificity to the model antigen is confirmed in a secondary ELISA with the model antigen as cognate antigen and an irrelevant antigen as negative control antigen. About 50-100 clones for each tested sub-library, sub-library-mix or the total library are picked for sequencing Heavy and light chain CDR3 region to estimate the sequence diversity of model antigen binding antibodies. Sequencing results show that the constructed libraries contain a diverse repertoire of model antigen binders. Binding characterization by ELISA shows that isolated antibodies are highly specific to the cognate model antigen of interest with no cross-reactivity to the irrelevant control antigen, proving the usability of the library for biomedical research and generation of highly specific—therapeutic antibodies.

Example 3.2.2. Fc-Capture Panning

Three rounds of solid phase Fc-capture panning are performed using recombinant human Fc-tagged model protein immobilized by capturing with goat anti human-IgG Fc specific (Jackson; Cat. 109-005-098) or mouse anti-human-IgG Fc specifc (Jackson; Cat. 209-005-098) on Maxisorp plates (Nunc). Prior to each selection round, phages are blocked with 0.1 mg/ml human, goat and mouse immunoglobulin in PBS/5% milk, /5% BSA/0.1% Tween for 2 h at RT. After several washing steps, bound phage are eluted and amplified by infecting TGIF+ cells for the next round of selection. After the third selection round, pCaDis (shown in FIG. 9) phagemid DNA is isolated and Fab encoding fragments are exised by restriction digestion with XbaI and EcoRI and ligated into the expression vector pCaBx (shown in FIG. 10) and transformed into TGIF−. The infected cultures are then plated on large LB/Cam/Gluc plates and allowed to grow at 34° C. Single clones are isolated and tested for Fab expression yield and antigen binding by ELISA. Fab expression is detected as described above. Antigen specificity is tested by ELISA screening with Fab containing cell extracts on model protein_Fc antigen captured via goat anti-human IgG antibody (Jackson; Cat. 109-005-098) coated on MaxiSorp plates. Primary Hits are defined as Fabs that result in an ELISA signal of at least 5-fold above the background. Specificity to model protein_Fc is confirmed in a secondary Fc-capture ELISA with model antigen_Fc as cognate antigen and an irrelevant protein_Fc as negative control antigen.

About 50-100 clones are picked for sequencing heavy and light chain CDR3 regions to estimate the sequence diversity of model antigen_Fc binding antibodies. The sequencing results confirm that the constructed libraries contain a diverse repertoire of binders. Binding characterization by ELISA shows that isolated antibodies are highly specific to the cognate model antigen of interest with no cross-reactivity to the irrelevant control antigen, proving the usability of the library for biomedical research and generation of highly specific—therapeutic antibodies.

Example 3.3. Developability Testing

The antibodies or fragments specific for the antigens are tested in both Fab and IgG formats for developability characteristics, such as, thermal stability in Fab format, affinity in Fab format, pI in IgG format, expression yield in IgG format, thermal stability in IgG format, and % monomer in IgG format as determined by SEC by the methods disclosed herein or by other methods known to one of skill in the art. The thermal stability testing in Fab and IgG formats is completed as described in Examples 2.7 and 2.8. The pI determination is completed as described in Example 2.9. The expression yield in IgG format is completed as described in Example 2.5. The % monomer in IgG format as determined by SEC is completed as described in Example 2.5.

Example 3.4. Biacore KD (Affinity) Determination Via Antigen Capture Setup in Fab Format Binding of monomeric Fab fractions (analyzed by analytical SEC; Superdex75, Amersham Pharmacia) to captured antigen is analyzed as follows: On a CM5 chip (Biacore/GE Healthcare) an appropriate anti-antigen tag capture antibody is covalently immobilized using EDC/NHS chemistry. Kinetic measurements are done by capturing the antigen and subsequent injection of six different Fab concentrations (2n serial dilution). After each cycle the sensor chip is regenerated. A blank injection of running buffer is used for double referencing. All sensorgrams are fitted using BIA evaluation software 3.2 (Biacore/GE Healthcare), to determine kon and koff rate constants, which are used to calculate KD.

The affinity might also be determined by solution equilibrium titration as described in Haenel et al (2005) Analytical Biochemistry 339(1): 182-184.

Isolated antibodies show affinity-values ranging from sub-nanomolar to single-digit nanomolar KDs confirming that strong binding antibodies against the model antigen of interest can be easily isolated from the library.

Example 4. Library Redundancy Analysis and QC by NGS

Library quality was assessed by high-throughput amplicon sequencing using the MiSeq instrument (Illumina ~1 million sequences per VL/VH sample) according to the manuals provided by the manufacturer.

Example 4.1. Amplicon Generation

Briefly, VL or VH amplicons of individual samples (e.g.: plasmid DNA derived from the cloned library) were produced by PCR (1 min 98° C., 15 cycles of 98° C. for 15 sec, 60° C. for 15 sec and 72° C. for 15 sec, 72° C. for 5 min, 15 ng template DNA, 0.4 µM of each primer, 200 µM dNTPs and 1 U Phusion polymerase (NEB)) using specific amplicon fusion primers.

Example 4.2. NGS Using with a Modified TruSeg/Nextera XT Protocol

Amplicons containing the universal Nextera adapters were PCR amplified as described above (first step —adapter PCR), agarose gel purified and quantified. In a second PCR step (index PCR) a unique index combination (i5/i7 indices) was added to the 5'- and 3'-end of each sample in parallel (1 min 98° C., 10 cycles of 98° C. for 15 sec, 60° C. for 15 sec and 72° C. for 60 sec, 72° C. for 5 min, 1 ng template, 0.4 µM primer, 200 µM dNTPs and 0.5 U Phusion polymerase).

PCR products were purified using AMPure XP beads (Beckman Coulter) to remove small fragments, normalized using the SequalPrep Normalization Plate Kit (Invitrogen) and equimolar pooled. The pooled DNA was denaturing by 0.2N NaOH and finally diluted to concentration of 8 to 10 µM. A control library (PhiX) was additionally spiked in the sample pool (5-10%) and the pool was loaded on the flow cell for sequencing. The paired end sequencing run was performed according to MiSeq System User Guide and the sequencing manuals for the MiSeq Reagent Kit v3 (600 cycle).

Sequencing results were directly processed, demultiplexed, stiched and fastq files were generated using the provided MiSeq software package (SAV1.8, MiSeq Reporter).

Example 4.3. Sequence Analysis

The quality filtered sequences were further analyzed using a software developed in-house tailored for processing and analysis of large sequencing datasets. Sequences were de-multiplexed and library specific sequence features were evaluated e.g. V-gene type, HCDR3 length and amino acid distribution. In brief, VH and VL distribution, respectively, is as expected and there is a very good correlation between design and obtained amino acids at desired positions (FIGS. 11, 12 and 13).

Example 5. Phage Display Antibody Selection eGFP (enhanced green fluorescent protein) was chosen as a model antigen for library validation. A solid phase panning followed by screening in direct coating ELISA was performed to isolate eGFP-specific binders from the library. Solid phase pannings were performed using eGFP directly immobilized on microtiter plates. Prior to each selection round, phages were blocked with 10% skim milk powder in PBS. Following phage incubation, several washing steps with PBST were performed to remove very weak/non-specific binders. Bound phages were eluted with a low-pH elution buffer and amplified by infecting TG1F+ cells for the next round of selection. After the final selection round, pCaDis phagemid DNA was isolated and Fab encoding fragments were excised by restriction digestions with XbaI and EcoRI and ligated into the expression vector pCaBx (FIG. 10) and transformed into TG1F– E. coli. The infected cultures were then plated on LB/Cam/Gluc plates and allowed to grow overnight. Single clones were isolated and tested for Fab expression yield and antigen binding by ELISA. Fab expression was detected by incubating Fab containing cell extracts on a rabbi-anti-dog-IgG F(ab)2 (LSBio, Cat.: LS-C69729) coated ELISA plate followed by detection with rabbit anti-dog IgG IgG F(ab)2 specific antibody conjugated with Alkaline Phosphatase (AP) (Sigma, SAB37000097). Antigen specificity was tested by ELISA screening with Fab containing cell extracts on eGFP coated on MaxiSorp plates. Primary Hits were defined as Fabs that result in an ELISA signal of at least 5-fold above the background. Specificity to eGFP was confirmed in a secondary ELISA on a negative control antigen (plate coated with milk protein only).

Heavy and light chain CDR3 regions of 29, 8 and 58 clones for the 2A/2D, 3A/3D and 3B/6B sub-libraries, respectively, were sequenced in order to estimate the sequence diversity of eGFP binding antibodies. Screening and sequencing data are summarized in Table 19. FIG. 13 shows an dot blot visualization of the screening results.

TABLE 19

| Subcode | Screened | S/B >3-10 | S/B >10 | Hitrate [%] | Sequenced | Unique |
|---|---|---|---|---|---|---|
| 2A/2D | 364 | 139 | 149 | 79 | 29 | 1 |
| 3A/3D | 364 | 20 | 2 | 6 | 8 | 3 |
| 3B/6B | 364 | 54 | 120 | 48 | 58 | 5 |

2A/2D contains phage from sub-libraries VL/VH (Vs236/Vs624) and VL/VH (Vs236/Vs618)
3A/3D contains phage from sub-libraries VL/VH (Vs365/Vs624) and VL/VH (Vs365/Vs635)
3B/6B contains phage from sub-libraries VL/VH (Vs365/Vs618) and VL/VH (Vs323/Vs635)

Example 6. Fab ELISA

To compare binding of individual clones obtained after panning selections, purified antibodies in Fab format have been titrated and were tested on eGFP coated on Maxisorp plates with a rabbit anti-dog IgG F(ab)2-specific detection antibody conjugated with Alkaline Phosphatase (AP) (Sigma, SAB37000097). An anti-GFP antibody (MOR06391) previously isolated from the HuCAL library has been included as reference. As illustrated in FIG. 15 antibodies directly isolated from the library exhibit diverse binding strengths with 6/9 candidates showing similar or better binding characteristics as the reference antibody.

Example 7. IgG ELISA

Panning against eGFP as model antigen has been performed as described in Example 5. Specific Fab hits obtained after antibody selections were converted into IgG format using state of the art molecular biology methods and IgG protein was produced as described in Example 2.5. IgG reactivity against eGFP was confirmed in a standard solid phase ELISA (FIG. 16). Detection of IgG binding to eGFP coated on Maxisorp plates was performed with a rabbit anti-dog IgG F(ab)2-specific detection antibody conjugated with Alkaline Phosphatase (AP) (Sigma, SAB37000097). An anti-GFP antibody (MOR06391) previously isolated from the HuCAL library has been included as reference.

What is claimed is:

1. A synthetic canine antibody library, wherein said library comprises members of at least two of the following VH1 regions with an identity of at least 90% to a germline VH1 region selected from Vs618 (SEQ ID NO:4), Vs624 (SEQ ID NO:1), Vs628 (SEQ ID NO:5) and Vs635 (SEQ ID NO:2).

2. The library of claim 1, wherein said members further comprise at least one of the following VL regions with an identity of at least 90% to a germline VL region selected from Vs236 (kappa) (SEQ ID NO:12), Vs321 (lambda) (SEQ ID NO:14), Vs323 (lambda) (SEQ ID NO:16), Vs365 (lambda) (SEQ ID NO:13) and Vs843 (lambda) (SEQ ID NO:15).

3. The library of claim 1, wherein post-translational modification (PTM) sites are removed from one or more of the germline VH regions or the germline VL regions.

4. A synthetic canine antibody library, wherein said library comprises one or more of the following VH/VL combinations:

the VH/VL combination of the VH1 region with an identity of at least 90% to a VH1 region of Vs618 (SEQ ID NO:4) and the VL region with an identity of at least 90% to the VL region of Vs236 (kappa) (SEQ ID NO:12);

the VH/VL combination of the VH1 region with an identity of at least 90% to the VH1 region of Vs635-PTM-low (SEQ ID NO:7) and the VL region with an identity of at least 90% to the VL region of Vs323-PTM-low (lambda) (SEQ ID NO:18);

the VH/VL combination of the VH1 region with an identity of at least 90% to the VH1 region of Vs618 (SEQ ID NO:4) and the VL region with an identity of at least 90% to the VL region of Vs365 (lambda) (SEQ ID NO:13);

the VH/VL combination of the VH1 region with an identity of at least 90% to the VH1 region of Vs624-PTM-low (SEQ ID NO:6) and the VL region with an identity of at least 90% to the VL region of Vs365 (lambda) (SEQ ID NO:13);

the VH/VL combination of the VH1 region with an identity of at least 90% to the VH1 region of Vs635-PTM-low (SEQ ID NO:7) and the VL region with an identity of at least 90% to the VL region of Vs365 (lambda) (SEQ ID NO:13);

the VH/VL combination of the VH1 region with an identity of at least 90% to the VH1 region of Vs618 (SEQ ID NO:4) and the VL region with an identity of at least 90% to the VL region of Vs843 (lambda) (SEQ ID NO:15);

the VH/VL combination of the VH1 region with an identity of at least 90% to the VH1 region of Vs624-PTM-low (SEQ ID NO:6) and the VL region with an identity of at least 90% to the VL region of Vs843 (lambda) (SEQ ID NO:15);

the VH/VL combination of the VH1 region with an identity of at least 90% to the VH1 region of Vs635-PTM-low (SEQ ID NO:7) and the VL region with an identity of at least 90% to VL region of Vs843 (lambda) (SEQ ID NO:15);

the VH/VL combination of the VH1 region with an identity of at least 90% to the VH1 region of Vs618 (SEQ ID NO:4) and the VL region with an identity of at least 90% to the VL region of Vs323-PTM-low (lambda) (SEQ ID NO:18);

the VH/VL combination of the VH1 region with an identity of at least 90% to the VH1 region of Vs624-PTM-low (SEQ ID NO:6) and the VL region with an identity of at least 90% to the VL region of Vs323-PTM-low (lambda) (SEQ ID NO:18)—;

the VH/VL combination of the VH1 region with an identity of at least 90% to the VH1 region of Vs618 (SEQ ID NO:4) and the VL region with an identity of at least 90% to the VL region of Vs321 (lambda) (SEQ ID NO:14);

the VH/VL combination of the VH1 region with an identity of at least 90% to the VH1 region of Vs624-PTM-low (SEQ ID NO:6) and the VL region with an identity of at least 90% to the VL region of Vs321 (lambda) (SEQ ID NO:14);

the VH/VL combination of the VH1 region with an identity of at least 90% to the VH1 region of Vs635-PTM-low (SEQ ID NO:7) and the VL region with an identity of at least 90% to the VL region of Vs321 (lambda) (SEQ ID NO:14);

the VH/VL combination of the VH1 region with an identity of at least 90% to the VH1 region of Vs635-PTM-low (SEQ ID NO:7) and the VL region with an identity of at least 90% to the VL region of Vs236 (kappa) (SEQ ID NO:12);

the VH/VL combination of the VH1 region with an identity of at least 90% to the VH1 region of Vs628-PTM-low (SEQ ID NO:10) and the VL region with an identity of at least 90% to the VL region of VS236 (kappa) (SEQ ID NO:12);

the VH/VL combination of the VH1 region with an identity of at least 90% to the VH1 region of Vs628-PTM-low (SEQ ID NO:10) and the VL region with an identity of at least 90% to the VL region of Vs365 (lambda) (SEQ ID NO:13); and the VH/VL combination of the VH1 region with an identity of at least 90% to the VH1 region of Vs628-PTM-low (SEQ ID NO:10) and the VL region with an identity of at least 90% to the VL region of Vs843 (lambda) (SEQ ID NO:15).

5. The library of claim 1, wherein essentially all VH/VL combinations of said library are efficiently displayed at a display rate of at least 0.5 Fab per phage.

6. The library of claim 1, wherein essentially all VH/VL combinations have a monomeric content of at least 85% when expressed in *E. coli* in Fab format.

7. The library of claim 1, wherein essentially all VH/VL combinations have a monomeric content of at least 90% when expressed in a mammalian system in IgG format.

8. The library of claim 1, wherein all VH/VL combinations are thermally stable.

9. A collection of nucleic acid molecules encoding the library members of claim 1.

10. A vector encoding the nucleic acid molecules of claim 9.

11. A recombinant host cell comprising the nucleic acid molecules of claim 9.

12. A method to isolate an antibody specific for an antigen, said method comprising the steps of:
 (a) contacting the library of claim 1 with an antigen;
 (b) removing those members of the library which do not bind to the antigen; and
 (c) recovering those members of the library bound to the antigen.

13. An antibody isolated from the library of claim 1.

14. A recombinant host cell comprising the vector of claim 10.

15. An antibody isolated by the method of claim 12.

16. A collection of nucleic acid molecules encoding the library members of claim 4.

17. A vector encoding the nucleic acid molecules of claim 16.

18. A recombinant host cell comprising the nucleic acid molecules of claim 16.

19. A method to isolate an antibody specific for an antigen, said method comprising the steps of:
 (a) contacting the library of claim 4 with an antigen;
 (b) removing those members of the library which do not bind to the antigen; and
 (c) recovering those members of the library bound to the antigen.

20. An antibody isolated from the library of claim 4.

* * * * *

SEQUENCE LISTING

<160> NUMBER OF SEQ ID NOS: 47

<210> SEQ ID NO 1
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 1

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Ser Met Ser Trp Val Arg Gln Ala Pro Glu Lys Gly Leu Gln Leu Val
        35                  40                  45

Ala Gly Ile Asn Ser Gly Gly Ser Ser Thr Tyr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Met Tyr Tyr Cys
                85                  90                  95

<210> SEQ ID NO 2
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Val Glu Ser Gly Gly Asp Leu Val Lys Pro Gly Gly
1               5                   10                  15

Thr Leu Arg Leu Ser Cys Val Ala Ser Gly Phe Thr Phe Ser Ser Tyr
            20                  25                  30

Asp Met Ser Trp Val Arg Gln Ser Pro Gly Lys Gly Leu Gln Trp Val
        35                  40                  45

Ala Val Ile Trp Asn Asp Gly Ser Ser Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 3
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Glu Ser Gly Gly Asn Leu Val Lys Pro Gly Gly
1               5                   10                  15

Ser Leu Arg Leu Ser Cys Val Ala Ser Gly Leu Thr Phe Tyr Ser Tyr
            20                  25                  30

Ala Ile Tyr Trp Val His Glu Ala Pro Gly Lys Gly Leu Gln Trp Val
        35                  40                  45

Ala Ala Ile Thr Thr Asp Gly Ser Ser Thr Tyr Tyr Thr Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Met Pro Val Tyr Tyr Cys
                85                  90                  95

<210> SEQ ID NO 4
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Glu Met Tyr Trp Val Arg Gln Ala Pro Gly Lys Gly Leu Glu Trp Val
        35                  40                  45

Ala Arg Ile Tyr Glu Ser Gly Ser Thr Thr Tyr Tyr Ala Glu Ala Val
    50                  55                  60

Lys Gly Arg Phe Thr Ile Ser Arg Asp Asn Ala Lys Asn Met Ala Tyr
65                  70                  75                  80

Leu Gln Met Asn Ser Leu Arg Ala Glu Asp Thr Ala Val Tyr Tyr Cys
                85                  90                  95

<210> SEQ ID NO 5
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Asn Tyr
            20                  25                  30

Tyr Met Ile Trp Val Arg Gln Ala Pro Gly Ala Gly Leu Asp Trp Met
        35                  40                  45

Gly Gln Ile Asp Pro Glu Asp Gly Ala Thr Ser Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

<210> SEQ ID NO 6
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Ser Met Ser Trp Val Arg Gln Ala Pro Glu Lys Gly Leu Gln Leu Val
        35                  40                  45

Ala Gly Ile Ser Ser Gly Gly Ser Ser Thr Tyr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Met Tyr Tyr Cys
                85                  90                  95

<210> SEQ ID NO 7
<211> LENGTH: 96
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Val Glu Ser Gly Gly Asp Leu Val Lys Pro Gly Gly
1               5                   10                  15

Thr Leu Arg Leu Ser Cys Val Ala Ser Gly Phe Thr Phe Ser Ser Tyr
            20                  25                  30

Asp Met Ser Trp Val Arg Gln Ser Pro Gly Lys Gly Leu Gln Trp Val
        35                  40                  45

Ala Val Ile Trp Asn Glu Gly Ser Ser Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 8
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Val Glu Ser Gly Gly Asn Leu Val Lys Pro Gly Gly
1               5                   10                  15

Ser Leu Arg Leu Ser Cys Val Ala Ser Gly Leu Thr Phe Tyr Ser Tyr
            20                  25                  30

Ala Ile Tyr Trp Val His Glu Ala Pro Gly Lys Gly Leu Gln Trp Val
        35                  40                  45

Ala Ala Ile Thr Thr Gly Gly Ser Ser Thr Tyr Tyr Thr Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Met Pro Val Tyr Tyr Cys
                85                  90                  95

<210> SEQ ID NO 9
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Glu Met Tyr Trp Val Arg Gln Ala Pro Gly Lys Gly Leu Glu Trp Val
        35                  40                  45

Ala Arg Ile Tyr Glu Ser Gly Ser Thr Thr Tyr Tyr Ala Glu Ala Val
    50                  55                  60
```

```
Lys Gly Arg Phe Thr Ile Ser Arg Asp Asn Ala Lys Asn Met Ala Tyr
 65                  70                  75                  80

Leu Gln Met Asn Ser Leu Arg Ala Glu Asp Thr Ala Val Tyr Tyr Cys
                 85                  90                  95
```

<210> SEQ ID NO 10
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Glu Val Gln Leu Val Gln Ser Gly Ala Glu Val Lys Lys Pro Gly Ala
 1               5                  10                  15

Ser Val Lys Val Ser Cys Lys Thr Ser Gly Tyr Thr Phe Ile Asn Tyr
                 20                  25                  30

Tyr Met Ile Trp Val Arg Gln Ala Pro Gly Ala Gly Leu Asp Trp Met
             35                  40                  45

Gly Gln Ile Asp Pro Glu Gly Gly Ala Thr Ser Tyr Ala Gln Lys Phe
         50                  55                  60

Gln Gly Arg Val Thr Leu Thr Ala Asp Thr Ser Thr Ser Thr Ala Tyr
 65                  70                  75                  80

Met Glu Leu Ser Ser Leu Arg Ala Gly Asp Ile Ala Val Tyr Tyr Cys
                 85                  90                  95
```

<210> SEQ ID NO 11
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Asp Ile Val Met Thr Gln Thr Pro Leu Ser Leu Ser Val Ser Pro Gly
 1               5                  10                  15

Glu Pro Ala Ser Ile Ser Cys Lys Ala Ser Gln Ser Leu Leu His Ser
                 20                  25                  30

Asn Gly Asn Thr Tyr Leu Tyr Trp Phe Arg Gln Lys Pro Gly Gln Ser
             35                  40                  45

Pro Gln Arg Leu Ile Tyr Lys Val Ser Asn Arg Asp Pro Gly Val Pro
         50                  55                  60

Asp Arg Phe Ser Gly Ser Gly Ser Gly Thr Asp Phe Thr Leu Arg Ile
 65                  70                  75                  80

Ser Arg Val Glu Ala Glu Asp Ala Gly Val Tyr Tyr Cys
                 85                  90
```

<210> SEQ ID NO 12
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

```
Glu Ile Val Met Thr Gln Ser Pro Ala Ser Leu Ser Leu Ser Gln Glu
1               5                   10                  15

Glu Lys Val Thr Ile Thr Cys Arg Ala Ser Gln Ser Val Ser Ser Tyr
            20                  25                  30

Leu Ala Trp Tyr Gln Gln Lys Pro Gly Gln Ala Pro Lys Leu Leu Ile
        35                  40                  45

Tyr Gly Thr Ser Asn Arg Ala Thr Gly Val Pro Ser Arg Phe Ser Gly
50                  55                  60

Ser Gly Ser Gly Thr Asp Phe Ser Phe Thr Ile Ser Ser Leu Glu Pro
65                  70                  75                  80

Glu Asp Val Ala Val Tyr Tyr Cys
                85
```

<210> SEQ ID NO 13
<211> LENGTH: 87
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Ser Tyr Val Leu Thr Gln Leu Pro Ser Val Ser Val Thr Leu Arg Gln
1               5                   10                  15

Thr Ala Arg Ile Thr Cys Gly Gly Asp Ser Ile Gly Ser Lys Asn Val
            20                  25                  30

Tyr Trp Tyr Gln Gln Lys Leu Gly Gln Ala Pro Val Leu Ile Ile Tyr
        35                  40                  45

Asp Asp Ser Ser Arg Pro Ser Gly Ile Pro Glu Arg Phe Ser Gly Ala
50                  55                  60

Asn Ser Gly Asn Thr Ala Thr Leu Thr Ile Ser Gly Ala Leu Ala Glu
65                  70                  75                  80

Asp Glu Ala Asp Tyr Tyr Cys
                85
```

<210> SEQ ID NO 14
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Ser Thr Ser
            20                  25                  30

Asn Tyr Pro Gly Trp Tyr Gln Gln Thr Leu Gly Arg Ala Pro Arg Thr
        35                  40                  45

Ile Ile Tyr Arg Thr Ser Ser Arg Pro Ser Gly Val Pro Asn Arg Phe
50                  55                  60
```

```
Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys
                85                  90

<210> SEQ ID NO 15
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Ser Val Leu Thr Gln Pro Ala Ser Val Ser Gly Ser Leu Gly Gln
1               5                   10                  15

Arg Val Thr Ile Ser Cys Thr Gly Ser Ser Ser Asn Val Gly Tyr Gly
                20                  25                  30

Asn Tyr Val Gly Trp Tyr Gln Gln Leu Pro Gly Thr Gly Pro Arg Thr
            35                  40                  45

Leu Ile Tyr Arg Ser Ser Ser Arg Pro Ser Gly Val Pro Asp Arg Phe
        50                  55                  60

Ser Gly Ser Arg Ser Gly Ser Thr Ala Thr Leu Thr Ile Ser Gly Leu
65                  70                  75                  80

Gln Ala Glu Asp Glu Ala Asp Tyr Tyr Cys
                85                  90

<210> SEQ ID NO 16
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Ser Val Leu Thr Gln Pro Ala Ser Val Ser Gly Ser Leu Gly Gln
1               5                   10                  15

Arg Val Thr Ile Ser Cys Thr Gly Ser Ser Ser Asn Ile Gly Arg Gly
                20                  25                  30

Tyr Val Gly Trp Tyr Gln Gln Leu Pro Gly Thr Gly Pro Arg Thr Leu
            35                  40                  45

Ile Tyr Gly Asn Ser Asn Arg Pro Ser Gly Val Pro Asp Arg Phe Ser
        50                  55                  60

Gly Ser Arg Ser Gly Ser Thr Ala Thr Leu Thr Ile Ser Gly Leu Gln
65                  70                  75                  80

Ala Glu Asp Glu Ala Asp Tyr Tyr Cys
                85

<210> SEQ ID NO 17
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 17

Asp Ile Val Met Thr Gln Thr Pro Leu Ser Leu Ser Val Ser Pro Gly
1               5                   10                  15

Glu Pro Ala Ser Ile Ser Cys Lys Ala Ser Gln Ser Leu Leu His Ser
            20                  25                  30

Ser Gly Asn Thr Tyr Leu Tyr Trp Phe Arg Gln Lys Pro Gly Gln Ser
        35                  40                  45

Pro Gln Arg Leu Ile Tyr Lys Val Ser Asn Arg Asp Pro Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Ala Gly Val Tyr Tyr Cys
                85                  90

<210> SEQ ID NO 18
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Ser Val Leu Thr Gln Pro Ala Ser Val Ser Gly Ser Leu Gly Gln
1               5                   10                  15

Arg Val Thr Ile Ser Cys Thr Gly Ser Ser Ser Asn Ile Gly Arg Gly
            20                  25                  30

Tyr Val Gly Trp Tyr Gln Gln Leu Pro Gly Thr Gly Pro Arg Thr Leu
        35                  40                  45

Ile Tyr Gly Ile Ser Asn Arg Pro Ser Gly Val Pro Asp Arg Phe Ser
    50                  55                  60

Gly Ser Arg Ser Gly Ser Thr Ala Thr Leu Thr Ile Ser Gly Leu Gln
65                  70                  75                  80

Ala Glu Asp Glu Ala Asp Tyr Tyr Cys
                85

<210> SEQ ID NO 19
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gaagtgcaat tggtggaaag cggtggcgat ctggtgaaac cagccggcag cctgcgcctg      60
agctgcgtgg ccagcggctt tacctttagc agctatagca tgagctgggt tcgccaggcc     120
ccggaaaaag gcctgcagct ggtggccggc attaatagcg gcggcagcag cacctattat     180
accgatgccg tgaaaggccg ctttaccatt agccgcgata cgccaaaaa caccgtgtac      240 ctgcagatga acagcctgcg ggccgaagat accgccatgt attattgc                  288

<210> SEQ ID NO 20
<211> LENGTH: 288
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 20

```
gaagtgcaat tggttgaaag cggtggtgat ctggttaaac cgggtggcac cctgcgtctg    60
agctgtgttg caagcggttt tacctttagc agctatgata tgagctgggt gcgccagagt   120
ccgggtaaag gtctgcagtg ggttgcagtt atttggaatg atggtagcag cacctattat   180
gcagatgcag ttaaagggcg ttttaccatt agccgtgata atgccaaaaa taccctgtat   240
ctgcagatga atagcctgcg tgcagaggat accgcagtgt attattgc               288
```

<210> SEQ ID NO 21
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
gaagtgcaat tggttgaaag cggtggtaat ctggttaaac cgggtggtag cctgcgtctg    60
agctgtgttg caagcggtct gaccttttat agctatgcaa tttattgggt gcacgaagca   120
ccgggaaaag gtctgcagtg ggttgcagca attaccaccg atggcagcag cacctattac   180
accgatgcag ttaaagggcg ttttaccatt agccgtgata atgccaaaaa taccctgtat   240
ctgcagatga atagcctgcg tgcagaggat atgccggtgt attattgc               288
```

<210> SEQ ID NO 22
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
gaagtgcaat tggttgaaag cggtggtgat ctggttaaac cgggtggtag cctgcgtctg    60
agctgtgttg caagcggttt tacctttagc aactatgaaa tgtattgggt gcggcaggca   120
ccgggtaaag gtctggaatg ggttgcacgc atttatgaaa gcggtagcac cacctattat   180
gcagaagcag ttaaagggcg ttttaccatt agccgtgata acgccaaaaa tatggcatat   240
ctgcagatga atagcctgcg tgcagaggat accgcagtgt attattgc               288
```

<210> SEQ ID NO 23
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

```
gaagtgcaat tggttcagag cggtgccgaa gttaaaaaac cgggtgcaag cgttaaagtt    60
agctgtaaaa ccagcggcta taccttcatc aactattata tgatttgggt gcgccaggca   120
ccgggtgcag gtctggattg gatgggtcag attgatccgg aagaaggtgc aaccagctat   180
```
gcacagaaat tcagggtcg tgttaccctg accgcagata ccagcaccag caccgcatat    240
atggaactga gcagcctgcg tgccggtgat attgcagtgt attattgc    288

<210> SEQ ID NO 24
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
gaagtgcaat tggtggaaag cggtggcgat ctggtgaaac cagccggcag cctgcgcctg    60
agctgcgtgg ccagcggctt tacctttagc agctatagca tgagctgggt tcgccaggcc    120
ccggaaaaag gcctgcagct ggtggccggc attagcagcg gcggcagcag cacctattat    180
accgatgccg tgaaaggccg ctttaccatt agccgcgata cgccaaaaa caccgtgtac    240 ctgcagatga acagcctgcg ggccgaagat accgccatgt attattgc    288

<210> SEQ ID NO 25
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gaagtgcaat tggttgaaag cggtggtgat ctggttaaac cgggtggcac cctgcgtctg    60
agctgtgttg caagcggttt tacctttagc agctatgata tgagctgggt gcgccagagt    120
ccgggtaaag gtctgcagtg ggttgcagtt atttggaatg aaggtagcag cacctattat    180
gcagatgcag ttaaagggcg ttttaccatt agccgtgata atgccaaaaa taccctgtat    240
ctgcagatga atagcctgcg tgcagaggat accgcagtgt attattgc    288

<210> SEQ ID NO 26
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
gaagtgcaat tggttgaaag cggtggtaat ctggttaaac cgggtggtag cctgcgtctg    60
agctgtgttg caagcggtct gaccttttat agctatgcaa tttattgggt gcacgaagca    120
ccggaaaaag gtctgcagtg ggttgcagca attaccaccg gtggcagcag cacctattac    180
accgatgcag ttaaagggcg ttttaccatt agccgtgata atgccaaaaa taccctgtat    240
ctgcagatga atagcctgcg tgcagaggat atgccggtgt attattgc    288

<210> SEQ ID NO 27
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

```
gaagtgcaat tggttgaaag cggtggtgat ctggttaaac cgggtggtag cctgcgtctg    60
agctgtgttg caagcggttt tacctttagc aactatgaaa tgtattgggt gcggcaggca   120
ccgggtaaag gtctggaatg ggttgcacgc atttatgaaa gcggtagcac cacctattat   180
gcagaagcag ttaaagggcg ttttaccatt agccgtgata cgccaaaaa tatggcatat    240 ctgcagatga atagcctgcg tgcagaggat accgcagtgt attattgc               288
```

<210> SEQ ID NO 28
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
gaagtgcaat tggttcagag cggtgccgaa gttaaaaaac cgggtgcaag cgttaaagtt    60
agctgtaaaa ccagcggcta taccttcatc aactattata tgatttgggt gcgccaggca   120
ccgggtgcag gtctggattg gatgggtcag attgatccgg aaggtggtgc aaccagctat   180
gcacagaaat ttcagggtcg tgttaccctg accgcagata ccagcaccag caccgcatat   240
atggaactga gcagcctgcg tgccggtgat attgcagtgt attattgc               288
```

<210> SEQ ID NO 29
<211> LENGTH: 279
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
gatattgtga tgacccagac cccactgagc ctgagcgtga gcccaggcga accagccagc    60
attagctgca aagccagcca gagcctgctg catagcaatg caacaccta tctgtattgg    120 tttcgccaga aaccaggcca gagcccacag cgcctgatct ataaagtgag caaccgcgat   180
ccaggcgtgc cggatcgctt tagcggcagc ggtagcggca ccgattttac cctgcgcatt   240
agtcgcgtgg aagccgaaga cgcaggcgtg tattattgc                         279
```

<210> SEQ ID NO 30
<211> LENGTH: 264
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
gaaattgtta tgacccagag tccggcaagc ctgagcctga gccaagaaga aaaagttacc    60
attacctgtc gtgcaagcca gagcgttagc agctatctgg catggtatca gcagaaaccg   120
ggtcaggcac cgaaactgct gatttatggc accagcaatc gtgcaaccgg tgttccgagc   180
```

```
cgttttagcg gtagcggtag tggcaccgat tttagcttta ccattagcag cctggaaccg    240
gaagacgtgg ccgtgtatta ttgc                                          264
```

<210> SEQ ID NO 31
<211> LENGTH: 261
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

```
agctatgtgc tgacccagct gccgagcgtg agcgtgaccc tgcgccagac cgcacgcatt     60
acctgcggtg gcgatagcat tggcagcaaa aacgtgtatt ggtatcagca gaaactgggc    120
caggcaccgg tgctgattat ctatgatgat agcagtcgcc caagcggcat tccggaacgc    180
tttagcggtg ccaacagcgg caacaccgcc accctgacca ttagcggtgc cctggccgaa    240
gacgaagccg attattactg c                                             261
```

<210> SEQ ID NO 32
<211> LENGTH: 270
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

```
cagaccgttg ttacccaaga accgagcctg agcgttagtc cgggtggcac cgttaccctg     60
acctgtggtc tgagcagcgg tagcgttagc accagcaatt atccaggtgt gtatcagcag    120
accctgggtc gtgcaccgcg taccattatc tatcgtacca gcagccgtcc gagcggtgtt    180
ccgaatcgtt ttagcggtag cattagcggt aataaagcag cactgaccat taccggtgca    240
cagccggaag acgaagccga ttattactgc                                    270
```

<210> SEQ ID NO 33
<211> LENGTH: 270
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33

```
cagagcgttc tgacccagcc tgcaagcgtt agcggtagcc tgggtcagcg tgttaccatt     60
agctgtaccg gtagtagtag caatgttggt tatggtaatt atgttggttg gtatcagcag    120
ctgcctggca ccggtccgcg taccctgatt tatcgtagca gcagccgtcc gagcggtgtt    180
ccggatcgtt ttagcggtag tcgtagcggt agcaccgcaa ccctgaccat tagcggtctg    240
caggcagaag acgaagccga ttattactgc                                    270
```

<210> SEQ ID NO 34
<211> LENGTH: 267
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 34

```
cagagcgttc tgacccagcc tgcaagcgtt agcggtagcc tgggtcagcg tgttaccatt        60
agctgtaccg gtagtagcag caatattggt cgtggttatg ttggttggta tcagcagctg       120
cctggcaccg gtccgcgtac cctgatttat ggtaatagca atcgtccgag cggtgttccg       180
gatcgtttta gcggtagtcg tagcggtagc accgcaaccc tgaccattag cggtctgcag       240
gcagaagacg aagccgatta ttactgc                                            267
```

<210> SEQ ID NO 35
<211> LENGTH: 279
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 35

```
gatattgtga tgacccagac cccactgagc ctgagcgtga gcccaggcga accagccagc        60
attagctgca aagccagcca gagcctgctg catagcagcg gcaacaccta tctgtattgg       120
tttcgccaga aaccaggcca gagcccacag cgcctgatct ataaagtgag caaccgcgat       180
ccaggcgtgc cggatcgctt tagcggcagc ggtagcggca ccgattttac cctgcgcatt       240
agtcgcgtgg aagccgaaga cgcaggcgtg tattattgc                              279
```

<210> SEQ ID NO 36
<211> LENGTH: 267
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 36

```
cagagcgttc tgacccagcc tgcaagcgtt agcggtagcc tgggtcagcg tgttaccatt        60
agctgtaccg gtagtagcag caatattggt cgtggttatg ttggttggta tcagcagctg       120
cctggcaccg gtccgcgtac cctgatttat ggtattagca atcgtccgag cggtgttccg       180
gatcgtttta gcggtagtcg tagcggtagc accgcaaccc tgaccattag cggtctgcag       240
gcagaagacg aagccgatta ttactgc                                            267
```

<210> SEQ ID NO 37
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 37

```
Trp Gly Gln Gly Thr Leu Val Thr Val Ser Ser
1               5                   10
```

<210> SEQ ID NO 38
<211> LENGTH: 10

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Phe Gly Ala Gly Thr Lys Val Glu Leu Lys
1               5                   10

<210> SEQ ID NO 39
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Phe Gly Gly Gly Thr Gln Leu Thr Val Leu
1               5                   10

<210> SEQ ID NO 40
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
tggggccagg gcaccctggt taccgtctcg agc                                 33

<210> SEQ ID NO 41
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
tttggcgcag gtaccaaagt ggaactgaaa                                     30

<210> SEQ ID NO 42
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
tttggcggtg gtacccagct gaccgtgctg                                     30

<210> SEQ ID NO 43
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 43

Trp Gly Gly Asp Gly Phe Tyr Ala Met Asp Tyr
1               5                   10

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Gln His Tyr Thr Thr Pro Pro Thr
1               5

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gln Ser Tyr Asp Ser Ser Leu Ser Gly Val Val
1               5                   10

<210> SEQ ID NO 46
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Glu Val Gln Leu
1

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 47

His His His His His His
1               5
```